US011371090B2

(12) United States Patent
Makrigiorgos et al.

(10) Patent No.: US 11,371,090 B2
(45) Date of Patent: Jun. 28, 2022

(54) COMPOSITIONS AND METHODS FOR MOLECULAR BARCODING OF DNA MOLECULES PRIOR TO MUTATION ENRICHMENT AND/OR MUTATION DETECTION

(71) Applicants: Dana-Farber Cancer Institute, Inc., Boston, MA (US); The Broad Institute, Inc., Cambridge, MA (US)

(72) Inventors: Gerassimos Makrigiorgos, Chestnut Hill, MA (US); Viktor A. Adalsteinsson, Cambridge, MA (US)

(73) Assignees: Dana-Farber Cancer Institute, Inc., Boston, MA (US); The Broad Institute, Inc., Cambridge, MA (US)

( * ) Notice: Subject to any disclaimer, the term of this patent is extended or adjusted under 35 U.S.C. 154(b) by 197 days.

(21) Appl. No.: 16/469,057

(22) PCT Filed: Dec. 12, 2017

(86) PCT No.: PCT/US2017/065747
§ 371 (c)(1),
(2) Date: Jun. 12, 2019

(87) PCT Pub. No.: WO2018/111835
PCT Pub. Date: Jun. 21, 2018

(65) Prior Publication Data
US 2020/0040388 A1 Feb. 6, 2020

Related U.S. Application Data

(60) Provisional application No. 62/522,856, filed on Jun. 21, 2017, provisional application No. 62/502,128, filed on May 5, 2017, provisional application No. 62/433,071, filed on Dec. 12, 2016.

(51) Int. Cl.
*C12Q 1/6858* (2018.01)
*C12Q 1/6806* (2018.01)
*C12Q 1/6883* (2018.01)

(52) U.S. Cl.
CPC ......... *C12Q 1/6858* (2013.01); *C12Q 1/6806* (2013.01); *C12Q 1/6883* (2013.01); *C12Q 2600/156* (2013.01); *C12Q 2600/16* (2013.01)

(58) Field of Classification Search
None
See application file for complete search history.

(56) References Cited

U.S. PATENT DOCUMENTS

| | | |
|---|---|---|
| 4,458,066 A | 7/1984 | Caruthers et al. |
| 4,683,195 A | 7/1987 | Mullis et al. |
| 4,683,202 A | 7/1987 | Mullis |
| 4,800,159 A | 1/1989 | Mullis et al. |
| 5,045,450 A | 9/1991 | Thilly et al. |
| 5,075,217 A | 12/1991 | Weber |
| 5,256,775 A | 10/1993 | Froehler |
| 5,399,491 A | 3/1995 | Kacian et al. |
| 5,409,818 A | 4/1995 | Davey et al. |
| 5,427,930 A | 6/1995 | Birkenmeyer et al. |
| 5,541,308 A | 7/1996 | Hogan et al. |
| 5,554,527 A | 9/1996 | Fickenscher |
| 5,565,340 A | 10/1996 | Chenchik et al. |
| 5,612,473 A | 3/1997 | Wu et al. |
| 5,618,703 A | 4/1997 | Gelfand et al. |
| 5,631,147 A | 5/1997 | Lohman et al. |
| 5,648,211 A | 7/1997 | Fraiser et al. |
| 5,656,461 A | 8/1997 | Demers |
| 5,670,316 A | 9/1997 | Calhoun et al. |
| 5,744,311 A | 4/1998 | Fraiser et al. |
| 5,792,607 A | 8/1998 | Backman et al. |
| 5,846,710 A | 12/1998 | Bajaj |
| 5,849,497 A | 12/1998 | Steinman |
| 5,994,056 A | 11/1999 | Higuchi |
| 6,030,115 A | 2/2000 | Ishiguro et al. |
| 6,174,680 B1 | 1/2001 | Makrigiorgos |
| 6,197,499 B1 | 3/2001 | Hughes et al. |
| 7,435,794 B2 | 10/2008 | Lukyanov et al. |
| 7,618,773 B2 | 11/2009 | Rand et al. |
| 7,635,566 B2 | 12/2009 | Brenner |
| 8,071,338 B2 | 12/2011 | Newton |
| 8,268,564 B2 | 9/2012 | Roth et al. |
| 8,440,404 B2 | 5/2013 | Makarov et al. |
| 8,455,190 B2 | 6/2013 | Makrigiorgos |
| 8,623,603 B2 | 1/2014 | Makrigiorgos |
| 8,628,924 B2 | 1/2014 | Kacian et al. |
| 8,691,509 B2 | 4/2014 | May et al. |

(Continued)

FOREIGN PATENT DOCUMENTS

| | | |
|---|---|---|
| CN | 1650028 A | 8/2005 |
| EP | 0 370 719 A2 | 5/1990 |

(Continued)

OTHER PUBLICATIONS

Partial Supplementary European Search Report for EP12764286.6 dated Nov. 17, 2014.
Extended European Search Report for EP12764286.6 dated Mar. 18, 2015.
Extended European Search Report for EP 17196718.5 dated May 14, 2018.
Extended European Search Report for EP 16815352.6 dated Oct. 16, 2018.
Invitation to Pay Additional Fees for PCT/US2012/031527 dated Aug. 28, 2012.
International Search Report and Written Opinion for PCT/US2012/031527 dated Nov. 5, 2012.
International Preliminary Report on Patentability for PCT/US2012/031527 dated Oct. 10, 2013.

(Continued)

*Primary Examiner* — Samuel C Woolwine
*Assistant Examiner* — Carolyn L Greene
(74) *Attorney, Agent, or Firm* — Wolf, Greenfield & Sacks, P.C.

(57) ABSTRACT

Provided herein are methods to determine the original abundance of mutant alleles of one or more barcoded target sequences following mutation enrichment and sequencing.

20 Claims, 16 Drawing Sheets

(56) References Cited

U.S. PATENT DOCUMENTS

| | | |
|---|---|---|
| 9,133,490 B2 | 9/2015 | Candau-Cachon |
| 9,957,556 B2 | 5/2018 | Makrigiorgos |
| 10,913,977 B2 | 2/2021 | Makrigiorgos |
| 11,030,992 B2 | 6/2021 | Kerr et al. |
| 11,174,510 B2 | 11/2021 | Makrigiorgos |
| 2002/0016680 A1 | 2/2002 | Wang et al. |
| 2002/0045227 A1 | 4/2002 | Wagener |
| 2003/0008286 A1 | 1/2003 | Zou et al. |
| 2003/0092021 A1 | 5/2003 | Thilly |
| 2004/0023207 A1 | 2/2004 | Polansky |
| 2004/0033518 A1 | 2/2004 | Wittwer et al. |
| 2004/0166519 A1 | 8/2004 | Cargill et al. |
| 2005/0089984 A1 | 4/2005 | Ginns et al. |
| 2005/0175996 A1 | 8/2005 | Chen |
| 2005/0266417 A1 | 12/2005 | Barany et al. |
| 2006/0057569 A1 | 3/2006 | Charle |
| 2006/0063175 A1 | 3/2006 | Xu et al. |
| 2006/0263789 A1 | 11/2006 | Kincaid |
| 2007/0020672 A1 | 1/2007 | Wittwer et al. |
| 2007/0154892 A1 | 7/2007 | Wain-Hobson et al. |
| 2008/0254453 A1 | 10/2008 | Shapero et al. |
| 2008/0269068 A1 | 10/2008 | Church et al. |
| 2009/0053698 A1 | 2/2009 | Hayashida |
| 2009/0068652 A1 | 3/2009 | Taylor et al. |
| 2009/0148842 A1 | 6/2009 | Gormley |
| 2010/0173311 A1 | 7/2010 | Grow et al. |
| 2010/0184153 A1 | 7/2010 | Brookes |
| 2010/0203532 A1 | 8/2010 | Makrigiorgos |
| 2010/0233683 A1 | 9/2010 | Molloy et al. |
| 2011/0217714 A1 | 9/2011 | Makrigiorgos |
| 2012/0220494 A1 | 8/2012 | Samuels et al. |
| 2012/0225421 A1 | 9/2012 | Richardson et al. |
| 2013/0059734 A1 | 3/2013 | Molloy et al. |
| 2013/0303385 A1 | 11/2013 | Korlach et al. |
| 2013/0309724 A1 | 11/2013 | Candau-Cachon |
| 2014/0051087 A1 | 2/2014 | Makrigiorgos |
| 2014/0106362 A1 | 4/2014 | Makrigiorgos |
| 2014/0315726 A1 | 10/2014 | Beatty et al. |
| 2015/0147760 A1 | 5/2015 | Gupta et al. |
| 2015/0247182 A1 | 9/2015 | Faham et al. |
| 2016/0046986 A1 | 2/2016 | Eltoukhy et al. |
| 2016/0186237 A1 | 6/2016 | Makrigiorgos et al. |
| 2016/0289670 A1 | 10/2016 | Samuels et al. |
| 2016/0369333 A1 | 12/2016 | Babiarz et al. |
| 2017/0130258 A1 | 5/2017 | Sampas |
| 2018/0187242 A1 | 7/2018 | Makrigiorgos et al. |
| 2018/0282798 A1 | 10/2018 | Makrigiorgos |

FOREIGN PATENT DOCUMENTS

| | | | |
|---|---|---|---|
| EP | 2 004 852 B1 | 12/2010 | |
| GB | 2 293 238 A | 3/1996 | |
| JP | 6-510201 | 11/1994 | |
| JP | 2005-536983 | 12/2005 | |
| JP | 2012-165755 | 9/2012 | |
| WO | WO 1990/11369 A1 | 10/1990 | |
| WO | WO 1990/13668 A1 | 11/1990 | |
| WO | WO 1991/14003 A2 | 9/1991 | |
| WO | WO 1997/19193 A2 | 5/1997 | |
| WO | WO 1999/14226 A2 | 3/1999 | |
| WO | WO 1999/61661 A1 | 12/1999 | |
| WO | WO 2001/068900 A2 | 9/2001 | |
| WO | WO 2002/018659 A2 | 3/2002 | |
| WO | WO 2002/086155 A2 | 10/2002 | |
| WO | WO 2003/072809 A1 | 9/2003 | |
| WO | WO 2005/093101 A1 | 10/2005 | |
| WO | WO 2007/047572 A2 | 4/2007 | |
| WO | WO 2007/087310 A2 | 8/2007 | |
| WO | WO 2007/106534 A2 | 9/2007 | |
| WO | WO 2009/017784 A2 | 2/2009 | |
| WO | WO 2009/019008 A1 | 2/2009 | |
| WO | WO 2010/065626 A1 | 6/2010 | |
| WO | WO 2011/112534 A1 | 9/2011 | |
| WO | WO 2012/129363 A2 | 9/2012 | |
| WO | WO 2012/135664 A2 | 10/2012 | |
| WO | WO 2012/159089 A1 | 11/2012 | |
| WO | WO 2014/142261 A1 | 9/2014 | |
| WO | WO 2015/013166 A1 | 1/2015 | |
| WO | WO-2015100427 A1 * | 7/2015 | ........... C12Q 1/6869 |
| WO | WO 2016/210224 A1 | 12/2016 | |
| WO | WO 2018/174318 A1 | 9/2018 | |

OTHER PUBLICATIONS

International Search Report and Written Opinion for PCT/US2014/047373 dated Nov. 12, 2014.

International Preliminary Report on Patentability for PCT/US2014/047373 dated Feb. 4, 2016.

International Search Report and Written Opinion for PCT/US2016/039167 dated Sep. 26, 2016.

International Preliminary Report on Patentability for PCT/US2016/039167 dated Dec. 26, 2017.

International Preliminary Report on Patentability for PCT/US2017/065747 dated Jun. 27, 2019.

International Search Report and Written Opinion for PCT/US2017/065747 dated Mar. 6, 2018.

International Search Report and Written Opinion for PCT/US2011/027473 dated Jun. 28, 2011.

International Preliminary Report on Patentability for PCT/US2011/027473 dated Sep. 20, 2012.

International Search Report and Written Opinion for PCT/US2018/043506 dated Oct. 9, 2018.

International Preliminary Report on Patentability for PCT/EP2008/006476 dated Feb. 9, 2010.

International Search Report and Written Opinion for PCT/US2008/009248 dated Jan. 6, 2009.

International Preliminary Report on Patentability for PCT/US2008/009248 dated Feb. 2, 2010.

[No Author Listed] BioMath Calculators: Tm Calculation for Oligos. Last accessed Oct. 27, 2014 from https://www.promega.com/techserv/tools/biomath/calc11.htm .

[No Author Listed] COLD-PCR: Very High Sensitivity Mutation Detection. Transgenomic. Jul. 1, 2010: 31 pages. Last accessed at <http://www.transgenomic.com/files/literature/48227300.pdf> on Oct. 25, 2014.

[No Author Listed] Integrated DNA Technologies Molecular Facts and Figures [online] [retrieved on Feb. 17, 2015] retrieved from https://www.idtdna.com/pages/docs/educational-resources/molecular-facts-and-figures.pdf?sfvrsn=4.

[No Author Listed] User Guide for the REVEAL Kit KRAS Exon 2. A Mutation Enrichment Assay Powered by ICE COLD-PCR. Transgenomic, Inc 2012.

[No Author Listed], "Paired-End Sequencing Sample Preparation Guide," Illumina Catalog #PE-930-1001, Sep. 1, 2009 (Sep. 1, 2009), pp. 1-34. Retrieved from the Internet: <http://mmjggl.caltech.edu/sequencing/Paired-End_SamplePrep_Guide_1005063_8.pdf> on Feb. 1, 2018 (Feb. 1, 2018). entire document.

Adalsteinsson: Recent literature: listed in http://personal.broadinstitute.org/viktor/publications.html. 2016.

Ahmadian et al., Pyrosequencing: history, biochemistry and future. Clin Chim Acta. Jan. 2006;363(1-2):83-94. Epub Sep. 13, 2005.

Ahrendt et al., p53 mutations and survival in stage I non-small-cell lung cancer: results of a prospective study. J Natl Cancer Inst. Jul. 2, 2003;95(13):961-70.

Alix-Panabières et al., Clinical Applications of Circulating Tumor Cells and Circulating Tumor DNA as Liquid Biopsy. Cancer Discov. May 2016; 6(5):479-91. doi: 10.1158/2159-8290.CD-15-1483. Epub Mar. 11, 2016.

Altschul et al., Gapped BLAST and PSI-BLAST: a new generation of protein database search programs. Nucleic Acids Res. Sep. 1, 1997;25(17):3389-402.

Amicarelli et al., FLAG assay as a novel method for real-time signal generation during PCR: application to detection and genotyping of KRAS codon 12 mutations. Nucleic Acids Res. 2007;35(19):e131. Epub Oct. 11, 2007.

Aoki et al., Liposome-mediated in vivo gene transfer of antisense K-ras construct inhibits pancreatic tumor dissemination in the murine peritoneal cavity. Cancer Res. Sep. 1, 1995;55(17):3810-6.

(56) References Cited

OTHER PUBLICATIONS

Armour et al., Recent advances in minisatellite biology. FEBS Lett. Jul. 27, 1992;307(1):113-5.

Bacher et al., Improved Detection of Microsatellite Instability in Early Colorectal Lesions. PLoS One. Aug. 7, 2015; 10(8):e0132727. doi: 10.1371/journal.pone.0132727. eCollection 2015.

Bansal et al., Statistical analysis strategies for association studies involving rare variants. Nat Rev Genet. Nov. 2010; 11(11):773-85. doi: 10.1038/nrg2867. Epub Oct. 13, 2010.

Beaucage et al., Deoxynucleoside phosphoramidites—A new class of key intermediates for deoxypolynucleotide synthesis. Tetrahedron Letters. 1981;22(20):1859-62. doi:10.1016/S00404039(01)90461-7.

Beau-Faller et al., Detection of K-Ras mutations in tumour samples of patients with non-small cell lung cancer using PNA-mediated PCR clamping. Br J Cancer. Mar. 24, 2009;100(6):985-92. doi:10.1038/sj.bjc.6604925.

Beggs et al., A study of genomic instability in early preneoplastic colonic lesions. Oncogene. Nov. 14, 2013; 32(46):5333-7. doi: 10.1038/onc.2012.584. Epub Dec. 17, 2012.

Behn et al., Simple and reliable factor V genotyping by PNA-mediated PCR clamping. Thromb Haemost. Apr. 1998;79(4):773-7.

Belinsky et al., Gene promoter methylation in plasma and sputum increases with lung cancer risk. Clin Cancer Res. Sep. 15, 2005;11(18):6505-11.

Bettegowda et al., Detection of circulating tumor DNA in early- and late-stage human malignancies. Sci Transl Med. Feb. 19, 2014; 6(224):224ra24. doi: 10.1126/scitranslmed.3007094.

Bi et al., Detection of known mutation by proof-reading PCR. Nucleic Acids Res. Jun. 15, 1998;26(12):3073-5.

Bid Ard et al., Going with the flow: from circulating tumor cells to DNA. Sci Transl Med. Oct. 16, 2013; 5(207):207ps14. doi: 10.1126/scitranslmed.3006305.

Blake et al., Thermal stability of DNA. Nucleic Acids Res. Jul. 15, 1998;26(14):3323-32.

Boisselier et al., COLD PCR HRM: a highly sensitive detection method for IDH1 mutations. Hum Mutat. Dec. 2010;31(12):1360-5. doi: 10.1002/humu.21365. Epub Nov. 9, 2010.

Botstein et al., Construction of a genetic linkage map in man using restriction fragment length polymorphisms. Am J Hum Genet. May 1980;32(3):314-31.

Braasch et al., Locked nucleic acid (LNA): fine-tuning the recognition of DNA and RNA. Chem Biol. Jan. 2001;8(1):1-7.

Bunyan et al., Different denaturation rates between methylated and non-methylated genomic DNA can result in allele-specific PCR amplification. Open J. Gen. Sep. 2011;1:13-14.

Candau et al., Very High Sensitivity Detection of K-RAS Exon 2 Mutations Using Fast COLD-PCR. AACR 2010 Poster Presentation.

Castellanos-Rizaldos et al., COLD-PCR amplification of bisulfite-converted DNA allows the enrichment and sequencing of rare un-methylated genomic regions. PLoS One. Apr. 11, 2014; 9(4):e94103. doi: 10.1371/journal.pone.0094103. eCollection 2014.

Castellanos-Rizaldos et al., Enhanced ratio of signals enables digital mutation scanning for rare allele detection. J Mol Diagn. May 2015; 17(3):284-92. doi: 10.1016/j.jmoldx.2014.12.003. Epub Mar. 13, 2015.

Castellanos-Rizaldos et al., Enrichment of mutations in multiple DNA sequences using COLD-PCR in emulsion. PLoS One. 2012; 7(12):e51362. doi: 10.1371/journal.pone.0051362. Epub Dec. 6, 2012.

Castellanos-Rizaldos et al., Single-tube, highly parallel mutation enrichment in cancer gene panels by use of temperature-tolerant COLD-PCR. Clin Chem. Jan. 2015; 61(1):267-77. doi: 10.1373/clinchem.2014.228361. Epub Oct. 8, 2014.

Castellanos-Rizaldos et al., Temperature-tolerant COLD-PCR reduces temperature stringency and enables robust mutation enrichment. Clin Chem. Jul. 2012;58(7):1130-8. doi: 10.1373/clinchem.2012.183095. Epub May 15, 2012.

Chakrabarti et al., Highly selective isolation of unknown mutations in diverse DNA fragments: toward new multiplex screening in cancer. Cancer Res. Jul. 15, 2000;60(14):3732-7.

Chan et al., Cloning of CviPII nicking and modification system from chlorella virus NYs-1 and application of Nt.CviPII in random DNA amplification. Nucleic Acids Res. Nov. 29, 2004; 32(21):6187-99. Print 2004.

Chan et al., Noninvasive detection of cancer-associated genome-wide hypomethylation and copy number aberrations by plasma DNA bisulfite sequencing. Proc Natl Acad Sci U S A. Nov. 19, 2013; 110(47):18761-8. doi: 10.1073/pnas.1313995110. Epub Nov. 4, 2013.

Chen et al., Fetal DNA analyzed in plasma from a mother's three consecutive pregnancies to detect paternally inherited aneuploidy. Clin Chem. May 2001;47(5):937-9.

Chiu et al., Hypermethylation of RASSF1A in human and rhesus placentas. Am J Pathol. Mar. 2007;170(3):941-50.

Chou et al., A comparison of high-resolution melting analysis with denaturing high-performance liquid chromatography for mutation scanning: cystic fibrosis transmembrane conductance regulator gene as a model. Am J Clin Pathol. Sep. 2005;124(3):330-8.

Chow et al., Mass spectrometric detection of an SNP panel as an internal positive control for fetal DNA analysis in maternal plasma. Clin Chem. Jan. 2007;53(1):141-2.

Compton, Nucleic acid sequence-based amplification. Nature. Mar. 7, 1991;350(6313):91-2.

Corless et al., Allele-specific polymerase chain reaction for the imatinib-resistant KIT D816V and D816F mutations in mastocytosis and acute myelogenous leukemia. J Mol Diag Nov. 2006;8(5):604-612.

Coutelle, New DNA-analysis techniques (minireview). Biomed Biochim Acta. 1991;50(1):3-10.

Cullen et al., Thermal denaturation of DNA from bromodeoxyuridine substituted cells. Nucleic Acids Res. Jan. 1976; 3(1):49-62.

Däbritz et al., Detection of Ki-ras mutations in tissue and plasma samples of patients with pancreatic cancer using PNA-mediated PCR clamping and hybridisation probes. Br J Cancer. Jan. 31, 2005;92(2):405-12.

Dawson et al., Analysis of circulating tumor DNA to monitor metastatic breast cancer. N Engl J Med. Mar. 28, 2013; 368(13):1199-209. doi: 10.1056/NEJMoa1213261. Epub Mar. 13, 2013.

Delaney et al., GNAS1 mutations occur more commonly than previously thought in intramuscular myxoma. Mod Pathol. May 2009;22(5):718-24. doi: 10.1038/modpathol.2009.32. Epub Mar. 13, 2009.

Di Fiore et al., Clinical relevance of KRAS mutation detection in metastatic colorectal cancer treated by Cetuximab plus chemotherapy. Br J Cancer. Apr. 23, 2007;96(8):1166-9. Epub Mar. 20, 2007.

Diaz et al., Liquid biopsies: genotyping circulating tumor DNA. J Clin Oncol. Feb. 20, 2014; 32(6):579-86. doi: 10.1200/JCO.2012.45.2011. Epub Jan. 21, 2014.

Diaz et al., The molecular evolution of acquired resistance to targeted EGFR blockade in colorectal cancers. Nature. Jun. 28, 2012; 486(7404):537-40. doi: 10.1038/nature11219.

Diehl et al., BEAMing: single-molecule PCR on microparticles in water-in-oil emulsions. Nat Methods. Jul. 2006;3(7):551-9.

Diehl et al., Circulating mutant DNA to assess tumor dynamics. Nat Med. Sep. 2008;14(9):985-90. doi:10.1038/nm.1789. Epub Jul. 31, 2007.

Diehl et al., Detection and quantification of mutations in the plasma of patients with colorectal tumors. Proc Natl Acad Sci U S A. Nov. 8, 2005;102(45):16368-73. Epub Oct. 28, 2005.

Dif-Couvreux et al., [Evaluation of conventional hemi nested PCR analysis for fetal RHD determination in maternal plasma]. J Gynecol Obstet Biol Reprod (Paris). Nov. 2006;35(7):658-64. French.

Dominguez et al., Wild-type blocking polymerase chain reaction for detection of single nucleotide minority mutations from clinical specimens. Oncogene. Oct. 13, 2005;24(45):6830-4. Erratum in: Oncogene. Jan. 26, 2006;25(4):656.

(56) References Cited

OTHER PUBLICATIONS

Dressman et al., Transforming single DNA molecules into fluorescent magnetic particles for detection and enumeration of genetic variations. Proc Natl Acad Sci U S A. Jul. 22, 2003;100(15):8817-22. Epub Jul. 11, 2003.

Eberhard et al., Mutations in the epidermal growth factor receptor and in KRAS are predictive and prognostic indicators in patients with non-small-cell lung cancer treated with chemotherapy alone and in combination with erlotinib. J Clin Oncol. Sep. 1, 2005;23(25):5900-9. Epub Jul. 25, 2005.

Ehrlich, DNA methylation in cancer: too much, but also too little. Oncogene. Aug. 12, 2002; 21(35):5400-13.

Ellegren, Microsatellites: simple sequences with complex evolution. Nat Rev Genet. Jun. 2004; 5(6):435-45.

Engelman et al., Allelic dilution obscures detection of a biologically significant resistance mutation in EGFR-amplified lung cancer. J Clin Invest. Oct. 2006;116(10):2695-706. Epub Aug. 10, 2006.

Fan et al., A versatile assay for high-throughput gene expression profiling on universal array matrices. Genome Res. May 2004;14(5):878-85.

Flaherty et al., Ultrasensitive detection of rare mutations using next-generation targeted resequencing. Nucleic Acids Res. Jan. 2012; 40(1):e2. doi: 10.1093/nar/gkr861. Epub Oct. 19, 2011.

Forshew et al., Noninvasive identification and monitoring of cancer mutations by targeted deep sequencing of plasma DNA. Sci Transl Med. May 30, 2012; 4(136):136ra68. doi: 10.1126/scitranslmed. 3003726.

Frommer et al., A genomic sequencing protocol that yields a positive display of 5-methylcytosine residues in individual DNA strands. Proc Natl Acad Sci U S A. Mar. 1, 1992;89(5):1827-31.

Fuery et al., Detection of rare mutant alleles by restriction endonuclease-mediated selective-PCR: assay design and optimization. Clin Chem. May 2000;46(5):620-4.

Galbiati et al., Novel use of Full COLD-PCR protocol for noninvasive prenatal diagnosis of genetic diseases. Clin Chem. Jan. 2011;57(1):136-8. doi: 10.1373/clinchem.2010.155671. Epub Oct. 25, 2010.

Gan et al., Applicability of next generation sequencing technology in microsatellite instability testing. Genes (Basel). Feb. 12, 2015; 6(1):46-59. doi: 10.3390/genes6010046.

Gao et al., DNA-guided genome editing using the Natronobacterium gregoryi Argonaute. Nat Biotechnol. Jul. 2016; 34(7):768-73. doi: 10.1038/nbt.3547. Epub May 2, 2016.

Genbank Accession No. L32764.1—Human coagulation factor v gene, exon 10 (GI: 488093, submitted Nov. 10, 1994, retrieved on Feb. 16, 2015 from http://www.ncbi.nlm.nih.gov/nuccore/L32764.1).

Giesendorf et al., Molecular beacons: a new approach for semiautomated mutation analysis. Clin Chem. Mar. 1998;44(3):482-6.

Girotti et al., Application of Sequencing, Liquid Biopsies, and Patient-Derived Xenografts for Personalized Medicine in Melanoma. Cancer Discov. Mar. 2016; 6(3):286-99. doi: 10.1158/2159-8290.CD-15-1336. Epub Dec. 29, 2015.

Gnirke et al., Solution hybrid selection with ultra-long oligonucleotides for massively parallel targeted sequencing. Nat Biotechnol. Feb. 2009; 27(2):182-9. doi: 10.1038/nbt.1523. Epub Feb. 1, 2009.

Gonzalez et al., Microsatellite alterations and TP53 mutations in plasma DNA of small-cell lung cancer patients: follow-up study and prognostic significance. Ann Oncol. Sep. 2000;11(9):1097-104.

Goodwin et al., Coming of age: ten years of next-generation sequencing technologies. Nat Rev Genet. May 17, 2016; 17(6):333-51. doi: 10.1038/nrg.2016.49.

Gray, Cancer: Genomics of metastasis. Nature. Apr. 15, 2010;464(7291):989-90. doi:10.1038/464989a.

Greenman et al., Patterns of somatic mutation in human cancer genomes. Nature. Mar. 8, 2007;446(7132):153-8.

Gregory et al., Targeted single molecule mutation detection with massively parallel sequencing. Nucleic Acids Res. Feb. 18, 2016; 44(3):e22. doi: 10.1093/nar/gkv915. Epub Sep. 17, 2015.

Grossi et al., Prognostic significance of K-ras, p53, bcl-2, PCNA, CD34 in radically resected non-small cell lung cancers. Eur J Cancer. Jun. 2003;39(9):1242-50.

Gu et al., Depletion of Abundant Sequences by Hybridization (DASH): using Cas9 to remove unwanted high-abundance species in sequencing libraries and molecular counting applications. Genome Biol. Mar. 4, 2016; 17:41. doi: 10.1186/s13059-016-0904-5.

Guatelli et al., Isothermal, in vitro amplification of nucleic acids by a multienzyme reaction modeled after retroviral replication. Proc Natl Acad Sci U S A. Mar. 1990;87(5):1874-8. Erratum in: Proc Natl Acad Sci U S A Oct. 1990;87(19):7797.

Guha et al., Differential strand separation at critical temperature: a minimally disruptive enrichment method for low-abundance unknown DNA mutations. Nucleic Acids Res. Feb. 1, 2013; 41(3):e50. doi: 10.1093/nar/gks1250. Epub Dec. 20, 2012.

Gundry et al., Amplicon melting analysis with labeled primers: a closed-tube method for differentiating homozygotes and heterozygotes. Clin Chem. Mar. 2003;49(3):396-406.

Gyllensten et al., Generation of single-stranded DNA by the polymerase chain reaction and its application to direct sequencing of the HLA-DQA locus. Proc Natl Acad Sci U S A. Oct. 1988;85(20):7652-6.

Heather et al., The sequence of sequencers: The history of sequencing DNA. Genomics. Jan. 2016; 107(1):1-8. doi: 10.1016/j.ygeno.2015.11.003. Epub Nov. 10, 2015.

Henikoff et al., Amino acid substitution matrices from protein blocks. Proc Natl Acad Sci U S A. Nov. 15, 1992;89(22):10915-9.

Hiatt et al., Single molecule molecular inversion probes for targeted, high-accuracy detection of low-frequency variation. Genome Res. May 2013; 23(5):843-54. doi: 10.1101/gr.147686.112. Epub Feb. 4, 2013.

Hibi et al., Molecular detection of genetic alterations in the serum of colorectal cancer patients. Cancer Res. Apr. 1, 1998;58(7):1405-7.

Higgins et al., Detection of tumor PIK3CA status in metastatic breast cancer using peripheral blood. Clin Cancer Res. Jun. 15, 2012; 18(12):3462-9. doi: 10.1158/1078-0432.CCR-11-2696. Epub Mar. 15, 2012.

Hindson et al., High-throughput droplet digital PCR system for absolute quantitation of DNA copy number. Anal Chem. Nov. 15, 2011; 83(22):8604-10. doi: 10.1021/ac202028g. Epub Oct. 28, 2011.

How-Kit et al., Sensitive detection of KRAS mutations using enhanced-ice-COLD-PCR mutation enrichment and direct sequence identification. Hum Mutat. Nov. 2013; 34(11):1568-80. doi: 10.1002/humu.22427. Epub Sep. 17, 2013.

How-Kit et al., Ultrasensitive detection and identification of BRAF V600 mutations in fresh frozen, FFPE, and plasma samples of melanoma patients by E-ice-COLD-PCR. Anal Bioanal Chem. Sep. 2014; 406(22):5513-20. doi: 10.1007/s00216-014-7975-5. Epub Jun. 27, 2014.

Huang et al., Mutations in exon 7 and 8 of p53 as poor prognostic factors in patients with non-small cell lung cancer. Oncogene. May 14, 1998;16(19):2469-77.

Huang et al., Mutations of p53 and K-ras genes as prognostic factors for non-small cell lung cancer. Int J Oncol. Mar. 1998;12(3):553-63.

Igloi, Variability in the stability of DNA-peptide nucleic acid (PNA) single-base mismatched duplexes: real-time hybridization during affinity electrophoresis in PNA-containing gels. Proc Natl Acad Sci U S A. Jul. 21, 1998;95(15):8562-7.

Ito et al., Tet proteins can convert 5-methylcytosine to 5-formylcytosine and 5-carboxylcytosine. Science. Sep. 2, 2011; 333(6047):1300-3. doi: 10.1126/science.1210597. Epub Jul. 21, 2011.

Jackson et al., Specific p53 mutations detected in plasma and tumors of hepatocellular carcinoma patients by electrospray ionization mass spectrometry. Cancer Res. Jan. 1, 2001;61(1):33-5.

Janavicius et al., Microsatellite instability detection by high-resolution melting analysis. Clin Chem. Nov. 2010; 56(11):1750-7. doi: 10.1373/clinchem.2010.150680. Epub Sep. 17, 2010.

Jänne et al., A rapid and sensitive enzymatic method for epidermal growth factor receptor mutation screening. Clin Cancer Res. Feb. 1, 2006;12(3 Pt 1):751-8.

(56) References Cited

OTHER PUBLICATIONS

Jee et al., Rates and mechanisms of bacterial mutagenesis from maximum-depth sequencing. Nature. Jun. 30, 2016; 534(7609):693-6. Epub Jun. 22, 2016.
Jeffreys et al., DNA enrichment by allele-specific hybridization (DEASH): a novel method for haplotyping and for detecting low-frequency base substitutional variants and recombinant DNA molecules. Genome Res. Oct. 2003;13(10):2316-24.
Johnson et al., Plasma nucleic acids in the diagnosis and management of malignant disease. Clin Chem. Aug. 2002; 48(8):1186-93.
Kanehisa, Use of statistical criteria for screening potential homologies in nucleic acid sequences. Nucleic Acids Res. Jan. 11, 1984;12(1 Pt 1):203-13.
Karlin et al., Applications and statistics for multiple high-scoring segments in molecular sequences. Proc Natl Acad Sci U S A. Jun. 15, 1993;90(12):5873-7.
Khrapko et al., Constant denaturant capillary electrophoresis (CDCE): a high resolution approach to mutational analysis. Nucleic Acids Res. Feb. 11, 1994;22(3):364-9.
Kimura et al., Mutant DNA in plasma of lung cancer patients: potential for monitoring response to therapy. Ann N Y Acad Sci. Jun. 2004;1022:55-60.
Kinde et al., Detection and quantification of rare mutations with massively parallel sequencing. Proc Natl Acad Sci U S A. Jun. 7, 2011; 108(23):9530-5. doi: 10.1073/pnas.1105422108. Epub May 17, 2011.
Koboldt et al., VarScan: variant detection in massively parallel sequencing of individual and pooled samples. Bioinformatics. Sep. 1, 2009; 25(17):2283-5. doi: 10.1093/bioinformatics/btp373. Epub Jun. 19, 2009.
Kopreski et al., Somatic mutation screening: identification of individuals harboring K-ras mutations with the use of plasma DNA. J Natl Cancer Inst. Jun. 7, 2000;92(11):918-23.
Kosaka et al., Mutations of the epidermal growth factor receptor gene in lung cancer: biological and clinical implications. Cancer Res. Dec. 15, 2004;64(24):8919-23.
Koshkin et al., LNA (Locked Nucleic Acids): Synthesis of the adenine, cytosine, guanine, 5-methylcytosine, thymine and uracil bicyclonucleoside monomers, oligomerisation, and unprecedented nucleic acid recognition. Tetrahedron. 1998;54(14):3607-30. doi:10.1016/s00404020(98)00094-5.
Kuang et al., Noninvasive detection of EGFR T790M in gefitinib or erlotinib resistant non-small cell lung cancer. Clin Cancer Res. Apr. 15, 2009; 15(8):2630-6. doi: 10.1158/1078-0432.CCR-08-2592. Epub Apr. 7, 2009.
Kuliński et al., Comparative calorimetric studies on the dynamic conformation of plant 5S rRNA: II. Structural interpretation of the thermal unfolding patterns for lupin seeds and wheat germ. Nucleic Acids Res. May 11, 1991;19(9):2449-55.
Kwoh et al., Transcription-based amplification system and detection of amplified human immunodeficiency virus type 1 with a bead-based sandwich hybridization format. Proc Natl Acad Sci U S A. Feb. 1989;86(4):1173-7.
Kwok, Finding a needle in a haystack: detection and quantification of rare mutant alleles are coming of age. Clin Chem. May 2000;46(5):593-4.
Kwok, High-throughput genotyping assay approaches. Pharmacogenomics. Feb. 2000;1(1):95-100.
Ladas et al., Enhanced detection of microsatellite instability using pre-PCR elimination of wild-type DNA homo-polymers in tissue and liquid biopsies. Nucleic Acids Res. Jul. 6, 2018; 46(12):e74. doi: 10.1093/nar/gky251.
Lander et al., Mapping mendelian factors underlying quantitative traits using RFLP linkage maps. Genetics. Jan. 1989;121(1):185-99. Erratum in: Genetics Feb. 1994;136(2):705.
Latorra et al., Enhanced allele-specific PCR discrimination in SNP genotyping using 3' locked nucleic acid (LNA) primers. Hum Mutat. Jul. 2003;22(1):79-85.

Lawrence et al., Mutational heterogeneity in cancer and the search for new cancer-associated genes. Nature. Jul. 11, 2013; 499(7457):214-218. doi: 10.1038/nature12213. Epub Jun. 16, 2013.
Lázaro et al., Mutation analysis of genetic diseases by asymmetric-PCR SSCP and ethidium bromide staining: application to neurofibromatosis and cystic fibrosis. Mol Cell Probes. Oct. 1992;6(5):357-9.
Li et al., BEAMing up for detection and quantification of rare sequence variants. Nat Methods. Feb. 2006;3(2):95-7.
Li et al., Coamplification at lower denaturation temperature-PCR increases mutation-detection selectivity of TaqMan-based real-time PCR. Clin Chem. Apr. 2009;55(4):748-56. doi:10.1373/clinchem.2008.113381. Epub Feb. 20, 2009.
Li et al., COLD-PCR: a new platform for highly improved mutation detection in cancer and genetic testing. Biochem Soc Trans. Apr. 2009;37(Pt 2):427-32. doi: 10.1042/BST0370427.
Li et al., Multiplex padlock targeted sequencing reveals human hypermutable CpG variations. Genome Res. Sep. 2009;19(9):1606-15. doi: 10.1101/gr.092213.109. Epub Jun. 12, 2009.
Li et al., Replacing PCR with COLD-PCR enriches variant DNA sequences and redefines the sensitivity of genetic testing. Nat Med. May 2008; 14(5):579-84. doi: 10.1038/nm1708. Epub Apr. 13, 2008.
Li et al., s-RT-MELT for rapid mutation scanning using enzymatic selection and real time DNA-melting: new potential for multiplex genetic analysis. Nucleic Acids Res. 2007;35(12):e84. Epub Jun. 1, 2007.
Li et al., Two-round coamplification at lower denaturation temperature-PCR (COLD-PCR)-based sanger sequencing identifies a novel spectrum of low-level mutations in lung adenocarcinoma. Hum Mutat. Nov. 2009;30(11):1583-90. doi: 10.1002/humu.21112.
Liew et al., Genotyping of single-nucleotide polymorphisms by high-resolution melting of small amplicons. Clin Chem. Jul. 2004;50(7):1156-64.
Lipsky et al., DNA melting analysis for detection of single nucleotide polymorphisms. Clin Chem. Apr. 2001;47(4):635-44.
Li-Sucholeiki et al., A sensitive scanning technology for low frequency nuclear point mutations in human genomic DNA. Nucleic Acids Res. May 1, 2000;28(9):E44.
Liu et al., Denaturing high performance liquid chromatography (DHPLC) used in the detection of germline and somatic mutations. Nucleic Acids Res. Mar. 15, 1998;26(6):1396-400.
Liu et al., Detection of hotspot mutations and polymorphisms using an enhanced PCR-RFLP approach. Hum Mutat. May 2003;21(5):535-41.
Liu et al., Inverse PCR-based RFLP scanning identifies low-level mutation signatures in colon cells and tumors. Cancer Res. Apr. 1, 2004;64(7):2544-51.
Llop et al., Development of a highly sensitive nested-PCR procedure using a single closed tube for detection of Erwinia amylovora in asymptomatic plant material. Appl Environ Microbiol. May 2000; 66(5):2071-8.
Lo et al., Plasma nucleic acid analysis by massively parallel sequencing: pathological insights and diagnostic implications. J Pathol. Nov. 2011; 225(3):318-23. doi: 10.1002/path.2960. Epub Aug. 24, 2011.
Lou et al., High-throughput DNA sequencing errors are reduced by orders of magnitude using circle sequencing. Proc Natl Acad Sci U S A. Dec. 3, 2013; 110(49):19872-7. doi: 10.1073/pnas.1319590110. Epub Nov. 15, 2013.
Luo et al., Detection of rare mutant K-ras DNA in a single-tube reaction using peptide nucleic acid as both PCR clamp and sensor probe. Nucleic Acids Res. Jan. 23, 2006;34(2):e12.
Luthra et al., COLD-PCR finds hot application in mutation analysis. Clin Chem. Dec. 2009;55(12):2077-8. doi: 10.1373/clinchem.2009.136143. Epub Oct. 15, 2009.
Makrigiorgos, PCR-based detection of minority point mutations. Hum Mutat. May 2004;23(5):406-12.
Mamon et al., Preferential amplification of apoptotic DNA from plasma: potential for enhancing detection of minor DNA alterations in circulating DNA. Clin Chem. Sep. 2008;54(9):1582-4. doi:10.1373/clinchem.2008.104612.

(56) References Cited

OTHER PUBLICATIONS

Mancini et al., The use of COLD-PCR and high-resolution melting analysis improves the limit of detection of KRAS and BRAF mutations in colorectal cancer. J Mol Diagn. Sep. 2010;12(5):705-11. doi: 10.2353/jmoldx.2010.100018. Epub Jul. 8, 2010.

Mao et al., Synthesis of radioactive single-stranded DNA probes using asymmetrical PCR and oligonucleotide random priming. Biotechniques. Oct. 1999;27(4):674-6, 678.

Margulies et al., Genome sequencing in microfabricated high-density picolitre reactors. Nature. Sep. 15, 2005;437(7057):376-80. Epub Jul. 31, 2005. Erratum in: Nature. May 4, 2006;441(7089):120. Ho, Chun He [corrected to Ho, Chun Heen].

Maruvka et al., Analysis of somatic microsatellite indels identifies driver events in human tumors. Nat Biotechnol. Oct. 2017;35(10):951-959. doi: 10.1038/nbt.3966. Epub Sep. 11, 2017.

Maulik et al., Novel non-isotopic detection of MutY enzyme-recognized mismatches in DNA via ultrasensitive detection of aldehydes. Nucleic Acids Res. Mar. 1, 1999;27(5):1316-22.

Mayall et al., Mutations of p53 gene can be detected in the plasma of patients with large bowel carcinoma. J Clin Pathol.Aug. 1998;51(8):611-3.

Mertes et al., Targeted enrichment of genomic DNA regions for next-generation sequencing. Brief Funct Genomics. Nov. 2011;10(6):374-86. doi: 10.1093/bfgp/elr033. Epub Nov. 26, 2011.

Milbury et al., COLD-PCR enrichment of rare cancer mutations prior to targeted amplicon resequencing. Clin Chem. Mar. 2012;58(3):580-9. doi: 10.1373/clinchem.2011.176198. Epub Dec. 21, 2011.

Milbury et al., COLD-PCR-enhanced high-resolution melting enables rapid and selective identification of low-level unknown mutations. Clin Chem. Dec. 2009;55(12):2130-43. doi: 10.1373/clinchem.2009.131029. Epub Oct. 8, 2009.

Milbury et al., Ice-COLD-PCR enables rapid amplification and robust enrichment for low-abundance unknown DNA mutations. Nucleic Acids Res. Jan. 2011;39(1):e2. doi: 10.1093/nar/gkq899. Epub Oct. 11, 2010.

Milbury et al., Multiplex amplification coupled with COLD-PCR and high resolution melting enables identification of low-abundance mutations in cancer samples with low DNA content. J Mol Diagn. Mar. 2011;13(2):220-32. doi: 10.1016/j.jmoldx.2010.10.008.

Milbury et al., PCR-based methods for the enrichment of minority alleles and mutations. Clin Chem. Apr. 2009;55(4):632-40. doi:10.1373/clinchem.2008.113035. Epub Feb. 6, 2009.

Misale et al., Emergence of KRAS mutations and acquired resistance to anti-EGFR therapy in colorectal cancer. Nature. Jun. 28, 2012; 486(7404):532-6. doi: 10.1038/nature11156.

Mitra et al., Digital genotyping and haplotyping with polymerase colonies. Proc Natl Acad Sci U S A. May 13, 2003;100(10):5926-31. Epub May 2, 2003.

Mitra et al., Fluorescent in situ sequencing on polymerase colonies. Anal Biochem. Sep. 1, 2003;320(1):55-65. Erratum in: Anal Biochem. May 15, 2004;328(2):245.

Mitsudomi et al., Prognostic significance of p53 alterations in patients with non-small cell lung cancer: a meta-analysis. Clin Cancer Res. Oct. 2000;6(10):4055-63.

Montgomery et al., Simultaneous mutation scanning and genotyping by high-resolution DNA melting analysis. Nat Protoc. 2007;2(1):59-66.

Moorthie et al., Review of massively parallel DNA sequencing technologies. Hugo J. Dec. 2011; 5(1-4):1-12. doi: 10.1007/s11568-011-9156-3. Epub Oct. 27, 2011.

Murakami et al., p53 gene mutations are associated with shortened survival in patients with advanced non-small cell lung cancer: an analysis of medically managed patients. Clin Cancer Res. Feb. 2000;6(2):526-30.

Murphy et al., Enriching mutant sequences by modulating the denaturation time during PCR. Clin Chem. Jul. 2014; 60(7):1014-6. doi: 10.1373/clinchem.2014.221465. Epub May 5, 2014.

Murphy et al., NRAS mutations with low allele burden have independent prognostic significance for patients with lower risk myelodysplastic syndromes. Leukemia. Oct. 2013; 27(10):2077-81. doi: 10.1038/leu.2013.160. Epub May 27, 2013.

Nagai et al., Development of a microchamber array for picoliter PCR. Anal Chem. Mar. 1, 2001;73(5):1043-7.

Nagai et al., High-throughput PCR in silicon based microchamber array. Biosens Bioelectron. Dec. 2001;16(9-12):1015-9.

Narayan et al., Ultrasensitive measurement of hotspot mutations in tumor DNA in blood using error-suppressed multiplexed deep sequencing. Cancer Res. Jul. 15, 2012; 72(14):3492-8. doi: 10.1158/0008-5472.CAN-11-4037. Epub May 10, 2012.

Newman et al., An ultrasensitive method for quantitating circulating tumor DNA with broad patient coverage. Nat Med. May 2014; 20(5):548-54. doi: 10.1038/nm.3519. Epub Apr. 6, 2014.

Newman et al., Integrated digital error suppression for improved detection of circulating tumor DNA. Nat Biotechnol. May 2016; 34(5):547-555. doi: 10.1038/nbt.3520. Epub Mar. 28, 2016.

Nickerson et al., Random mutagenesis-PCR to introduce alterations into defined DNA sequences for validation of SNP and mutation detection methods. Hum Mutat. Mar. 2001;17(3):210-9.

Nilsen et al., The enzyme and the cDNA sequence of a thermolabile and double-strand specific DNase from Northern shrimps (*Pandalus borealis*). PLoS One. Apr. 22, 2010;5(4):e10295. doi: 10.1371/journal.pone.0010295.

Nollau et al., Methods for detection of point mutations: performance and quality assessment. IFCC Scientific Division, Committee on Molecular Biology Techniques. Clin Chem. Jul. 1997;43(7):1114-28.

Obika et al., Stability and structural features of the duplexes containing nucleoside analogues with a fixed N-type conformation, 2'-O,4'-C-methyleneribonucleosides. Tetrahedron Lett. 1998;39:5401-4.

Ogino et al., Sensitive sequencing method for KRAS mutation detection by Pyrosequencing. J Mol Diagn. Aug. 2005;7(3):413-21.

Oldenburg et al., Selective amplification of rare mutations using locked nucleic acid oligonucleotides that competitively inhibit primer binding to wild-type DNA. J Invest Dermatol. Feb. 2008;128(2):398-402. Epub Jun. 21, 2007.

Orita et al., Rapid and sensitive detection of point mutations and DNA polymorphisms using the polymerase chain reaction. Genomics. Nov. 1989;5(4):874-9.

Orum et al., Single base pair mutation analysis by PNA directed PCR clamping. Nucleic Acids Res. Nov. 25, 1993;21(23):5332-6.

Orum, PCR clamping. Curr Issues Mol Biol. Jan. 2000;2(1):27-30.

Oxnard et al., Noninvasive Detection of Response and Resistance in EGFR-Mutant Lung Cancer Using Quantitative Next-Generation Genotyping of Cell-Free Plasma DNA. Clin Cancer Res. Mar. 15, 2014; 20(6):1698-1705. doi: 10.1158/1078-0432.CCR-13-2482. Epub Jan. 15, 2014.

Ozsolak, Third-generation sequencing techniques and applications to drug discovery. Expert Opin Drug Discov. Mar. 2012; 7(3):231-43. doi: 10.1517/17460441.2012.660145. Epub Feb. 2, 2012.

Paez et al., EGFR mutations in lung cancer: correlation with clinical response to gefitinib therapy. Science. Jun. 4, 2004;304(5676):1497-500. Epub Apr. 29, 2004.

Paner et al., Analysis of melting transitions of the DNA hairpins formed from the oligomer sequences d[GGATAC(X)4GTATCC] (X=A, T, G, C). Biopolymers. Dec. 1990;29(14):1715-34.

Pearson et al., Improved tools for biological sequence comparison. Proc Natl Acad Sci U S A. Apr. 1988;85(8):2444-8.

Persson et al., Four-color multiplex reverse transcription polymerase chain reaction—overcoming its limitations. Anal Biochem. Sep. 1, 2005;344(1):33-42.

Petrie et al., Deep sequencing analysis of mutations resulting from the incorporation of dNTP analogs. Nucleic Acids Res. Dec. 2010;38(22):8095-104. doi:10.1093/nar/gkq685. Epub Aug. 6, 2010.

Pinzani et al., BRAFV600E detection in melanoma is highly improved by COLD-PCR. Clin Chim Acta. May 12, 2011;412(11-12):901-5. doi: 10.1016/j.cca.2011.01.014. Epub Jan. 22, 2011.

Pomp et al., Organic solvents as facilitators of polymerase chain reaction. Biotechniques. Jan. 1991;10(1):58-9.

Porreca et al., Polony DNA sequencing. Curr Protoc Mol Biol. Nov. 2006;Chapter 7:Unit 7.8. doi: 10.1002/0471142727.mb0708s76.

(56) References Cited

OTHER PUBLICATIONS

Qin et al., Ultra deep sequencing detects a low rate of mosaic mutations in tuberous sclerosis complex. Hum Genet. Mar. 2010;127(5):573-82. doi: 10.1007/s00439-010-0801-z. Epub Feb. 18, 2010.

Qiu et al., Duplex-specific nuclease-mediated bioanalysis. Trends Biotechnol. Mar. 2015; 33(3):180-8. doi: 10.1016/j.tibtech.2014.12.008. Epub Jan. 29, 2015.

Raja et al., Temperature-controlled primer limit for multiplexing of rapid, quantitative reverse transcription-PCR assays: application to intraoperative cancer diagnostics. Clin Chem. Aug. 2002;48(8):1329-37.

Reckamp et al., A Highly Sensitive and Quantitative Test Platform for Detection of NSCLC EGFR Mutations in Urine and Plasma. J Thorac Oncol. Oct. 2016; 11(10):1690-700. doi: 10.1016/j.jtho.2016.05.035. Epub Jul. 25, 2016.

Reed et al., Sensitivity and specificity of single-nucleotide polymorphism scanning by high-resolution melting analysis. Clin Chem. Oct. 2004;50(10):1748-54. Epub Aug. 12, 2004.

Rehbein et al., Comparison of different methods to produce single-strand DNA for identification of canned tuna by single-strand conformation polymorphism analysis. Electrophoresis. Jun. 1998;19(8-9):1381-4.

Reis-Filho, Next-generation sequencing. Breast Cancer Res. 2009;11 Suppl 3:S12. doi: 10.1186/bcr2431. Epub Dec. 18, 2009.

Richardson et al., BEAMing up personalized medicine: mutation detection in blood. Clin Cancer Res. Jun. 15, 2012; 18(12):3209-11. doi: 10.1158/1078-0432.CCR-12-0871. Epub May 1, 2012.

Riesewijk et al., Monoallelic expression of human PEG1/MEST is paralleled by parent-specific methylation in fetuses. Genomics. Jun. 1, 1997;42(2):236-44.

Saiki et al., Enzymatic amplification of beta-globin genomic sequences and restriction site analysis for diagnosis of sickle cell anemia. Science. Dec. 20, 1985;230(4732):1350-4.

Sanchez et al., Two-temperature LATE-PCR endpoint genotyping. BMC Biotechnol. Dec. 4, 2006;6:44.

Saunders et al., Interlaboratory study on thermal cycler performance in controlled PCR and random amplified polymorphic DNA analyses. Clin Chem. Jan. 2001;47(1):47-55.

Schmitt et al., Detection of ultra-rare mutations by next-generation sequencing. Proc Natl Acad Sci U S A. Sep. 4, 2012; 109(36):14508-13. doi: 10.1073/pnas.1208715109. Epub Aug. 1, 2012.

Schuermann et al., PNA clamping techniques for the determination of oncogene mutations. Methods Mol Biol. 2002;208:165-79.

Schuermann, Detection of K-ras and p53 mutations by "mutant-enriched" PCR-RFLP. Methods Mol Biol. 2003;75:325-33.

Schwaederle et al., Use of Liquid Biopsies in Clinical Oncology: Pilot Experience in 168 Patients. Clin Cancer Res. Nov. 15, 2016; 22(22):5497-5505. doi: 10.1158/1078-0432.CCR-16-0318. Epub May 16, 2016.

Seyama et al., A novel blocker-PCR method for detection of rare mutant alleles in the presence of an excess amount of normal DNA. Nucleic Acids Res. May 25, 1992;20(10):2493-6.

Shagin et al., A novel method for SNP detection using a new duplex-specific nuclease from crab hepatopancreas. Genome Res. Dec. 2002; 12(12):1935-42.

Shah et al., Mutational evolution in a lobular breast tumour profiled at single nucleotide resolution. Nature. Oct. 8, 2009;461(7265):809-13. doi: 10.1038/nature08489.

Shao et al., p53 mutation in plasma DNA and its prognostic value in breast cancer patients. Clin Cancer Res. Aug. 2001;7(8):2222-7. Retraction in: Shao ZM, Wu J, Shen ZZ, Nguyen M. Clin Cancer Res. Sep. 2002;8(9):3027.

Shaw et al., Microsatellite alterations plasma DNA of primary breast cancer patients. Clin Cancer Res. Mar. 2000; 6(3):1119-24.

Shi et al., Ultra-sensitive detection of BRAF V600E and G469A mutations by ICE COLD-PCR and BLOCKer sequencing. Sep. 2011 Poster.

Shi et al., Use of BLOCker Sequencing (BLocking Oligonucleotide Cycle Sequencing) after Ice COLD-PCR for detection of K-RAS and BRAF mutations. May 2011 Poster.

Shigematsu et al., Clinical and biological features associated with epidermal growth factor receptor gene mutations in lung cancers. J Natl Cancer Inst. Mar. 2, 2005;97(5):339-46.

Silva et al., Tumor DNA in plasma at diagnosis of breast cancer patients is a valuable predictor of disease-free survival. Clin Cancer Res. Dec. 2002;8(12):3761-6.

Siravegna et al., Clonal evolution and resistance to EGFR blockade in the blood of colorectal cancer patients. Nat Med. Jul. 2015; 21(7):795-801. doi: 10.1038/nm.3870. Epub Jun. 1, 2015.

Smith et al., Comparison of biosequences. Adv Appl Math. Dec. 1981;2(4):482-9. doi: 10.1016/01968858(81)90046-4.

Song et al., DMSO Increases Mutation Scanning Detection Sensitivity of High-Resolution Melting in Clinical Samples. Clin Chem. Nov. 2015; 61(11):1354-62. doi: 10.1373/clinchem.2015.245357. Epub Oct. 2, 2015.

Song et al., Elimination of unaltered DNA in mixed clinical samples via nuclease-assisted minor-allele enrichment. Nucleic Acids Res. Nov. 2, 2016; 44(19):e146. Epub Jul. 18, 2016.

Ståhlberg et al., Simple, multiplexed, PCR-based barcoding of DNA enables sensitive mutation detection in liquid biopsies using sequencing. Nucleic Acids Res. Jun. 20, 2016; 44(11):e105. doi: 10.1093/nar/gkw224. Epub Apr. 7, 2016.

Steger, Thermal denaturation of double-stranded nucleic acids: prediction of temperatures critical for gradient gel electrophoresis and polymerase chain reaction. Nucleic Acids Res. Jul. 25, 1994;22(14):2760-8.

Sun et al., Detection of tumor mutations in the presence of excess amounts of normal DNA. Nat Biotechnol. Feb. 2002;20(2):186-9.

Suspène et al., Inversing the natural hydrogen bonding rule to selectively amplify GC-rich ADAR-edited RNAs. Nucleic Acids Res. Jul. 2008;36(12):e72. doi: 10.1093/nar/gkn295. Epub May 30, 2008.

Tang et al., Characterization of mitochondrial DNA heteroplasmy using a parallel sequencing system. Biotechniques. Apr. 2010;48(4):287-96. doi:10.2144/000113389.

Taniguchi et al., Quantitative detection of EGFR mutations in circulating tumor DNA derived from lung adenocarcinomas. Clin Cancer Res. Dec. 15, 2011; 17(24):7808-15. doi: 10.1158/1078-0432.CCR-11-1712. Epub Oct. 5, 2011.

Thierry et al., Clinical validation of the detection of KRAS and BRAF mutations from circulating tumor DNA. Nat Med. Apr. 2014; 20(4):430-5. doi: 10.1038/nm.3511. Epub Mar. 23, 2014.

Thomas et al., High-throughput oncogene mutation profiling in human cancer. Nat Genet. Mar. 2007;39(3):347-51. Epub Feb. 11, 2007. Erratum in: Nat Genet. Apr. 2007;39(4):567. Macconnaill, Laura E [corrected to MacConaill, Laura].

Thomas et al., Sensitive mutation detection in heterogeneous cancer specimens by massively parallel picoliter reactor sequencing. Nat Med. Jul. 2006;12(7):852-5. Epub Jun. 25, 2006. Erratum in: Nat Med. Oct. 2006;12(10):1220.

Thress et al., Acquired EGFR C797S mutation mediates resistance to AZD9291 in non-small cell lung cancer harboring EGFR T790M. Nat Med. Jun. 2015; 21(6):560-2. doi: 10.1038/nm.3854. Epub May 4, 2015.

Till et al., High-throughput discovery of rare human nucleotide polymorphisms by Ecotilling. Nucleic Acids Res. Aug. 7, 2006;34(13):e99. Erratum in: Nucleic Acids Res. 2006;34(18):5352.

Tong et al., Diagnostic developments involving cell-free (circulating) nucleic acids. Clin Chim Acta. Jan. 2006;363(1-2):187-96. Epub Aug. 26, 2005.

Tsang et al., Circulating nucleic acids in plasma/serum. Pathology. Apr. 2007;39(2):197-207.

Vámosi et al., The helix-coil transition of DNA duplexes and hairpins observed by multiple fluorescence parameters. Biochemistry. Oct. 6, 1998;37(40):14300-16.

Varley et al., Bisulfite Patch PCR enables multiplexed sequencing of promoter methylation across cancer samples. Genome Res. Sep. 2010; 20(9):1279-87. doi: 10.1101/gr.101212.109. Epub Jul. 13, 2010.

(56) References Cited

OTHER PUBLICATIONS

Varley et al., Nested Patch PCR enables highly multiplexed mutation discovery in candidate genes. Genome Res. Nov. 2008; 18(11):1844-50. doi: 10.1101/gr.078204.108. Epub Oct. 10, 2008.

Varley et al., Nested Patch PCR for highly multiplexed amplification of genomic loci. Cold Spring Harb Protoc. Jul. 2009; 2009(7):pdb.prot5252. doi: 10.1101/pdb.prot5252.

Vestheim et al., Blocking primers to enhance PCR amplification of rare sequences in mixed samples—a case study on prey DNA in Antarctic krill stomachs. Front Zool. Jul. 20, 2008;5:12. doi: 10.1186/1742-9994-5-12.

Völker et al., High-resolution calorimetric and optical melting profiles of DNA plasmids: resolving contributions from intrinsic melting domains and specifically designed inserts. Biopolymers. Sep. 1999;50(3):303-18. Erratum in: Biopolymers Jan. 2000;53(1):112.

Wagner et al., Challenges for biomarkers in cancer detection. Ann N Y Acad Sci. Jun. 2004;1022:9-16.

Walker et al., Strand displacement amplification—an isothermal, in vitro DNA amplification technique. Nucleic Acids Res. Apr. 11, 1992;20(7):1691-6.

Walsh et al., Preferential PCR amplification of alleles: mechanisms and solutions. PCR Methods Appl. May 1992;1(4):241-50.

Wang et al., Determination of human beta(2)-adrenoceptor haplotypes by denaturation selective amplification and subtractive genotyping. Am J Pharmacogenomics. 2001;1(4):315-22.

Wetmur, DNA probes: applications of the principles of nucleic acid hybridization. Crit Rev Biochem Mol Biol. 1991;26(3-4):227-59.

Wittwer et al., High-resolution genotyping by amplicon melting analysis using LCGreen. Clin Chem. Jun. 2003;49(6 Pt 1):853-60.

Wittwer et al., The LightCycler: a microvolume multisample fluorimeter with rapid temperature control. Biotechniques. Jan. 1997;22(1):176-81.

Wong et al., Multiplex Illumina sequencing using DNA barcoding. Curr Protoc Mol Biol. 2013;Chapter 7:Unit 7.11 . . . doi: 10.1002/0471142727.mb0711s101.

Worm et al., In-tube DNA methylation profiling by fluorescence melting curve analysis. Clin Chem. 2001;47(7):1183-9.

Wu et al., Continuously tunable nucleic acid hybridization probes. Nat Methods. Dec. 2015; 12(12):1191-6. doi: 10.1038/nmeth.3626. Epub Oct. 19, 2015.

Xu et al., Dual primer emulsion PCR for next-generation DNA sequencing. Biotechniques. May 2010;48(5):409-12. doi: 10.2144/000113423.

Yang et al., Nucleoside analogs to manage sequence divergence in nucleic acid amplification and SNP detection. Nucleic Acids Res. Jul. 6, 2018; 46(12):5902-5910. doi: 10.1093/nar/gky392.

Yeung et al., Enzymatic mutation detection technologies. Biotechniques. May 2005;38(5):749-58.

Yongliang et al., p53 gene mutations in non-small cell lung cancer detected by polymerase chain reaction single-strand conformation polymorphism analysis. Chin Med Sci J. Sep. 1999;14(3):134-7.

Yu et al., Base-resolution analysis of 5-hydroxymethylcytosine in the mammalian genome. Cell. Jun. 8, 2012; 149(6):1368-80. doi: 10.1016/j.cell.2012.04.027. Epub May 17, 2012.

Zhang et al., An amplification and ligation-based method to scan for unknown mutations in DNA. Hum Mutat. Aug. 2002;20(2):139-47.

Zhou et al., Closed-tube genotyping with unlabeled oligonucleotide probes and a saturating DNA dye. Clin Chem. Aug. 2004;50(8):1328-35. Epub May 27, 2004.

Zuo et al., Application of COLD-PCR for improved detection of KRAS mutations in clinical samples. Mod Pathol. Aug. 2009;22(8):1023-31. doi:10.1038/modpathol.2009.59. Epub May 8, 2009.

Ladas et al. Multiplexed Elimination of Wild-Type DNA and High-Resolution Melting Prior to Targeted Resequencing of Liquid Biopsies. Clin Chem. 2017;63(10):1605-1613. doi:10.1373/clinchem.2017.272849.

Owczarzy et al., Predicting stability of DNA duplexes in solutions containing magnesium and monovalent cations. Biochemistry. May 13, 2008;47(19):5336-53. doi: 10.1021/bi702363u. Epub Apr. 19, 2008.

Roschewski et al., Circulating tumour DNA and CT monitoring in patients with untreated diffuse large B-cell lymphoma: a correlative biomarker study. Lancet Oncol. May 2015; 16(5):541-9. doi: 10.1016/S1470-2045(15)70106-3. Epub Apr. 1, 2015. Author Manuscript. 19 pages.

\* cited by examiner

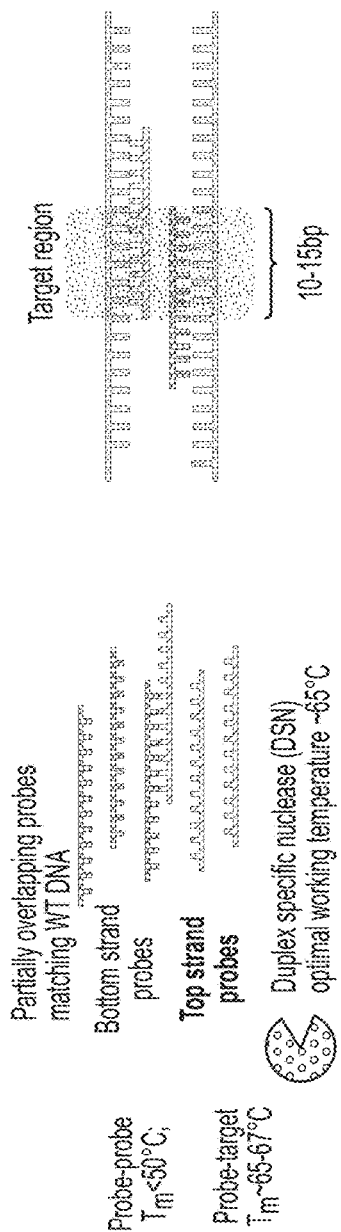
FIG. 1A
FIG. 1B
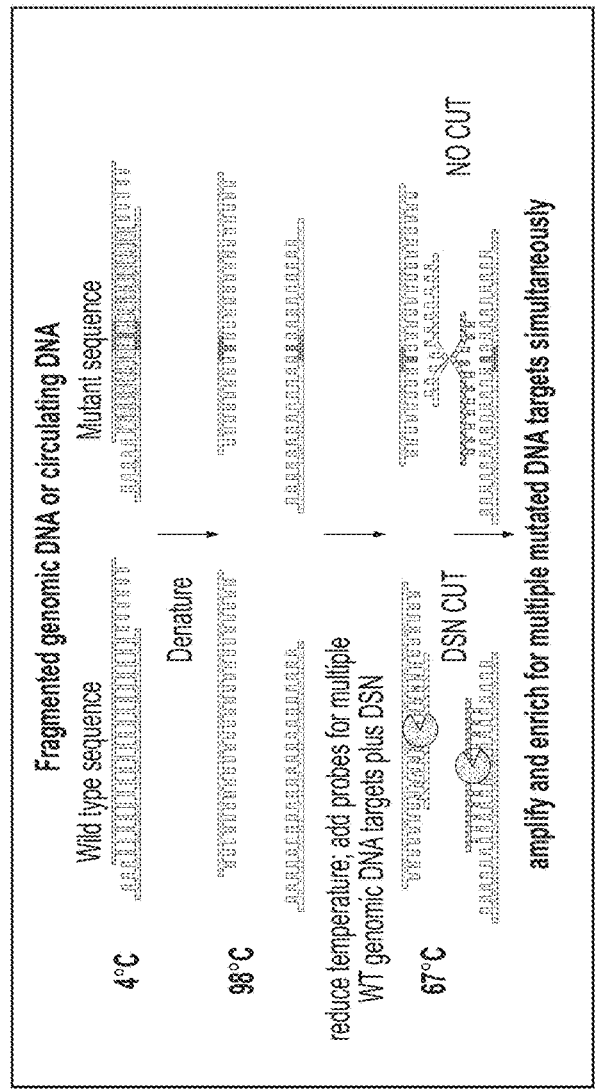
FIG. 1C

COMPOSITIONS AND METHODS FOR MOLECULAR BARCODING OF DNA MOLECULES PRIOR TO MUTATION ENRICHMENT AND/OR MUTATION DETECTION

RELATED APPLICATIONS

This application is a national stage filing under 35 U.S.C. § 371 International Patent Application, PCT/US2017/065747, filed Dec. 12, 2017, which claims the benefit of U.S. provisional application No. 62/433,071, filed on Dec. 12, 2016, U.S. provisional application No. 62/502,128, filed on May 5, 2017, and U.S. provisional application No. 62/522,856, filed on Jun. 21, 2017, the entire disclosures of which are incorporated by reference herein.

BACKGROUND OF THE INVENTION

Low-level tumor somatic DNA mutations can have profound implications for development of metastasis, prognosis, choice of treatment, follow-up or early cancer detection. Unless effectively detected, these low-level mutations can misinform patient management decisions or become missed opportunities for personalized medicine. Next generation sequencing (NGS) technologies reveal prevalent somatic mutations, yet they 'lose steam' when it comes to detecting low-level DNA mutations in tumors with clonal heterogeneity, or in bodily fluids during 'liquid biopsy', and their integration with clinical practice is not straightforward. For mutations at an abundance of ~2-5% or less, both NGS and the methods required to prepare DNA for NGS generate false positives ('noise') independent of sequencing depth and hinder personalized clinical decisions based on mutational profiling. Recent enhancements employing single molecule barcoding enable NGS to reduce noise and detect 'ultra-rare mutations'. However, these approaches invariably diminish NGS throughput capability and increase expense as they require numerous reads per sequence (e.g. >5,000-20,000× Mean Coverage).

SUMMARY OF THE INVENTION

The present disclosure relates to novel methods for retaining both throughput breadth and sequencing depth. Accordingly, some aspects of the disclosure provide a method of determining original abundance of mutant alleles of target nucleic acid in a sample of genomic DNA. In some embodiments, the method comprises: providing a sample of double-stranded genomic DNA fragments anticipated to comprise mutant alleles of target nucleic acid and wild-type alleles of the target nucleic acid, wherein each terminus of the genomic DNA fragments is attached to a unique double stranded barcode and a double stranded common sequence tag, wherein the common sequence tag is located upstream of the unique barcode; amplifying a portion of the double-stranded genomic DNA fragments using primers that are complementary to the common sequence tag; enriching in the amplified portion the mutant alleles of the target nucleic acids relative to the wild-type alleles of the target nucleic acids; obtaining a measure of total number of unique barcodes associated with mutant target nucleic acid sequence in the enriched portion; and, obtaining a measure of total number of unique barcodes associated with the sample. The original abundance of the mutant target nucleic acid in the sample of genomic DNA is represented by the ratio of the total number of unique barcodes associated with mutant target nucleic acid sequence to the total number of unique barcodes associated with the sample.

In some embodiments, the total number of unique barcodes associated with the sample is the total number of unique barcodes associated with mutant and wild-type target nucleic acid sequence in the enriched portion In some embodiments when the mutant alleles are enriched relative to the wild-type alleles, wild-type alleles become difficult to detect. In some embodiments, to provide additional information towards quantification of the original mutation abundance, in addition to applying mutation enrichment, a control sample is treated without mutation enrichment, as an un-enriched control sample in parallel. The combined information from both samples (mutation enriched sample and un-enriched control sample) provide additional information as compared to only the mutation enriched sample alone. For example, the unenriched control sample may provide a more accurate estimate of uniquely-barcoded wild-type alleles, while the mutation enriched sample may provide the most accurate estimate of uniquely-barcoded mutant alleles. By combining the information from both enriched sample and un-enriched control sample, it may be possible to more accurately quantify original mutation abundance than by screening either the mutant enriched sample or the un-enriched control sample alone.

Accordingly, a method of determining original abundance of mutant alleles of target nucleic acid in a sample of genomic DNA further comprises obtaining a measure of total number of unique barcodes associated with wild-type target nucleic acid sequence in an un-enriched control sample, wherein the total number of unique barcodes associated with the sample is the sum of the total number of unique barcodes associated with mutant target nucleic acid sequence in the enriched portion and the total number of unique barcodes associated with wild-type target nucleic acid sequence in an un-enriched control sample. In some embodiments, a method of determining original abundance of mutant alleles of target nucleic acid in a sample of genomic DNA further comprises amplifying the double-stranded genomic DNA fragments in the un-enriched control sample using primers that are complementary to common sequence tags prior to obtaining a measure of total number of unique barcodes associated with wild-type target nucleic acid sequence in the un-enriched control sample. Therefore, in some embodiments, an un-enriched control sample is an aliquot of the sample that is processed in parallel to the sample that is enriched for mutant alleles of the target nucleic acids relative to the wild-type alleles of the target nucleic acids. Accordingly, in some embodiments, double-stranded genomic DNA fragments in a sample and unenriched control sample are attached to unique double-stranded barcodes in separate reactions. In some embodiments, double-stranded genomic DNA fragments in a sample and unenriched control sample are amplified using primers that are complementary to a common sequence tag in separate reactions.

In some embodiments, an un-enriched control sample is an aliquot of an amplified portion.

In some embodiments, the number of sequencing reads used to obtain the total number of unique barcodes associated with mutant target nucleic acid sequence in the enriched portion is less than or equal to 1 million. In some embodiments, the number of sequencing reads used to obtain the total number of unique barcodes associated with wild-type target nucleic acid sequence in the un-enriched control sample is less than or equal to 1 million. In some embodiments, the number of sequencing reads used to obtain the total number of unique barcodes associated with mutant target nucleic acid sequence in the enriched portion is equal to the number of sequencing reads used to obtain the total number of unique barcodes associated with wild-type target nucleic acid sequence in the un-enriched control sample. In some embodiments, the enriched portion and the un-enriched control sample are sequenced in the same sequencing reaction. Sample indices can be used to identify the origin of DNA fragments when the enriched portion and the amplified control sample are sequenced in the same sequencing reaction. Accordingly, in some embodiments, before sequencing, the DNA fragments of the enriched portion are attached to a first sample-index and the DNA fragments of the un-enriched amplified control sample are attached to a second sample-index, wherein the first sample-index is different from the second sample-index. In some embodiments, the sample is divided prior to amplification and a first sample index is attached to a first portion of the sample which will be later amplified and enriched and a second sample index is provided to a second portion of the sample will is the control sample, prior to sequencing (with or without amplification).

In some embodiments, the enriched portion and the un-enriched control sample are sequenced in separate sequencing reactions.

In some embodiments, a method of determining original abundance of mutant alleles of target nucleic acid in a sample of genomic DNA involves target enrichment. Accordingly, some embodiments of any one of the methods of determining original abundance of mutant alleles of target nucleic acid in a sample of genomic DNA further comprises enriching both the mutant target nucleic acids and wild-type target nucleic acids relative to total nucleic acids in the sample. In some embodiments, enriching the mutant target nucleic acids and wild-type target nucleic acids relative to total nucleic acids in the sample comprises contacting the sample with one or more probes that specifically bind target nucleic acids. In some embodiments, one or more probes are bound to a solid substrate. In some embodiments, the solid substrate comprises beads.

In some embodiments, enrichment of mutant target nucleic acids and wild-type target nucleic acids relative to total nucleic acids in the sample is performed by multiplex PCR. The present invention describes novel methods for performing multi-stage multiplex PCR optionally incorporating molecular barcodes at one of the stages, and optionally performing mutation enrichment, and producing a sequencing-ready sample.

In some embodiments, the enriching the mutant target nucleic acids and wild-type target nucleic acids relative to total nucleic acids in the sample involves amplifying the double-stranded genomic DNA fragments in the sample using a first and second primer. In some embodiments, the first primer is complementary to the double stranded common sequence tag, and the second primer is a nested gene-specific primer comprising a sequence tag that is different from the double-stranded common sequence tag. In some embodiments, the sequence tag on a second primer that is a nested gene-specific primer is common for the same target, but different for different targets. In some embodiments, the enriching the mutant target nucleic acids and wild-type target nucleic acids relative to total nucleic acids is performed after the amplifying of the double-stranded genomic DNA fragments using primers that are complementary to the common sequence tag. In some embodiments, the amplifying the double-stranded genomic DNA fragments in the sample using a first and second primer is performed for 5-15 cycles. In some embodiments, the first primer comprises a sequencing adapter (e.g., an Illumina adapter).

Some embodiments of any one of the methods of determining original abundance of mutant alleles of target nucleic acid in a sample of genomic DNA further comprises fragmenting genomic DNA to form the double-stranded genomic DNA fragments. In some embodiments, the genomic DNA is fragmented using Shearase or any other DNA-ase type of enzyme that digests DNA randomly. In some embodiments, enzymatic end-repairing of the DNA fragments to obtain blunt ended 5' containing double-stranded DNA is done after fragmentation (e.g., by an enzyme).

In some embodiments, any one of the methods disclosed herein does not include obtaining a measure of total number of barcodes that are associated with non-target mutant nucleic acids or non-target wild-type nucleic acids in the enriched portion.

In some embodiments, the method further comprises obtaining sequences of the mutant target nucleic acids and wild-type target nucleic acids in the enriched sample.

In some embodiments of any one of the methods of determining original abundance of mutant alleles of target nucleic acid as disclosed herein, the double-stranded genomic DNA fragments are 40-200 bp in length. In some embodiments, the unique barcode is 8-14 bp in length. In some embodiments, the common tag is 16-40 bp in length.

Some embodiments of any one of the methods of determining original abundance of mutant alleles of target nucleic acid in a sample of genomic DNA further comprises attaching the double-stranded genomic DNA fragments to the unique double-stranded barcodes. In some embodiments, attaching of double-stranded fragments of genomic DNA to the unique barcodes is performed at a ratio of $10^7$-$10^9$ unique barcodes to 100 ng double-stranded genomic DNA fragments present in the sample. In some embodiments, wherein the attaching comprises starting from a single-stranded barcode, synthesizing the opposite strand of the single-stranded barcode using an extension reaction to form a double stranded barcode, and then ligating to an end of the double-stranded genomic DNA fragment. In some embodiments, the attaching of barcodes comprises PCR using oligonucleotide primers, wherein each oligonucleotide primer comprises a common tag portion, a unique barcode portion, and a target-specific portion. In some embodiments, 1-6 cycles of PCR are used to attach barcodes using PCR.

In some embodiments of any one of the method of determining original abundance of mutant alleles of target nucleic acid in a sample of genomic DNA, the barcoded DNA fragments are amplified using PCR or COLD-PCR. In some embodiments, 3-30 cycles of PCR or COLD-PCR are performed for amplifying the barcoded DNA fragments.

Any one of the methods disclosed herein can be performed on a solid substrate. Accordingly, in some embodiments of any one of the methods disclosed herein, the common tag is biotinylated. In some embodiments, the double-stranded genomic DNA fragments attached to barcodes and common tags are bound to streptavidin-beads.

In some embodiments of any one of the methods disclosed herein, the genomic DNA is obtained from a biological sample. In some embodiments, the biological sample is selected from tissue, blood, plasma, serum, urine, saliva, and cerebrospinal fluid. In some embodiments, the tissue sample is a tumor biopsy. In some embodiments, the biological sample comprises circulating cell-free DNA.

In some embodiments of any one of the methods of determining original abundance of mutant alleles of target nucleic acid in a sample of genomic DNA, following incorporation of molecular barcodes to DNA molecules, the mutant target nucleic acid in the amplified portion is enriched by 2-300 fold relative to the wild-type target nucleic acid in the amplified portion. In some embodiments, the enriching the mutant alleles of the target nucleic acids in the amplified portion relative to the wild-type alleles of the target nucleic acids in the amplified portion comprises subjecting the amplified portion to one or more of the following: Nuclease-assisted Minor-allele Enrichment using Probe Overlap (NaME-PrO), Coamplification at Lower Denaturation temperature-PCR (COLD-PCR), Improved and Complete Enrichment COLD-PCR (ice-COLD-PCR), Temperature-Tolerant-ice-COLD-PCR (TT-ice-COLD-PCR), toehold PCR, blocker-PCR using locked nucleic acids (LNA), peptide nucleic acids (PNA or XNA), or blockers with other modified nucleotides, CRISP-R-mediated mutation enrichment by selecting mutated alleles or removing wild-type alleles and Differential Strand Separation at Critical Temperature (DiSSECT).

In some embodiments, the NaMe-PrO comprises (a) preparing an amplification reaction mixture comprising the double-stranded mutant and wild-type target nucleic acids, a thermostable double strand-specific nuclease (DSN), PCR amplification components, and a pair of oligonucleotide probes, one of which is complementary to the wild-type nucleic acid top strand and the other is complementary to the wild-type nucleic acid bottom strand, wherein the probes overlap each other by 10-15 probes such that the overlap coincides with the target region;

(b) subjecting the reaction mixture to a denaturing temperature to permit denaturation of the wild-type nucleic acid and the mutant target nucleic acid;

(c) reducing the temperature to permit hybridization of the probes to their corresponding sequences on the wild-type and mutant target nucleic acids thereby forming complementary wild-type-probe duplexes, wherein the DSN cleaves the complementary wild-type-probe duplexes but not the partially complementary target mutant-probe duplexes; and (d) subjecting the reaction mixture to an amplification condition thereby enriching the uncleaved mutant target nucleic acid relative to the cleaved wild-type nucleic acid.

In some embodiments of any of the methods that utilize NaMe-Pro, the target region that coincides with the overlap of the probes comprises more than one mutation. In some embodiments, the probes have a 3'-terminal polymerase block. In some embodiments, to avoid identifying SNPs in the genome around the mutation site, the NaMe-Pro probes are designed so that they are complementary to SNPs near target mutations.

In some embodiments, the COLD-PCR comprises (a) denaturing the double-stranded mutant and wild-type target nucleic acids by subjecting the double-stranded target mutant and wild-type nucleic acids to a first denaturing temperature that is above the melting temperature of the wild-type nucleic acid;

(b) forming a target mutant/wild-type strand duplex;

(c) denaturing said mutant/wild-type strand duplex by subjecting the nucleic acid amplified portion to a critical temperature (Tc) that is below the Tm of the wild-type nucleic acids;

(d) annealing a primer pair to the mutant and wild-type target nucleic acid strands; and (e) extending said primer pair so as to enrich said mutant target sequence relative to said wild-type strand.

In some embodiments of methods disclosed herein that utilize COLD-PCR, (b) and (c) of COLD-PCR (as described above) are repeated 1-19 times before performing (d). In some embodiments, (a) to (e) are repeated 1-29 times.

In some embodiments, ice-COLD-PCR comprises (a) exposing the mutant and wild-type target nucleic acids to a reference sequence that is complementary the target sequence;

(b) denaturing the double-stranded target mutant and wild-type nucleic acids by subjecting the double-stranded mutant and wild-type target nucleic acids to a first denaturing temperature that is above the melting temperature of the wild-type nucleic acid;

(c) forming a target mutant/reference strand and target wild-type/reference strand duplexes;

(d) denaturing said mutant/reference strand duplex by subjecting the nucleic acid sample to a critical temperature (Tc) that is below the Tm of the wild-type/reference duplex;

(d) annealing a primer pair to the mutant and wild-type target nucleic acid strands; and (e) extending said primer pair so as to enrich said mutant target sequence relative to said wild-type target nucleic acid.

In some embodiments, TT-ice-COLD-PCR comprises (a) exposing the mutant and wild-type target nucleic acids to a reference sequence that is complementary the target sequence;

(b) denaturing the double-stranded target mutant and wild-type target nucleic acids by subjecting the double-stranded target mutant and wild-type nucleic acids to a denaturing temperature that is above the melting temperature of the wild-type nucleic acid;

(c) forming a target mutant/reference strand and target wild-type/reference strand duplexes;

(d) denaturing said mutant/reference strand duplex by subjecting the nucleic acid sample to a first critical temperature (Tc) that is below the Tm of the wild-type/reference duplex;

(e) annealing a primer pair to the mutant and wild-type target nucleic acid strands;

(f) extending said primer pair so as to enrich said mutant target nucleic acid relative to said wild-type target nucleic acid; and (f) repeating steps (d) to (f) at least once at a second Tc which is above the first Tc.

In some embodiments, DiSSECT comprises:

(a) allowing mutant and wildtype target nucleic acids to bind to complementary probes which are immobilized to beads, wherein the probes resemble the wild-type nucleic acids;

(b) denaturing the target mutant/probe duplex by subjecting the nucleic acid sample to a critical temperature such that the wild-type/probe duplex does not denature;

(c) collecting the eluate from the beads; and (d) repeating at least once (a)-(c) using beads on which the probes are unbound to any nucleic acid.

Any of the methods disclosed herein can also be applied to samples in which the abundance of more than one mutation is determined. Accordingly, any one of the methods of determining original abundance of mutant alleles of target nucleic acid in a sample of genomic DNA further comprises determining the original abundance of one or more additional mutant alleles of target nucleic acids at different loci on the genomic DNA. In some embodiments of methods to determine abundance of one or more additional mutant alleles of target nucleic acids, the mutant alleles of the target nucleic acids are enriched relative to wild-type alleles of the target nucleic acids by subjecting the amplified portion to multiplexed NaME-PrO. In some embodiments, the multiplexed NaME-PrO uses overlapping probe pairs in parallel reactions, wherein each parallel reaction uses a distinct pair of overlapping probes, such that the totality of overlapping probe pairs span a contiguous region of genomic DNA of interest. In some embodiments, the multiplexed NaME-PrO uses continuous and non-overlapping probe pairs in parallel reactions, wherein each parallel reaction uses a distinct pair of non-overlapping probes, such that the totality of non-overlapping probe pairs span a contiguous region of genomic DNA of interest.

In some aspects, provided herein is a method of determining disease diagnosis or prognosis in a subject, the method comprising determining original abundance of a mutant target nucleic acid in a sample of genomic DNA according to any one of the methods disclosed herein. In some embodiments, the determining is repeated in two or more genomic DNA samples obtained from a subject over a period of time, and wherein an increase in original abundance of the target mutant nucleic acids in the sample over time is indicative of a worsening diagnosis or prognosis in the subject.

In some aspects, provided herein is a method of determining efficacy of a therapeutic treatment in a subject, the method comprising determining original abundance of a mutant target nucleic acid in a sample of genomic DNA according to any one of the methods disclosed herein. In some embodiments, the determining is repeated in genomic DNA samples obtained from a subject before and after treatment, and wherein a decrease in original abundance of the target mutant nucleic acids in the sample after treatment is indicative of therapeutic efficacy in the subject. In some embodiments, the determining is repeated in 2-10 genomic DNA samples obtained over a period of time. In some embodiments, the determining is repeated over a period of time of 2 months to 2 years.

In some aspects, provided herein is a method of obtaining a fingerprint of mutations associated with a disease, the method comprising determining original abundance of mutant alleles of target nucleic acids of a plurality of mutations according to any one of the methods disclosed herein. In some embodiments, the determining is performed on one or more samples of genomic DNA obtained from one or more subjects suffering from the disease.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein. It is to be understood that the data illustrated in the drawings in no way limit the scope of the disclosure.

FIG. 1 describes Nuclease-assisted Minor-allele Enrichment using PRobe-Overlap (NaME-PrO). FIG. 1A shows partially overlapping oligonucleotide probes are included in excess molar ratio as compared to target DNA; and duplex specific nuclease (DSN). FIG. 1B describes NaMe-PrO. Probes are designed to bind the WT sequence of top and bottom target DNA strands. The overlap region of the probes defines the DNA region targeted for mutation enrichment. FIG. 1C shows a NaME-PrO workflow; following fragmented genomic DNA denaturation, the excess probes bind their targets. Addition of DSN generates preferential digestion at double stranded regions defined by the probes, but not at mutation-caused mismatches. Numerous targeted sites can be targeted simultaneously in this manner. Subsequent amplification enhances DNA target strands that escape DSN digestion, thereby enriching for mutated DNA by several hundred-fold.

FIG. 7 describes comprehensive sequencing of cfDNA from adult patients with metastatic cancer.

FIG. 8 describes multiplexed mutation enrichment via NaME-PrO applied to clinical samples (Song et al 2016).

FIG. 10 describes NaME-PrO application for enriching multiple mutations along tumor suppressor genes.

DETAILED DESCRIPTION

Provided herein is a transformative technology that retains both high throughput (breadth) and sequencing depth for mutation analysis. The disclosed technology combines mutation enrichment methods (e.g., NaME-PrO or COLD-PCR) with a novel use of molecular barcoding, to provide strict enumeration of original mutation abundance for all mutant sequences following their enrichment. Provided methods permit converting rare mutations to high abundance mutations, boosting confidence in their detection and circumventing the need for repeated and wasteful sequence reads during NGS. This enables NGS to reliably identify low-level alterations while retaining low cost and high throughput capabilities. Provided methods allow the quantification of the original mutation frequency in a sample (i.e., abundance of mutation frequency in a sample before it is processed for mutation enrichment), which was not previously possible.

There are several advantages of the disclosed methods over current state of the art. Exemplary advantages of the disclosed methods are discussed herein. For example, mutations down to 0.1% mutation abundance are clinically significant in heterogeneous tumors, circulating DNA and other clinical samples. Clinically actionable mutations in tumors or circulating DNA often exist at levels ≤0.1% which falls well below the ability of existing targeted re-sequencing technology. Provided methods allow quantification of mutation abundance after mutation enrichment so that detection is possible. Furthermore, methods disclosed herein are compatible with sequencing methods. The disclosed methods allow identification and quantification of mutations with low abundances with the current sequencing technologies available and in the current sample preparation framework.

Figure 11:
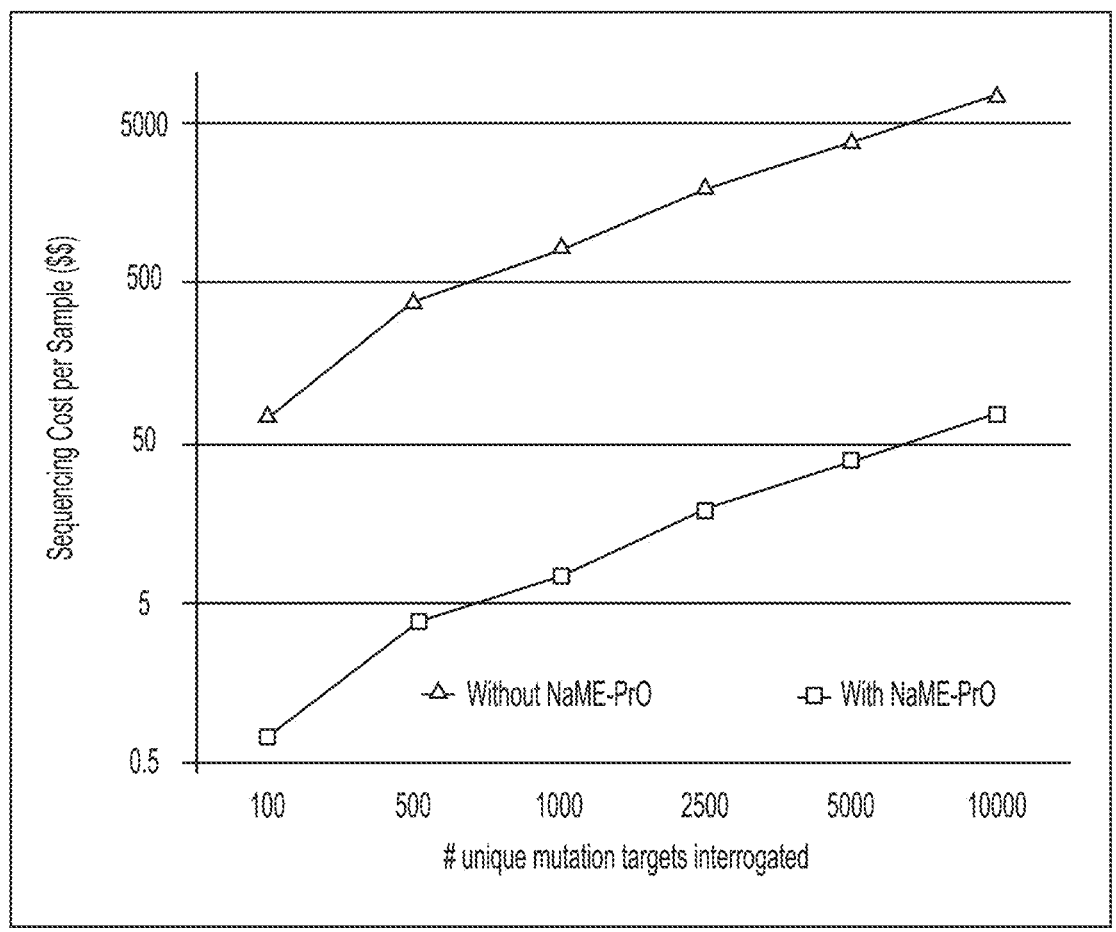
FIG. 11 shows sequencing cost (Illumina MiSeq) as a function of number of unique DNA mutation targets interrogated. Assumptions: 100% pass filter unique reads, uniform amplicon generation, one hotspot per amplified DNA fragment, $1,924 per lane (Broad SSF pricing). Sample preparation costs not included in this calculation. NaME-PrO application itself costs $17.3 for a 1000-target reaction including 2,000 unlabeled probes plus enzyme.

In some embodiments, provided mutation enrichment methods (e.g., NaME-PrO) enable single tube enrichment of mutations that enable NGS-based detection down to extremely low abundances without requiring a substantial increase in the number of sequence reads as compared to high-level mutations. This may be achieved by pre-enriching the sample for mutations over all targets, prior to entering the NGS stage, thus converting low-level mutations to clonal mutations which are detectable with few sequence reads, and thereby reducing time and cost. FIG. 11 demonstrates an exemplary major reduction in cost as a function of the sequenced target size using the Illumina MiSeq as an example. The method is applicable to all platforms. However, the modest cost of MiSeq instrument makes it accessible to many groups or labs that do not have access to a high-end facility.

Reliability of mutant identification is another advantage of the methods disclosed herein. Even though molecular barcoding technology and sophisticated filtering can distinguish the few genuine sequencing from noise, at high noise levels there is doubt calling 2-3 mutation reads amongst 100,000 WT reads. By increasing the allele fraction of mutations above the noise floor of NGS, errors associated with NGS can be overcome and reliability increased.

'Wild type target sequence' or 'wild type nucleic acid', used interchangeably herein, refers to a nucleic acid that is more prevalent in a nucleic acid sample than a corresponding target sequence (e.g., same region of gene but different nucleic acid sequence). The wild type sequence makes-up over 50% of the total wild type sequence+mutant target sequence in a Sample. The wild type sequence can be expressed at the RNA and/or DNA level 10×, 15×, 20×, 25×, 30×, 35×, 40×, 45×, 50×, 60×, 70×, 80×, 90× 100×, 150×, 200× or more than the target sequence. For example, a sample (e.g., blood sample, urine sample, tissue sample) may contain numerous normal cells and few cancerous cells. The normal cells contain wild-type alleles (non-mutant) sequences, while the small number of cancerous cells contain target sequences. As used herein, a 'wild type strand' refers to a single nucleic acid strand of a wild type sequence. The term 'wild-type' typically refers to the most common polynucleotide sequence or allele for a certain gene in a population. Generally, the wild-type allele will be obtained from normal cells.

The wild type sequence is about 13-2000 nucleotides long. In some embodiments, the wild type sequence is 20, 30, 40, 50, 60, 70, 80, 90, 100, 110, 120, 130, 140, 150, 160, 170, 180, 190, 200, 250, 300, 350, 400, 450, 500, 600, 700, 800, 900 or more nucleotides long. Wild type sequences will share at least 50%, 60%, 70%, 80%, 85%, 90%, 91%, 92%, 93%, 94%, 95%, 96%, 97%, 98%, 99% or more homology to the corresponding target sequence, but will differ by at least one nucleotide from the target sequence.

A 'target nucleic acid' or 'target sequence', used interchangeably herein, refers to a nucleic acid of interest (e.g., an allele). In some embodiments, a target nucleic acid has mutant alleles and wild-type alleles. In some embodiments, the target sequence makes-up less than 50% of the total amount of DNA (e.g., target sequence+non-target sequence) in a sample. Preferably the target sequence is expressed at the RNA and/or DNA level 1:10, 1:15, 1:20, 1:25×, 1:30, 1:35, 1:40, 1:45, 1:50, 1:60, 1:70, 1:80, 1:90, 1:100, 1:150, 1:200× or less than the non-target sequence. In some embodiments, the target sequence is a mutant allele. In some embodiments, the target sequence is a wild-type allele. For example, a sample (e.g., blood sample, urine sample, tissue sample) may contain numerous normal cells and few cancerous cells. The normal cells contain wild-type (i.e., non-mutant) sequences, while the small number of cancerous cells contain target mutant sequences. In some embodiments, the target sequence is repeat sequences that occur at large numbers in human genome (including but not limited to ALU elements, LINE elements, SINE elements, di-nucleotide repeats, tri-nucleotide repeats). As used herein, a "target strand" refers to a single nucleic acid strand of a target sequence. A target sequence may comprise coding regions, non-coding regions, both coding and non-coding regions, a whole gene or a portion or a gene.

In some embodiments, the target sequence is 13-2000 nucleotides long. In some embodiments, the target sequence is 20, 30, 40, 50, 60, 70, 80, 90, 100, 110, 120, 130, 140, 150, 160, 170, 180, 190, 200, 250, 300, 350, 400, 450, 500, 600, 700, 800, 900 or more nucleotides long. Target sequences share at least 50%, 60%, 70%, 80%, 85%, 90%, 91%, 92%, 93%, 94%, 95%, 96%, 97%, 98%, 99% or more homology to the corresponding wild type sequence, but differs by at least one nucleotide from the wild type sequence.

In some embodiments, target nucleic acids are enriched relative to total nucleic acids. In some embodiments, mutant target nucleic acids and wild-type target nucleic acids are enriched relative to total nucleic acids in a sample of double-stranded genomic DNA. Various methods of enriching target nucleic acids relative to total nucleic acids are known in the art and are contemplated herein. For example, target nucleic acids in a sample can be enriched by contacting the sample with one or more probes that specifically bind target nucleic acids. Probes that bind to target nucleic acids may be immobilized on a solid substrate (e.g., a bead) for easier separation of the target nucleic acids from the non-target nucleic acids. In some embodiments, probes bind to target nucleic acids by hybridization. In some embodiments, hybridization between probes and target nucleic acids is complete. In some embodiments, hybridization between probes and target nucleic acids is partial. For example, there may be 1 or more mismatches between a probe and target sequence. In some embodiments, only a part of a probe hybridizes with a target sequence.

Figure 12:
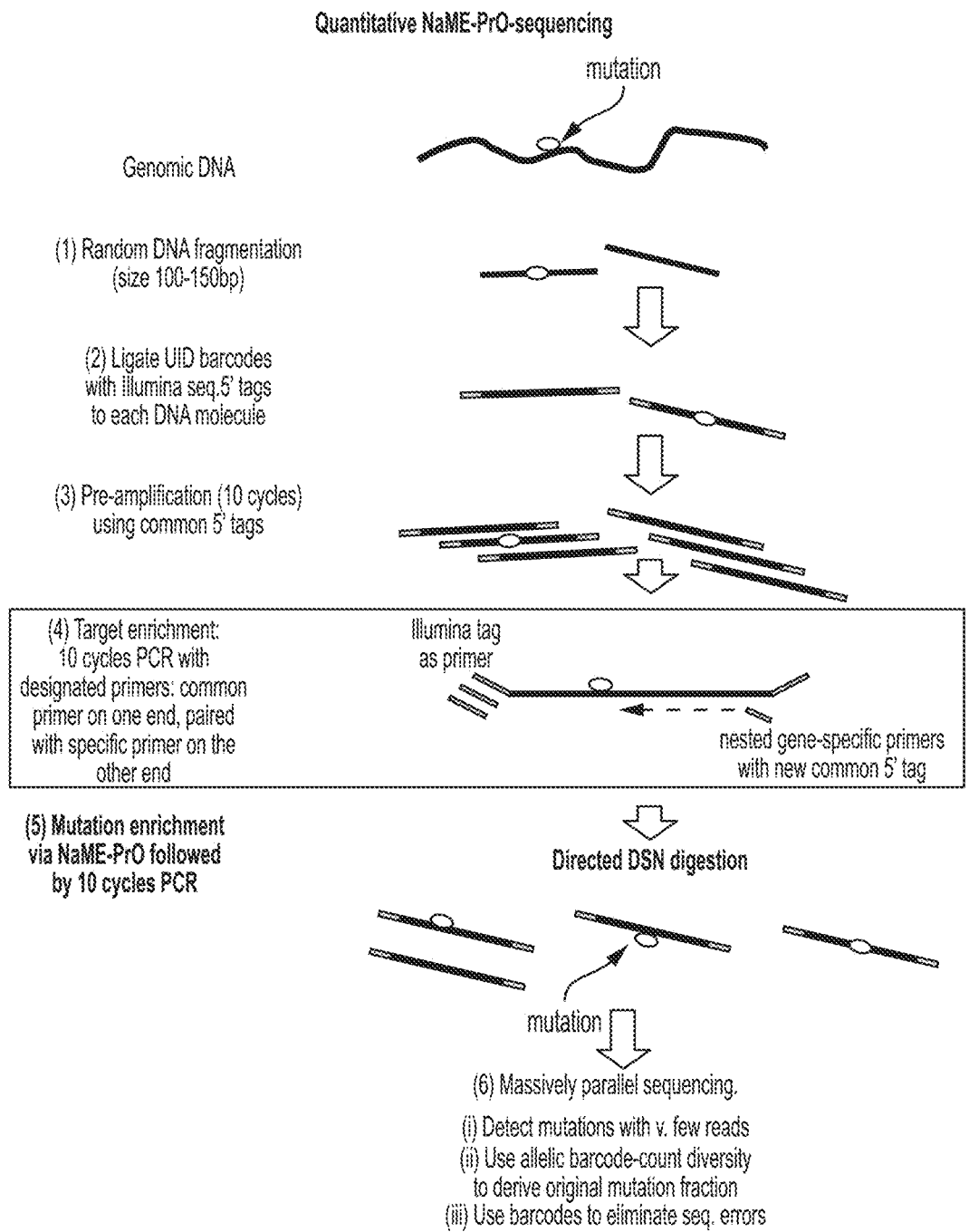
FIG. 12 shows attachment of molecular barcodes using ligation at the first step, followed by target enrichment using nested gene-specific primers on one end of each DNA target, plus the generic linker ligated in the first step.

Another method of target enrichment is shown in FIG. 12. Accordingly, in some embodiments, target enrichment is achieved using steps comprising amplification of a double-stranded DNA fragment using primers, at least one of which is a nested gene-specific primer. A 'nested gene-specific primer' is a primer than anneals to the product of amplification made using another set of primers to amplify a target region. In FIG. 12 for example, the nested gene-specific primer in step (4) nests such that it anneals to the product of a preceding pre-amplification step that uses primers that are complementary to the common sequence tags. Using the example in FIG. 12, the nested gene-specific primer of step (4) is nested relative to, or nests within, the primers complementary to the common sequence tags used in step (3). Nested primers may produce and amplification product of a shorter length than the product of the primers within which they are nested. Accordingly, a nested gene-specific primer may nest within a set of multiplexed primers such that it anneals to the product of the multiplexed amplification. Multiplexed primers within which a target-specific primer nests may be random primers, gene specific primers, or primers complementary to a common sequence tag. In some embodiments, an entire gene-specific primer anneals to a target sequence. In some embodiments, a portion of a gene-specific primer anneals to a target sequence. In some embodiments, a gene-specific primer anneals to a target sequence that is genomic DNA of a coding region, or genomic DNA of a non-coding region. In some embodiments, a gene-specific primer anneals to a target sequence that comprises a mutation or is adjacent (e.g., up to 30, 50, 100 or more nucleotides upstream or downstream) to a mutation. In some embodiments, a nested gene-specific primer comprises a sequence tag, that can be used for subsequent amplification using primers complementary to this sequence tag. A sequence tag on a gene-specific primer is different from double-stranded common sequence tag used in prior steps of determining original abundance of mutant alleles of target nucleic acid in a sample of genomic DNA, such that primers designed to anneal to a common sequence tag will not anneal to the sequence tag on a nested gene-specific primer, or primers designed to anneal to a sequence tag on a nested gene-specific primer will not anneal to a double-stranded common sequence tag. In some embodiments, a sequence tag on a gene-specific primer is different from sequence tags on gene-specific primers that anneal to other targets, such that primers designed to anneal to a sequence tag on a gene-specific primer targeting one target will not anneal to a sequence tag on a gene-specific primer targeting another target. In some embodiments of any one of the methods for target enrichment, a primer may comprise a sequencing adaptor that can be used during sequencing. In some embodiments, target enrichment achieved using amplification of a double-stranded DNA fragment using primers, at least one of which is a nested gene-specific primer, is performed for 2 to 20 cycles (e.g., 2 to 5, 4 to 18, 5 to 15 or 8 to 15 cycles).

In some embodiments, target nucleic acids (i.e., wild-type and mutant alleles of a target) are enriched 2 to 1000 times (e.g., 2 to 5, 2 to 10, 2 to 50, 2 to 100, 10 to 100, 50 to 200, 100 to 500, 200 to 1000 or 400 to 1000 times) relative to an unenriched sample.

'Target mutant sequence' or 'mutant target sequence' refers to a nucleic acid that is less prevalent in a nucleic acid sample than a corresponding wild type sequence. The target mutant sequence typically makes-up less than 50% of the total amount of wild type sequence+mutant sequence in a sample. The target mutant sequence may be expressed at the RNA and/or DNA level 1:10, 1:15, 1:20, 1:25×, 1:30, 1:35, 1:40, 1:45, 1:50, 1:60, 1:70, 1:80, 1:90, 1:100, 1:150, 1:200× or less than the wild type sequence. For example, a sample (e.g., blood sample) may contain numerous normal cells and few cancerous cells. The normal cells contain wild-type (non-mutant) alleles, while the small number of cancerous cells contain target mutant sequences. In some embodiments, the invention is directed to detecting fetal DNA in a nucleic acid sample obtained from a mother. In this embodiment, the target mutant sequence is the fetal DNA while the more prevalent mother DNA is the wild type sequence. As used herein, a target mutant sequence is meant to include fetal DNA obtained from a pregnant mother. A mutation may be in a coding region or a non-coding region of a genome. A mutation may be in a known location or site. In some embodiments, a mutation is unknown. In some embodiments, the exact location or a mutation is unknown. In some embodiments, a mutation and its site is unknown.

The target mutant sequence is about 13-2000 nucleotides long. In some embodiments, the target mutant sequence is 20, 30, 40, 50, 60, 70, 80, 90, 100, 110, 120, 130, 140, 150, 160, 170, 180, 190, 200, 250, 300, 350, 400, 450, 500, 600, 700, 800, 900 or more nucleotides long. Target mutant sequences share at least 50%, 60%, 70%, 80%, 85%, 90%, 91%, 92%, 93%, 94%, 95%, 96%, 97%, 98%, 99% or more homology to the corresponding wild type sequence, but differs by at least one nucleotide from the wild type sequence.

The term 'mutant' refers to a nucleotide change (i.e., a single or multiple nucleotide substitution, deletion, insertion, or methylation, or alteration in the number of polynucleotide repeats) in a nucleic acid sequence. A nucleic acid which bears a mutation has a nucleic acid sequence (mutant allele) that is different in sequence from that of the corresponding wild-type sequence. Herein, the term "mutant target nucleic acid" is used interchangeably with "mutant alleles of target nucleic acid." Similarly, the term "wild-type target nucleic acid" is used interchangeably with "wild-type alleles of target nucleic acid." The mutant alleles can contain between 1 and 500 nucleotide sequence changes. A mutant allele may have 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 200, 300, 400 or 500 nucleotide sequence changes compared to a corresponding wild-type allele. Typically, a mutant allele will contain between 1 and 10 nucleotide sequence changes, and more typically between 1 and 5 nucleotide sequence changes. The mutant allele will have 50%, 60%, 70%, 80%, 85%, 90%, 91%, 92%, 93%, 94%, 95%, 96%, 97%, 98%, 99% or more homology to the wild-type allele. Generally, the mutant allele will be obtained from diseased tissues or cells and is associated with a disease state.

As used herein, a 'region of interest' is a sequence that will be interrogated for variations such as clinically relevant mutations.

As used herein, the term "relative abundance" refers to the amount of the nucleic acid of the same type as compared to the amount of the total nucleic acid in a sample. For example, the relative abundance of a mutant nucleic acid in a sample may be defined as the percentage of the abundance of the mutant nucleic acid to the total number of nucleic acid corresponding to the target sequence in which the mutations lies, which includes both mutant and wild-type nucleic acid for that target sequence.

'Enriching a mutant target sequence' refers to increasing the amount of a mutant target sequence and/or increasing the ratio of mutant target sequence relative to the corresponding wild type sequence in a sample. For example, where the ratio of mutant sequence to wild type sequence is initially 5% to 95% in a sample, the mutant sequence may be preferentially amplified in an amplification reaction so as to produce a ratio of 70% mutant sequence to 30% wild type sequence. Thus, there is a 14 fold enrichment of the mutant sequence relative to the wild type sequence in this hypothetical example. Generally, enrichment of a mutant target sequence results in a 2× to 200× increase in the mutant target sequence relative to the wild type sequence prior to enrichment. The enrichment of the mutant target sequence is at least a 2×, 3×, 4×, 5×, 6×, 7×, 8×, 9×, 10×, 15×, 20×, 25×, 30×, 35×, 40×, 45×, 50×, 60×, 70×, 80×, 90× 100×, 150×, 200× or more fold enrichment. Enrichment of a mutant target sequence results in a sample having 10%, 15%, 20%, 25%, 30%, 35%, 40%, 45%, 50%, 55%, 60%, 65%, 70%, 80%, 90%, 95% or more, mutant target sequence compared to wild type sequence (e.g., 10% mutant target sequence:90% wild type sequence to 95% mutant target sequence:5% wild type sequence).

Several methods of enriching mutant target sequence relative to wild-type target sequence are known in the art. Non-limiting examples of mutation enrichment methods include Nuclease-assisted Minor-allele Enrichment using Probe Overlap (NaME-PrO), Coamplification at Lower Denaturation temperature-PCR (COLD-PCR), Improved and Complete Enrichment COLD-PCR (ice-COLD-PCR), Temperature-Tolerant ice-COLD-PCR (TT-ice-COLD-PCR), toehold PCR blocker-PCR using locked nucleic acids (LNA), peptide nucleic acids (PNA or XNA), or blockers with other modified nucleotides, CRISP-R-mediated mutation enrichment by selecting mutated alleles or removing wild-type alleles and Differential Strand Separation at Critical Temperature (DiSSECT).

NaMe and NaMe-PrO methods are described in PCT/US2016/039167, which is incorporated herein by reference in its entirety. A non-limiting example of a NaMe-PrO protocol includes:

(a) preparing an amplification reaction mixture comprising the double-stranded mutant and wild-type target nucleic acids, a thermostable double strand-specific nuclease (DSN), PCR amplification components, and a pair of oligonucleotide probes, one of which is complementary to the wild-type nucleic acid top strand and the other is complementary to the wild-type nucleic acid bottom strand, wherein the probes may overlap each other by 10-15 probes such that the overlap coincides with the target region or be non-overlapping and contiguous;

(b) subjecting the reaction mixture to a denaturing temperature to permit denaturation of the wild-type nucleic acid and the mutant target nucleic acid;

(c) reducing the temperature to permit hybridization of the probes to their corresponding sequences on the wild-type and mutant target nucleic acids thereby forming complementary wild-type-probe duplexes, wherein the DSN cleaves the complementary wild-type-probe duplexes but not the partially complementary target mutant-probe duplexes; and (d) subjecting the reaction mixture to an amplification condition thereby enriching the uncleaved mutant target nucleic acid relative to the cleaved wild-type nucleic acid.

In some embodiments, an overlap of NaMe-PrO probes coincides with one or more mutations. In some embodiments, NaMe-PrO probes have a 3'-terminal polymerase block. In some embodiments, the probes are complementary to SNPs near target mutations.

In some embodiments, NaMe or NaMe-PrO is then followed by amplification of remaining mutant and wild-type target nucleic acids. In some embodiments, 1-50 cycles (e.g., 1-40, 2-30, 5-15, 5-10 cycles) of PCR are used to amplify mutant and wild-type target nucleic acids after NaMe or NaMe-PrO.

In some embodiments, NaMe-PrO with or without amplification results in mutation enrichment relative to wild-type target nucleic acids of 1-200-fold (e.g., 1-150-, 5-100- or 10-100-fold) compared to the unenriched sample. In some embodiments, NaMe-PrO with or without amplification results in mutation enrichment relative to wild-type target nucleic acids of more than 200-fold (e.g., 250-fold or 300-fold).

In some embodiments, a form of COLD-PCR (e.g., ice-COLD-PCR, TT-ice-COLD-PCR or oscillating COLD-PCR) is used to enrich mutant target nucleic acids relative to wild-type target nucleic acids. Methods of COLD-PCR and oscillating COLD-PCR are described in WO 2009/017784, which is incorporated by reference herein in its entirety. A non-limiting example of a COLD-PCR protocol includes:

(a) denaturing the double-stranded mutant and wild-type target nucleic acids by subjecting the double-stranded target mutant and wild-type nucleic acids to a first denaturing temperature that is above the melting temperature of the wild-type nucleic acid;

(b) forming a target mutant/wild-type strand duplex;

(c) denaturing said mutant/wild-type strand duplex by subjecting the nucleic acid amplified portion to a critical temperature (Tc) that is below the Tm of the wild-type nucleic acids;

(d) annealing a primer pair to the mutant and wild-type target nucleic acid strands; and (e) extending said primer pair so as to enrich said mutant target sequence relative to said wild-type strand.

In some embodiments, COLD-PCR is performed for 1-50 cycles (e.g., 1-40, 2-30, 5-25, 8-20 or 5-10 cycles) to enrich mutant target nucleic acid relative to wild-type target nucleic acid.

If the above example of COLD-PCR were to be adapted for oscillating COLD-PCR, steps (b) and (c) would be repeated. In some embodiments of oscillating COLD-PCR, forming a target mutant/wild-type strand duplex and denaturing said mutant/wild-type strand duplex, is repeated 1-29 times (e.g., 1-19 or 2-9 times).

Methods of ice-COLD-PCR and TT-COLD-PCR are described in WO 2012/135664, which is incorporated by reference herein in its entirety. A non-limiting example of an ice-COLD-PCR protocol includes:

(a) exposing the mutant and wild-type target nucleic acids to a reference sequence that is complementary the target sequence;

(b) denaturing the double-stranded target mutant and wild-type nucleic acids by subjecting the double-stranded mutant and wild-type target nucleic acids to a first denaturing temperature that is above the melting temperature of the wild-type nucleic acid;

(c) forming a target mutant/reference strand and target wild-type/reference strand duplexes;

(d) denaturing said mutant/reference strand duplex by subjecting the nucleic acid sample to a critical temperature (Tc) that is below the Tm of the wild-type/reference duplex;

(e) annealing a primer pair to the mutant and wild-type target nucleic acid strands; and (f) extending said primer pair so as to enrich said mutant target sequence relative to said wild-type target nucleic acid.

A non-limiting example of a TT-ice-COLD-PCR protocol includes:

(a) exposing the mutant and wild-type target nucleic acids to a reference sequence that is complementary the target sequence;

(b) denaturing the double-stranded target mutant and wild-type target nucleic acids by subjecting the double-stranded target mutant and wild-type nucleic acids to a denaturing temperature that is above the melting temperature of the wild-type nucleic acid;

(c) forming a target mutant/reference strand and target wild-type/reference strand duplexes;

(d) denaturing said mutant/reference strand duplex by subjecting the nucleic acid sample to a first critical temperature (Tc) that is below the Tm of the wild-type/reference duplex;

(e) annealing a primer pair to the mutant and wild-type target nucleic acid strands;

(f) extending said primer pair so as to enrich said mutant target nucleic acid relative to said wild-type target nucleic acid; and (f) repeating steps (d) to (f) at least once at a second Tc which is above the first Tc.

In some embodiments, any form of COLD-PCR (as described above) with or without amplification results in mutation enrichment relative to wild-type target nucleic acids of 1-200-fold (e.g., 1-150-, 5-100- or 10-100-fold) compared to the unenriched sample. In some embodiments, any form of COLD-PCR with or without amplification results in mutation enrichment relative to wild-type target nucleic acids of more than 200-fold (e.g., 250-fold or 300-fold) compared to the unenriched sample.

In some embodiments, DiSSECT is used to enrich mutant target nucleic acids relative to wild-type target nucleic acids. DiSSECT is a method that enriches unknown mutations of targeted DNA sequences purely based on thermal denaturation of DNA duplexes without the need for enzymatic reactions. Methods of DiSSECT are described in Guha et al. (Nucleic Acids Research, 2012, 1-9), which is incorporated herein by reference in its entirety. A non-limiting example of a DiSSECT protocol includes:

(a) allowing mutant and wildtype target nucleic acids to bind to complementary probes which are immobilized to beads, wherein the probes resemble the wild-type nucleic acids;

(b) denaturing the target mutant/probe duplex by subjecting the nucleic acid sample to a critical temperature such that the wild-type/probe duplex does not denature;

(c) collecting the eluate from the beads; and (d) repeating at least once (a)-(c) using beads on which the probes are unbound to any nucleic acid.

In some embodiments, DiSSECT is performed for 1-20 cycles (e.g., 1-18, 2-6, 2-4, 2-10 or 5-15 cycles). In some embodiments, DiSSECT results in mutation enrichment relative to wild-type target nucleic acids of 1-600-fold (e.g., 100-fold, 200-fold, 300-fold, 400-fold, 500-fold or 600-fold) compared to the unenriched sample.

'Allele' refers to alternative forms of a gene, portion thereof or non-coding region of DNA that occupy the same locus or position on homologous chromosomes that have at least one difference in the nucleotide sequence. The term allele can be used to describe DNA from any organism including but not limited to bacteria, viruses, fungi, protozoa, molds, yeasts, plants, humans, non-humans, animals, and archaebacteria. The alleles may be found in a single cell (e.g., two alleles, one inherited from the father and one from the mother) or within a population of cells (e.g., a wild-type allele from normal tissue and a somatic mutant allele from diseased tissue).

An allele can be 13-2000 nucleotides long. In one embodiment the allele is 20, 30, 40, 50, 60, 70, 80, 90, 100, 110, 120, 130, 140, 150, 160, 170, 180, 190, 200, 250, 300, 350, 400, 450, 500, 600, 700, 800, 900 or more nucleotides long. Alleles will generally share 50%, 60%, 70%, 80%, 85%, 90%, 91%, 92%, 93%, 94%, 95%, 96%, 97%, 98%, 99% or more homology to each other.

As used herein, a nucleic acid sample refers to any substance containing or presumed to contain a nucleic acid of interest (target and wild type sequences) or which is itself a nucleic acid containing or presumed to contain a target nucleic acid of interest. The term "nucleic acid sample" thus includes a sample of nucleic acid (genomic DNA, cDNA, RNA), cell, organism, tissue, or fluid, including but not limited to, for example, plasma, serum, spinal fluid, lymph fluid, synovial fluid, urine, tears, stool, external secretions of the skin, respiratory, intestinal and genitourinary tracts, saliva, blood cells, tumors, organs, tissue, samples of in vitro cell culture constituents, natural isolates (such as drinking water, seawater, solid materials), microbial specimens, and objects or specimens that have been "marked" with nucleic acid tracer molecules. The nucleic acid sample may be obtained from mammals, viruses, bacteria or plants. In some embodiments, the nucleic acid sample is DNA circulating in plasma, urine or other bodily fluids.

As used herein "oligonucleotide probes" refer to molecules comprising two or more deoxyribonucleotides or ribonucleotides. By "complimentary" it is meant that the probes hybridize without any mismatches to the sequences in the top and bottom stands of the wild type nucleic acid.

As used herein, "primers' refers to oligonucleotides that anneal to opposite strands of a mutant target and wild type sequence so as to form an amplification product during a PCR reaction.

The term "barcode" as used herein refers to a unique sequence of nucleotides that allows identification of the nucleic acid of which the barcode is a part. Barcoding a DNA fragment is a process by which the DNA fragment is uniquely tagged with one or more short identifying sequences. In some embodiments, it is desired for each DNA fragment in a sample to have a barcode that is unique from barcodes on any other DNA fragment in the sample. In some embodiments, each DNA fragment in a sample comprises one unique barcode. In some embodiments, each DNA fragment in as sample comprises two barcodes that are unique from each other and unique from any other barcode that is attached to any other DNA fragment in the sample.

Such uniqueness of barcodes in a sample of DNA fragments can be accomplished, for example, by optimizing the length of each barcode (i.e., the number of nucleotides in each barcode) and/or the ratio of unique barcodes to DNA fragments during barcoding (i.e., attaching barcodes to DNA fragments).

Barcodes can be any appropriate length. In some embodiments, the length of each barcode used to barcode DNA fragments in a sample is 6-20 bp long (e.g., 8-18 bp, 8-14 bp, 10-16 bp or 12-14 bp). In some embodiments, the length of each barcode used to barcode DNA fragments in a sample is 14 bp long.

Barcodes can be attached to DNA fragments in any appropriate ratio. In some embodiments, the ratio of unique barcodes to DNA fragments during barcoding is $10^6$-$10^{10}$ (e.g., $10^6$, $10^7$, $10^8$, $10^9$, $10^{10}$) unique barcodes to 100 ng of DNA (or $3\times10^4$ allelic copies).

Methods of attaching barcodes to nucleic acids are known in the art. Various publications provide descriptions of barcoding technology. For example, Wong and Moqtaderi (Curr Protoc Mol Biol. 2013; Chapter 7:Unit 7.11) describe a barcoding protocol for the preparation of up to 96 ChIP samples for multiplex sequencing in a single flow cell lane on the Illumina platform; and Stahlberg et al. (Nucleic Acids Res. 2016 Jun. 20; 44) describe a PCR-based barcoding method, both of which are incorporated herein by reference in their entirety. The following patents that also describe DNA barcoding methods are also incorporated herein by reference in their entirety: U.S. Pat. Nos. 8,691,509, 8,268, 564 and US application 20120220494A1.

In some embodiments, double-stranded barcodes are attached to a double-stranded DNA fragment by ligation. In some embodiments, double-stranded DNA fragments are barcoded using PCR technique employing primers that comprise unique barcodes.

As used herein, the term, "common sequence tag" refers to a nucleotide sequence that is common to all the DNA fragments in a sample, e.g., a sample of genomic fragmented DNA. A common tag enables processing of all the DNA fragments in a sample. For example, primers complementary to a common tag in a sample may be used to amplify all DNA fragments in a sample, regardless of whether a DNA fragment contains target nucleic acid (e.g., mutant target nucleic acid or wild-type target nucleic acid) or non-target nucleic acid.

Figure 3A:
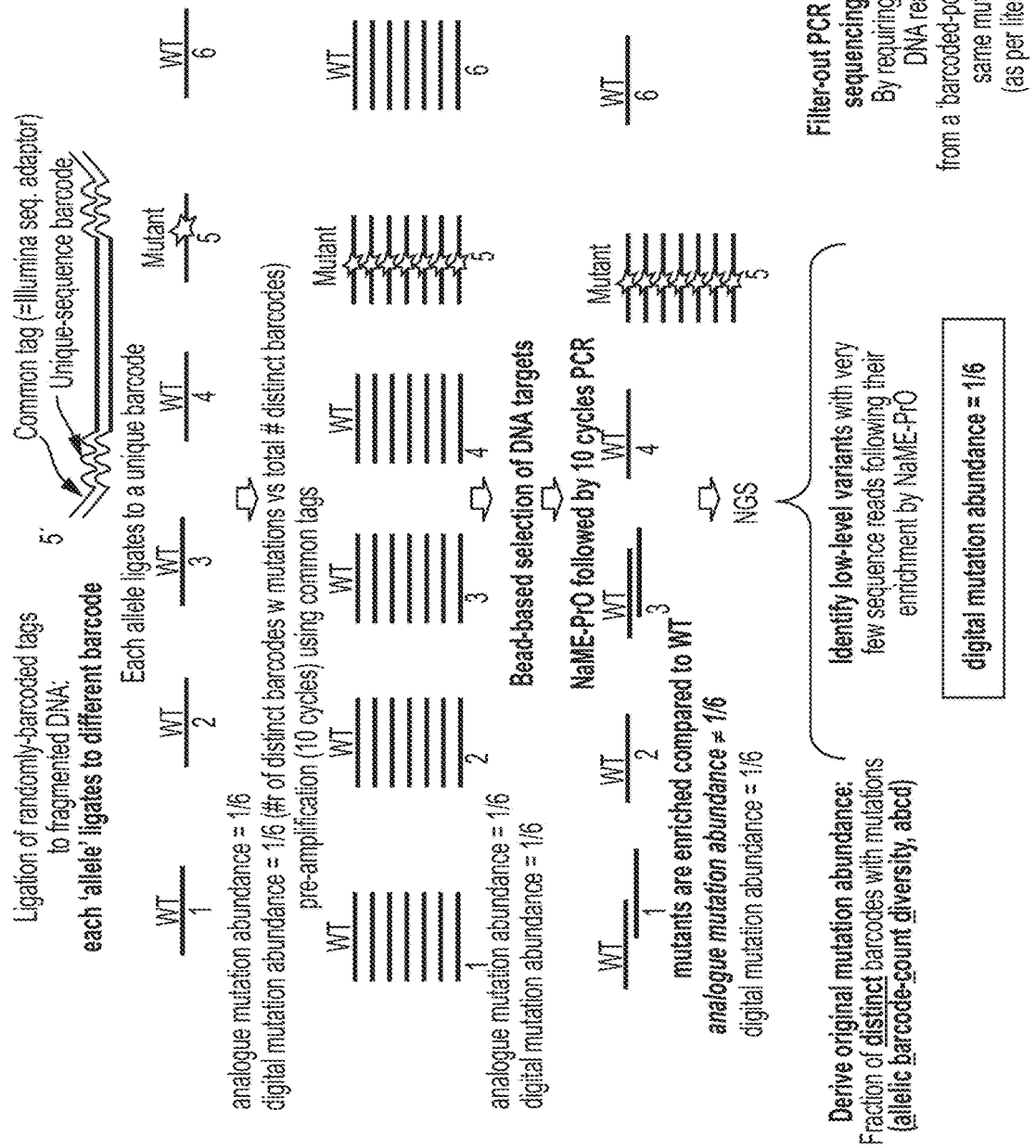
FIG. 3A describes derivation of original mutation frequency using allelic barcode-count diversity (abcd), following qNaME-PrO-NGS. The abcd approach de-couples the mutation enrichment from the original mutation abundance, by using the number of distinct molecular barcode families that are mutant versus WT for digital quantification of mutation abundance. Mutation-containing barcodes are enriched and appear more frequently than barcodes with WT sequences. However this does not affect the quantification since it is the diversity of barcodes, not their frequency that is used.

For any one of the methods disclosed herein, a sample of double-stranded genomic DNA may comprise double-stranded DNA fragments, wherein each terminus of the genomic DNA fragments is attached to a unique double-stranded barcode and a double-stranded common sequence tag, wherein the common sequence tag is located upstream of the unique barcode. By being located "upstream" of the unique tag, it is meant that the common tag is located 5' relative to the unique tag if the unique barcode, common tag and DNA fragment sequence are read from 5' to 3'. FIG. 3A depicts an example of how a common tag is located relative to a unique barcodes for any one of the methods described herein.

Common sequence tags can be any appropriate length. In some embodiments, a common tag is 16-40 bp long (e.g., 16-40, 18-36, 20-32, 22-30 or 24-28 bp long). In some embodiments, a common tag is 18 nucleotides long (i.e. an 18-mer). It is to be understood that a the terms "nucleotide" and 'base pair (bp)" are used interchangeably herein.

In some embodiments, a unique barcode and a common tag are attached to each end of a double-stranded DNA fragment at the same time using the same method. In some embodiments, a barcode and a common tag are attached to each end of a double-stranded DNA fragment by ligation.

In some embodiments, a unique barcode and common tag are attached to a terminus of a DNA fragment by starting from a single-stranded barcode, synthesizing the opposite strand of the single-stranded barcode using an extension reaction to form a double stranded barcode, and the ligating and end of the double-stranded genomic DNA fragment to the end of the barcode (FIG. 3A depicts such an embodiment).

Figure 4:
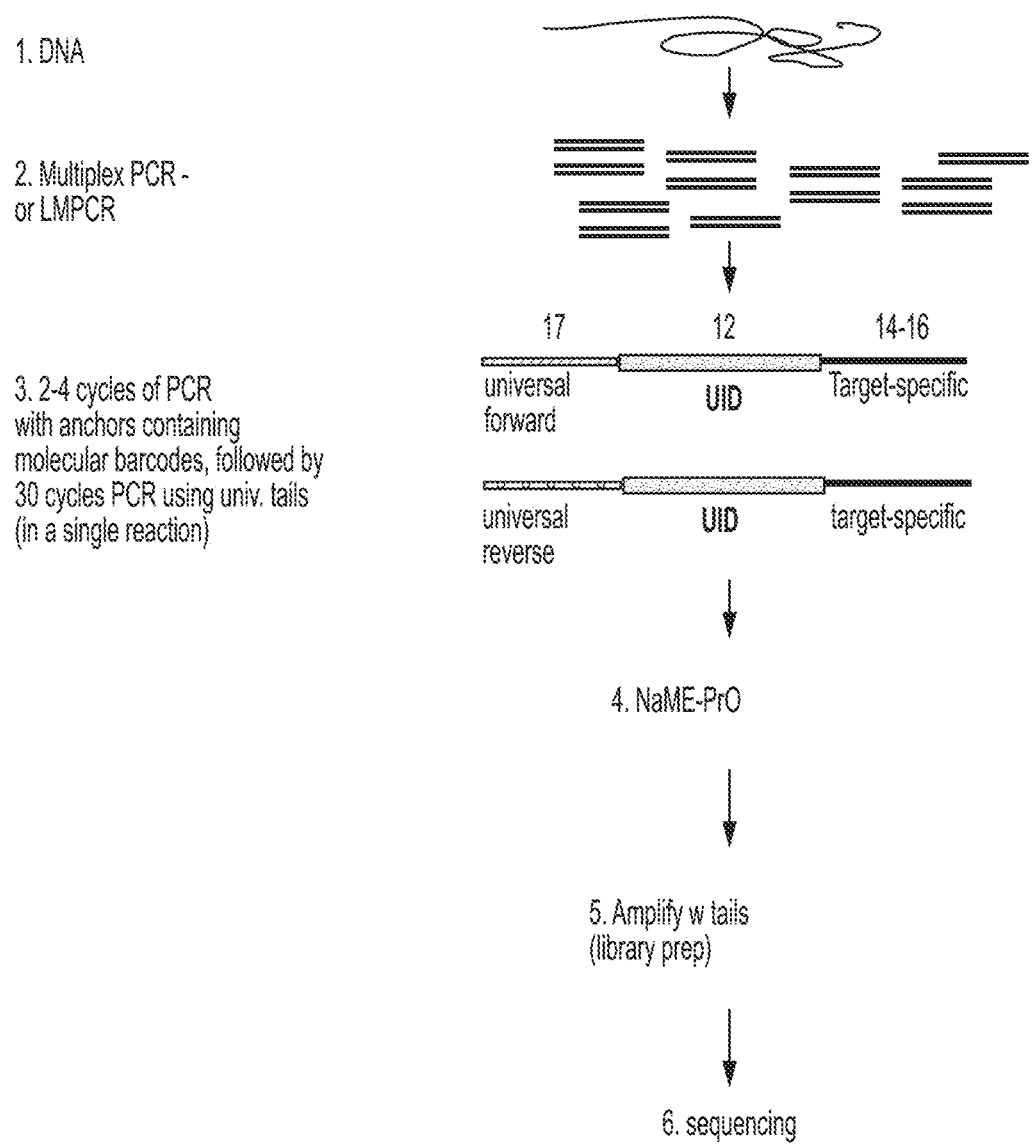
FIG. 4 describes attachment of molecular barcodes by using multiplexed-PCR instead of ligation. Following multiplexed PCR, the molecular barcodes are attached in the first few cycles of a second PCR, followed by several cycles of PCR using the universal 'tails'. NaME-PrO is then applied, followed by library preparation and sequencing. The mutation enrichment occurs during the NaME-PrO step, i.e. after incorporation of the barcodes and initial expansion by the first few cycles of the second PCR.
Figure 5:
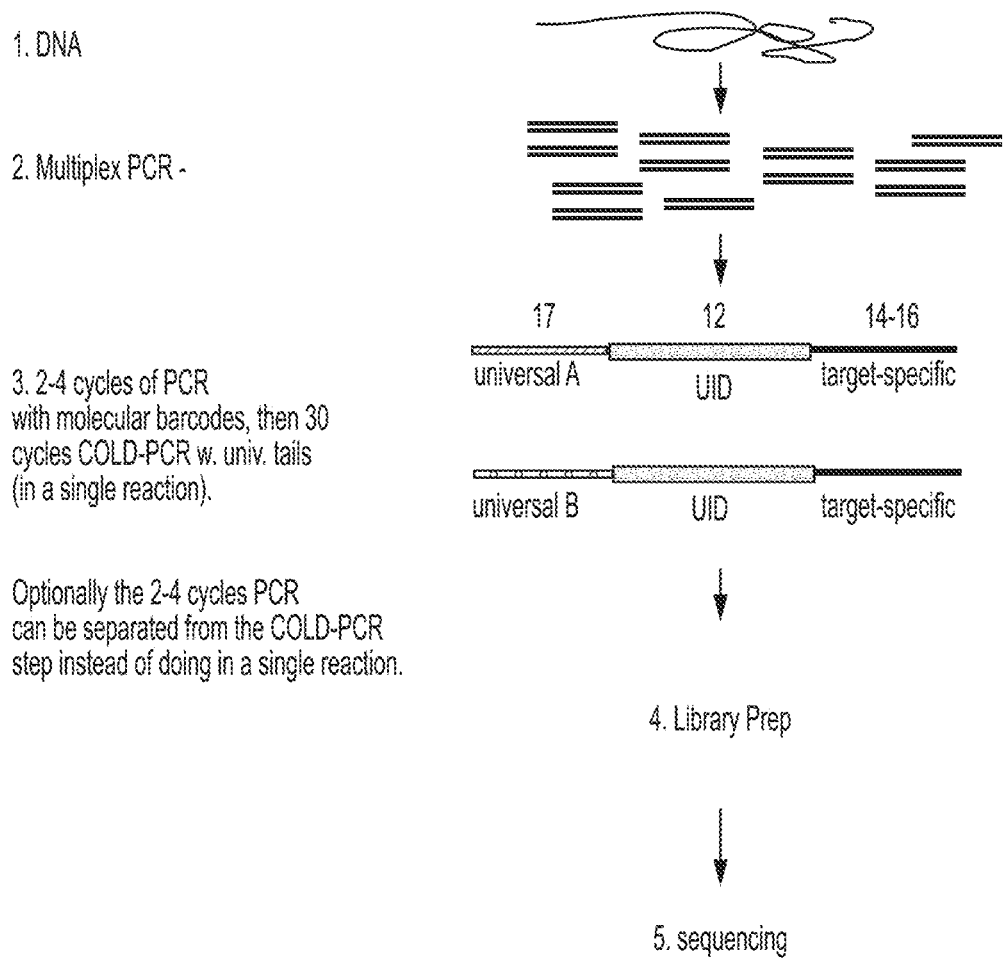
FIG. 5 describes use of molecular barcodes for quantification when using multiplexed COLD-PCR. Following multiplexed PCR, the molecular barcodes are attached in the first few cycles of a second PCR, followed by several cycles of COLD-PCR using the universal 'tails'. The mutation enrichment occurs during the COLD-PCR cycles, i.e. after incorporation of the barcodes and initial expansion by the first few cycles of the second PCR. Mutation-enriched COLD-PCR products are then processed for library preparation and sequencing.
Figure 6:
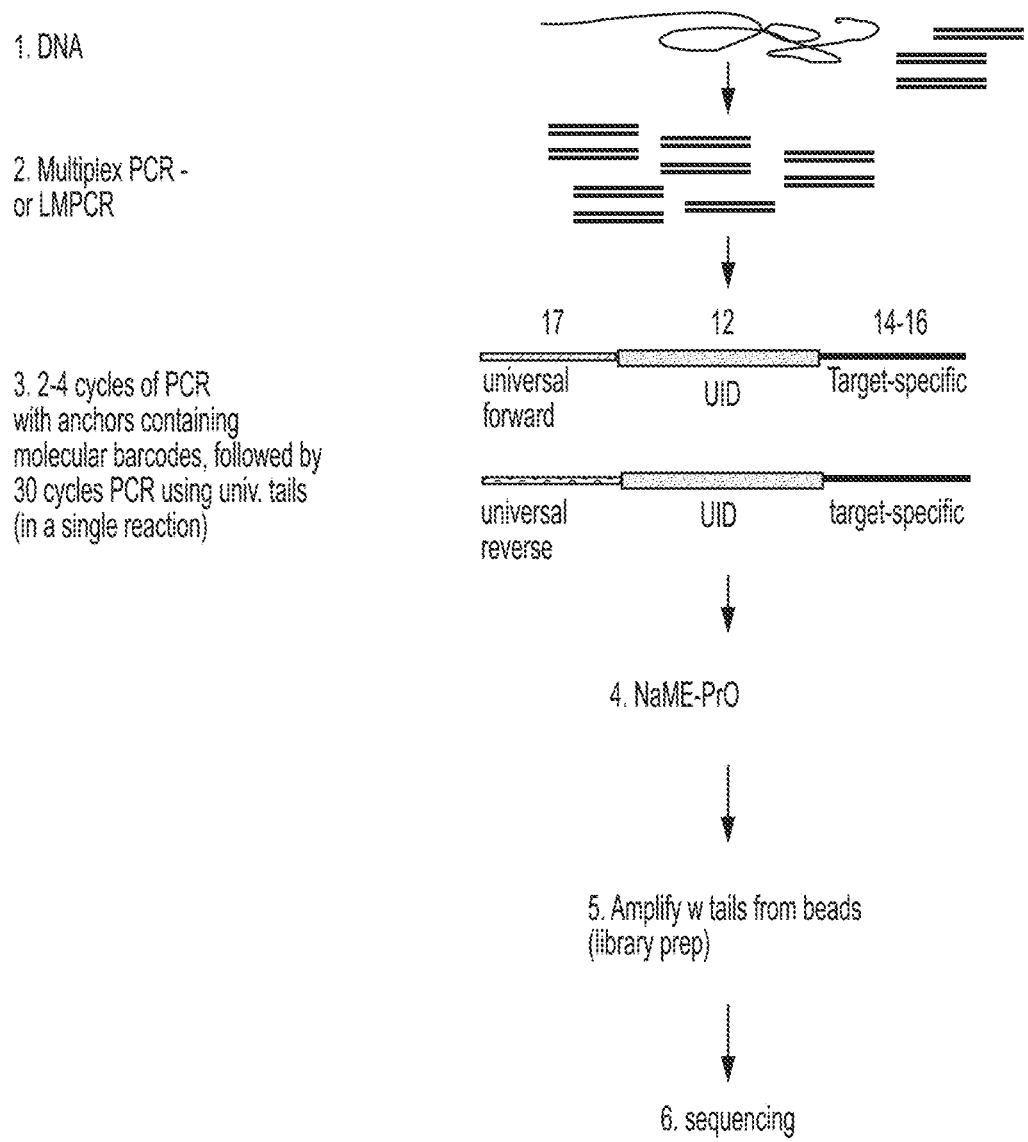
FIG. 6 describes use of molecular barcodes for quantification when using multiplexed COLD-PCR and NaMe-PrO. Following multiplexed PCR, the molecular barcodes are attached in the first few cycles of a second PCR, followed by several cycles of COLD-PCR using the universal 'tails'. Mutation enrichment occurs during the COLD-PCR cycles, i.e. after incorporation of the barcodes and initial expansion by the first few cycles of the second PCR. Mutation-enriched COLD-PCR products are then further enriched for mutations using NaMe-PrO, and then processed for library preparation and sequencing.
Figure 7A:
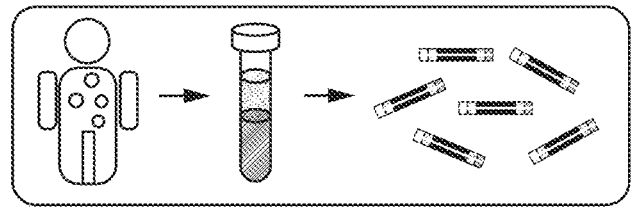
FIG. 7A shows an example workflow.
Figure 7A:
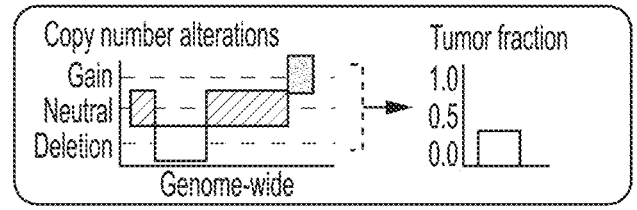
Figure 7A:
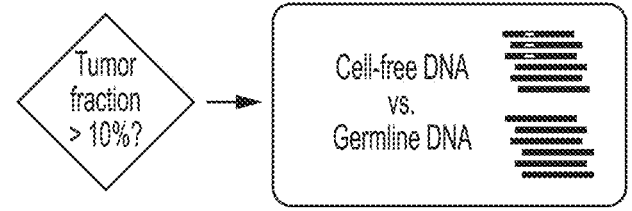
Figure 7B:
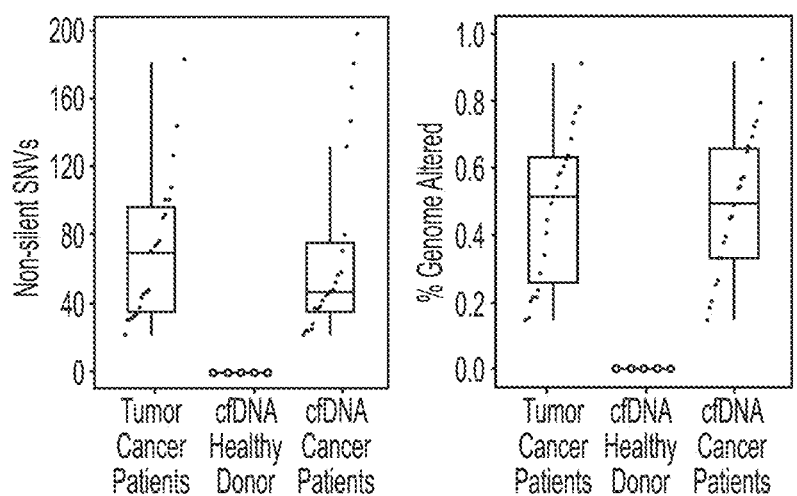
FIG. 7B shows analytical benchmarking.
Figure 7C:
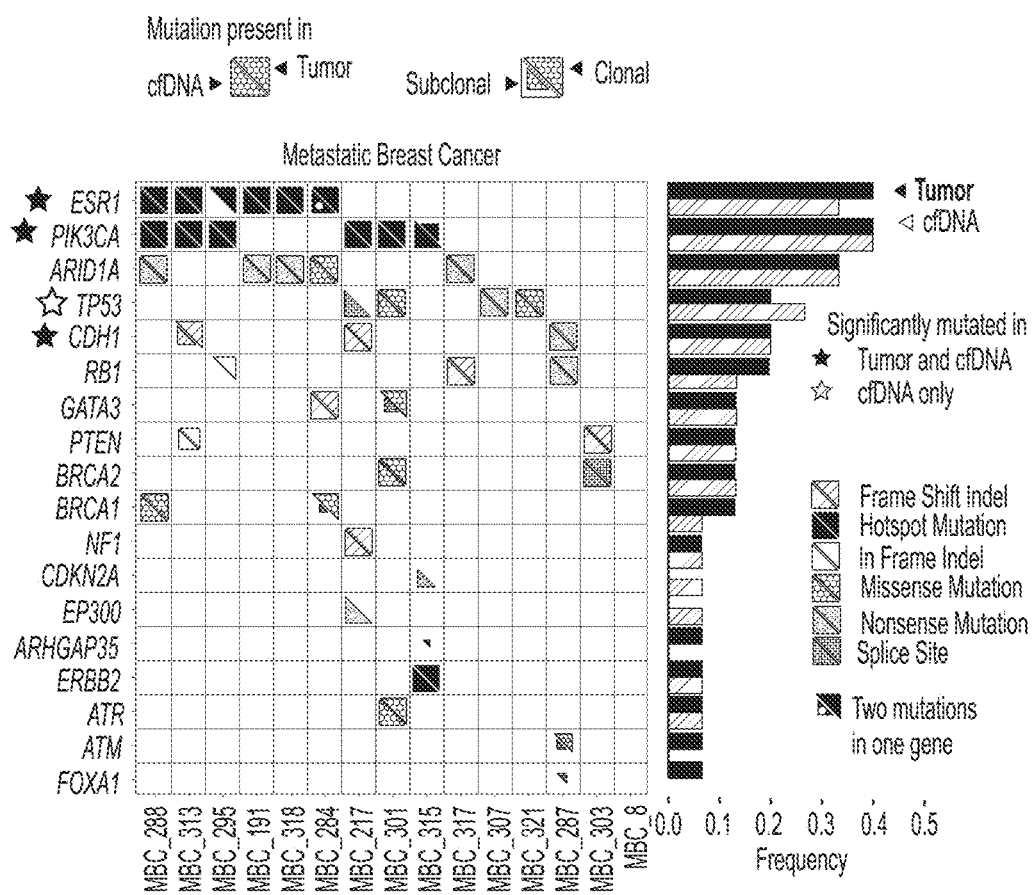
FIG. 7C shows somatic mutations in cfDNA and tumor biopsies.
Figure 7D:
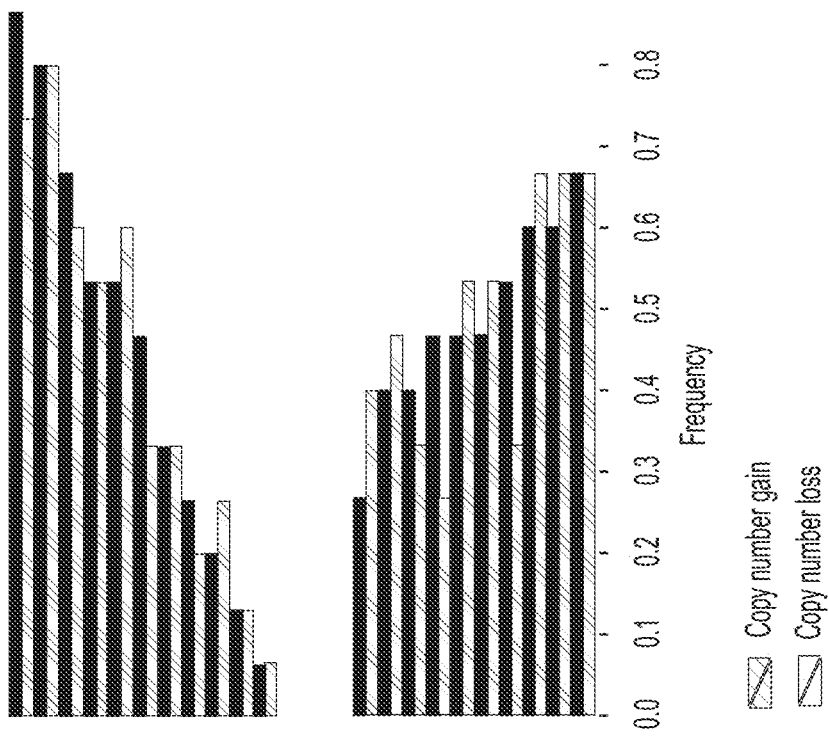
FIG. 7D shows somatic copy number alterations in cfDNA and tumor biopsies.
Figure 7D:
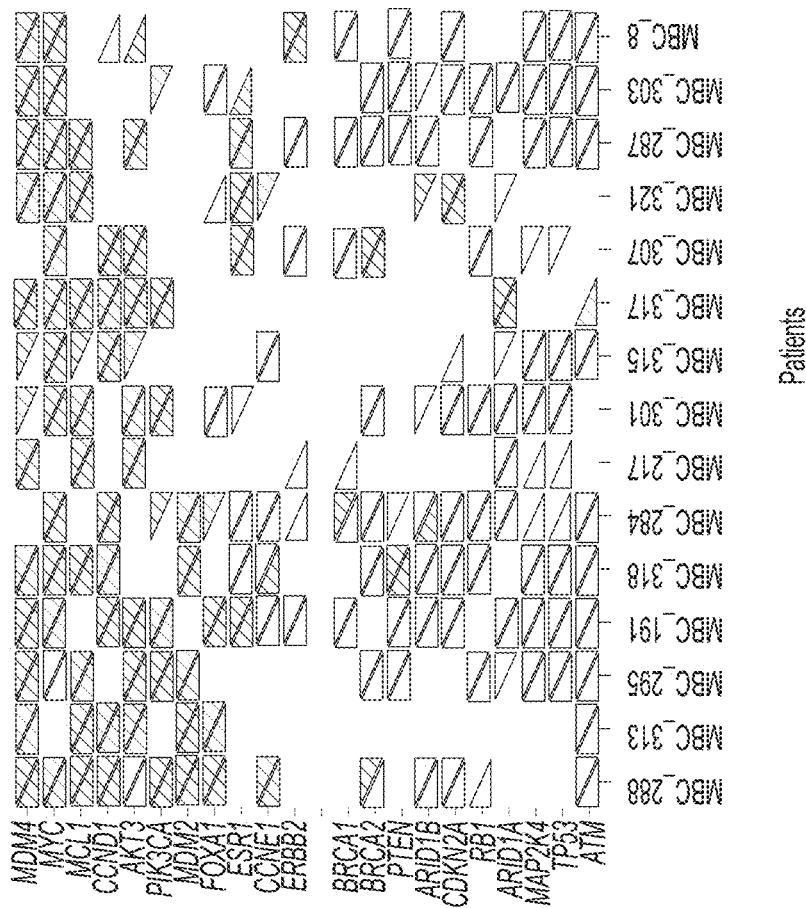

In some embodiments, a barcode and a common tag are attached to each end of a double-stranded DNA fragment by using multiplexed-PCR. In such embodiments, PCR using oligonucleotide primers are used, wherein each oligonucleotide primer comprises a common tag portion, a unique barcode portion and a target-specific portion. The target-specific portion enables attachment of the oligonucleotide primer to anneal to DNA fragments. Step 3 of FIGS. 4, 5 and 6 depict such an embodiment.

As used herein, the term, "sample-index" refers to a unique sequence of nucleotides that allows identification of the sample (e.g., an enriched or un-enriched sample) of DNA from which the DNA is sourced. For example, a sample of DNA fragments may be split so that one aliquot is enriched for mutant alleles, while another aliquot is not enriched. DNA from both samples can then be mixed and sequenced in the same sequencing reaction if sample indeces on the DNA allows identification of the source of the DNA, i.e., whether it was sourced from the enriched sample or the unenriched sample. For example, a sample-index on a DNA fragment from the enriched sample is the same as the sample-indices from all other DNA fragments from the enriched sample. Similarly, the sample-index on a DNA fragment from the un-enriched sample is the same as the sample-indices from all other DNA fragments from the un-enriched sample.

Sample-indexes, like barcodes, can be any appropriate length. In some embodiments, the length of each sample-index used to index each DNA sample is 6-20 bp long (e.g., 8-18 bp, 8-14 bp, 10-16 bp or 12-14 bp). In some embodiments, the length of each barcode used to barcode DNA fragments in a sample is 14 bp long.

In some embodiments, the methods disclosed herein require genomic DNA to be in fragmented form In some embodiments, genomic DNA in a sample collected from a subject is already fragmented. For example, a sample of cell-free genomic DNA or genomic DNA circulating in blood is fragmented when collected. In some embodiments, genomic DNA from samples of the urine of a subject is fragmented. In some embodiments, genomic DNA collected from bodily fluid or tissue sample of a subject is not fragmented and needs to be fragmented. In some embodiments, a sample of genomic DNA is fragmented but it is desired to fragment it further to make smaller fragments. Various techniques to fragment double-stranded DNA are known in the art. In some embodiments, DNA is sheared physically (e.g., using acoustic shearing using a Covaris instrument, sonication using a Bioruptor or hydrodynamic shearing using a Hydroshear instrument). In some methods, double-stranded DNA is sheared enzymatically using any DNAase type of enzyme that digests DNA randomly (e.g., a Shearase, DNAse1 or a transposase). In some embodiments, double-stranded DNA is fragmented by chemical fragmentation (e.g., by exposing the DNA to be fragmented to heat and divalent metal cation. Depending on the method of DNA fragmentation, DNA fragments may be subjected to enzymatic end-repairing to obtain blunt ends.

In some embodiments of any one of the methods disclosed herein, a double-stranded DNA fragment is 20-400 bp long (e.g., 10-400, 40-200, 50-150 or 50-100 bp long).

In any of the methods disclosed herein, obtaining a measure of total unique barcodes in a sample may be accomplished using DNA sequencing methods. Several sequencing methods and protocols for sample preparation for these methods are well-established in the art. Indeed, one of the advantages of the methods disclosed herein is that they are compatible with established methods of sample preparation for sequencing methods used in the field. Examples of methods of sequencing include SANGER sequencing, MiSeq sequencing, massively parallel signature sequencing (MPSS), pology sequencing, 454 sequencing, Illumina (or Solexa) sequencing, SoLiD sequencing, Ion Torrent semiconductor sequencing, single molecule real time (SMRT) sequencing, and nanopore sequencing. The following publications describe various sequencing options and are incorporated herein by reference in their entirely: Goodwin et al. (Coming of age: ten years of next-generation sequencing technologies, Nature Reviews Genetics 17, 333-351 (2016)), Heather and Chain (The sequence of sequencers: The history of sequencing DNA, Genomics, 107: 1-8 (2016)), and Moorthie et al. (Review of massively parallel DNA sequencing technologies, Hugo J. 2011 December; 5(1-4): 1-12).

Methods of Determining the Abundance of More than One Mutation in a Sample of Genomic DNA In some embodiments, any one of the methods disclosed here is applied to determine the abundance of more than one mutation in a sample of genomic DNA. In some embodiments, the more than one mutations are at different loci on genomic DNA. In some embodiments, mutations are present at known hotspots for a particular disease. For example, there are 292 known hotspots for mutations in lung cancer (Newman et al., Nat Med 2014, 20:548-54; Newman et al., Nat Biotechnol 2016, 34:547-55). In some embodiments, the more than one mutations are on the same exon. In some embodiments, the more than one mutations are present on different exons. In some embodiments, it might be desired to scan for mutations on a particular exon rather than testing particular hotspots.

Figure 10A:
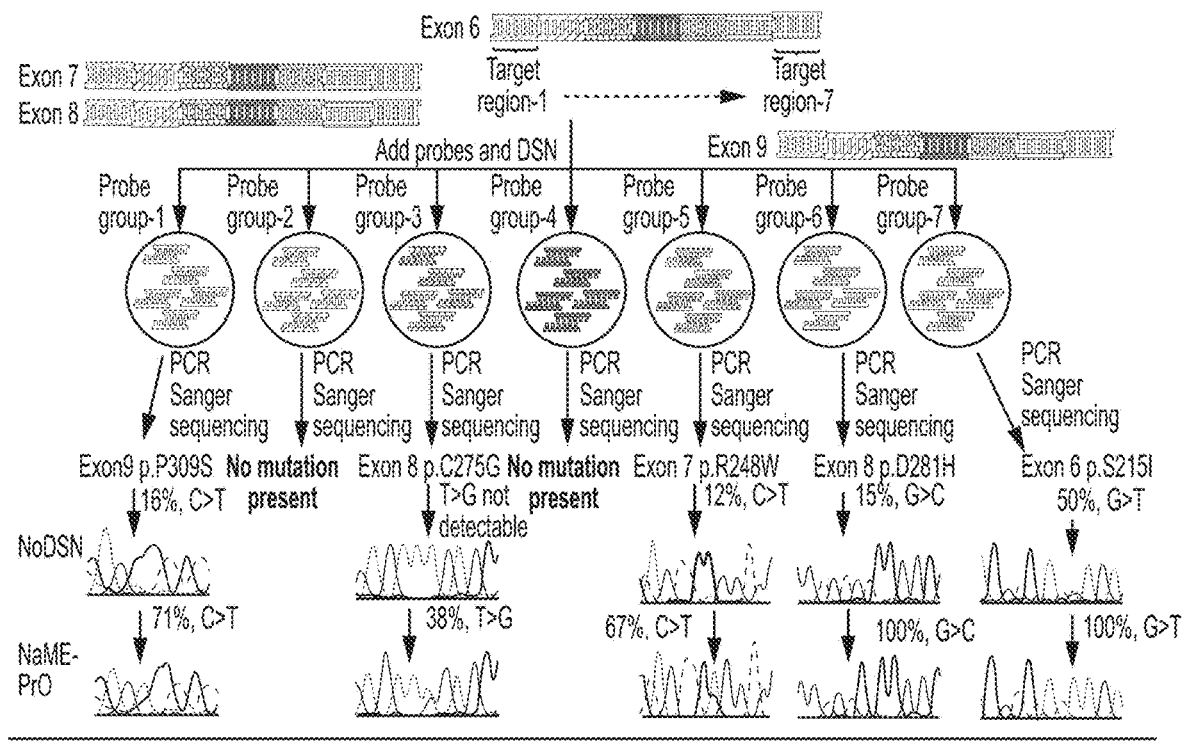
FIG. 10A shows a technique using overlapping probes: Mutation enrichment at all positions on TP53 exons 6-9 using concurrent NaME-PrO 'tiling' reactions. Genomic DNA mix of cell lines containing mutations at several TP53 positions in exons 6-9 was treated via NaME-PrO in seven parallel reactions using distinct groups of overlapping probes per reaction, such that NaME-PrO overlapping probes 'tile' the entire size of each exon. Mutation enrichment at all mutated sequences was observed following Sanger sequencing.
Figure 10B:
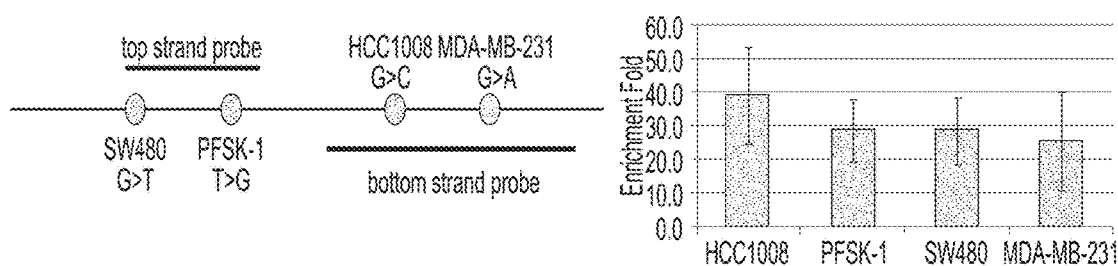
FIG. 10B shows a technique using contiguous, non-overlapping probes: Using contiguous, non-overlapping probes that cover 25+25=50 bp per reaction it is possible to cover an average cfDNA fragment size of ~150 bp using 3-4 NaME-PrO parallel reactions, while still obtaining good mutation enrichment at all positions of all exons targeted. An example for multiple mutations along TP53 exon 8 is shown. Mutation enrichment 30-40-fold was derived by performing digital droplet PCR before & after NaME-PrO as described[8]. Significantly lung CA gene fusions (e.g., EML4-ALK fusion1) that result to breakpoints within the mapped exons will also be enriched by NaME-PrO, since probes corresponding to the WT cfDNA fragment will not bind adequately the fusion breakpoint and DSN will not digest those fragments, resulting to enrichment.

In some embodiments, mutant alleles of a target nucleic acid are enriched relative to wild-type alleles of target nucleic acid by subjecting the sample to multiplexed NaME-Pro. In some embodiments, multiplexed NaME-PrO uses overlapping probe pairs in parallel reactions, wherein each parallel reaction uses a distinct pair of overlapping probes, such that the totality of overlapping probe pairs span a contiguous region of genomic DNA of interest. Such an embodiment is exemplified in FIG. 10A. In some embodiments, multiplexed NaME-PrO uses continuous and non-overlapping probe pairs in parallel reactions, wherein each parallel reaction uses a distinct pair of non-overlapping probes, such that the totality of non-overlapping probe pairs span a contiguous region of genomic DNA of interest. Such an embodiment is exemplified in FIG. 10B.

Provided herein are methods of diagnosis and or prognosis of a disease based on determining abundance of a mutant allele of a target nucleic acid or sequence in a sample of genomic DNA from a subject. Accordingly, provided herein is a method of determining disease diagnosis or prognosis in a subject, which comprises determining the abundance of a mutant allele of a target nucleic acid in a sample of genomic DNA of the subject according to any one of the methods disclosed herein. An increase in the abundance of a mutant allele of a target nucleic acid in a sample of genomic DNA of the subject is indicative of a worsening diagnosis or prognosis of disease in the subject. In some embodiments, abundance of a mutant allele of a target nucleic acid in a sample of genomic DNA of the subject is determined over a period of time (e.g., over weeks, months or years).

In some embodiments, any one of the methods disclosed herein is used to determine efficacy of a therapeutic treatment or intervention in a subject. In some embodiments, efficacy of a therapeutic treatment or intervention is determined by determining the abundance of mutant alleles in a sample of genomic DNA from the subject after the therapeutic intervention or treatment and comparing it to the abundance of mutant alleles in a sample of genomic DNA from the subject before the subject was subjected to the therapeutic treatment or intervention. A decrease in abundance of mutant alleles in the sample after treatment is indicative of therapeutic efficacy in the subject. In some embodiments, abundance of mutant alleles in a sample of genomic DNA from the subject is determined more than once after a therapeutic treatment or intervention. In some embodiments, abundance of mutant alleles in a sample of genomic DNA from the subject is determined 2-5 times after the subject undergoes a therapeutic treatment or intervention (e.g., two times a week after a treatment, or once every 6 weeks repeated 5 times).

Any one of the methods described herein can be used to obtain a fingerprint of mutations that are associated with a particular disease or condition. In some embodiments, such a method comprises determining relative original abundance of mutant alleles of target nucleic acids of a plurality of mutations according to the methods described herein, wherein the abundance of mutant alleles of target nucleic acids of a one or a plurality of mutations is determined in genomic DNA samples from one or more than one subject with the disease or condition. In some embodiments, the disclosed fingerprinting method can be applied to one type of sample from subjects (e.g., plasma samples of lung cancer patients at different cancer stages). Such a fingerprint can enable non-invasive testing for diagnosing and prognosing a disease or condition in a subject.

Without further elaboration, it is believed that one skilled in the art can, based on the above description, utilize the present disclosure to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1: Comprehensive Sequencing of Cell-Free DNA

This Example describes next generation sequencing of circulating cells, circulating DNA and bioinformatics Workflows for comprehensive sequencing of cell-free DNA were established and some of the most extensive benchmarking of liquid and conventional biopsies performed using both whole-exome and whole-genome sequencing in patients with metastatic cancer (FIG. 7 and [3]).

Example 2: qNaME-PrO for Mutation Enrichment in Lung Cancer Mutation Hotspots This example describes application of quantitative NaMe-PrO for mutation enrichment in lung cancer mutation hotspots. Following fragmentation of genomic DNA, DNA molecules are ligated to oligonucleotides containing unique identifiers (molecular barcodes), followed by pre-amplification and target selection for DNA targets containing potential mutation hotspots. 292 hotspots that are known to be recurrently mutated in lung cancer[1, 2] will be focused upon. qNAME-PRO is then applied to enrich mutations by >100-fold over all targets tested, followed by NGS. Serial dilutions of mutant-to-wild-type DNA, 5%-0.01% abundance are tested. Computational techniques are employed to provide mutation quantification based on allelic barcode-count diversity (abcd) and filter-out sequencing and PCR errors. Accuracy and selectivity of qNaME-PrO-NGS is evaluated and compared to existing NGS practices.

Figure 8B:
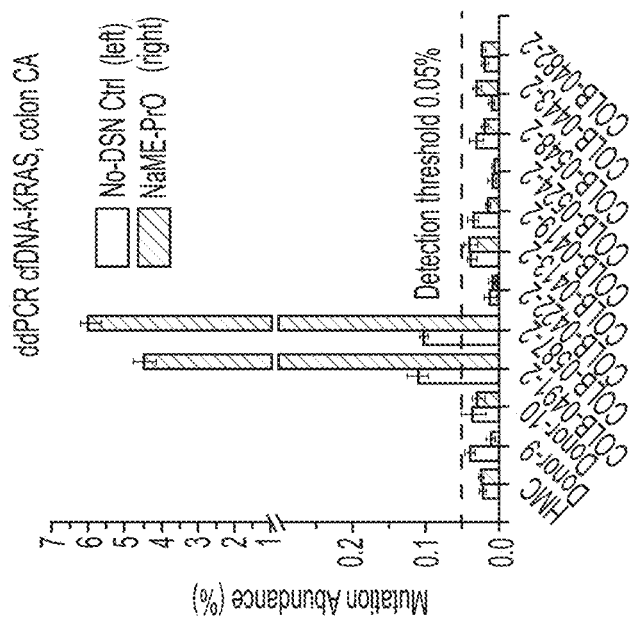
FIG. 8B shows ddPCR screening of cfDNA from colon CA patients: improvement via NaME-PrO is evident for the 2 positive samples.
Figure 8A:
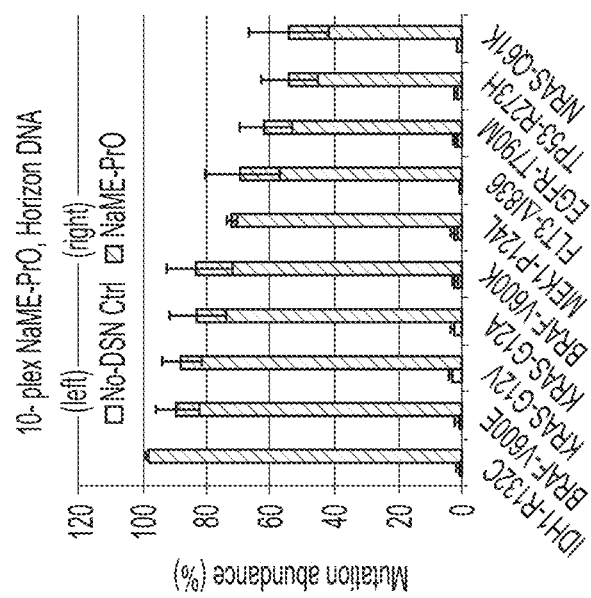
FIG. 8A shows 10-plex NaME-PrO applied directly to genomic DNA containing mutations in 10 actionable genes: mutations without NaME-PrO ('No DSN') vs. after NaME-PrO are compared, 50-100-fold enrichment is evident on all targets.
Figures 8C, 8D:
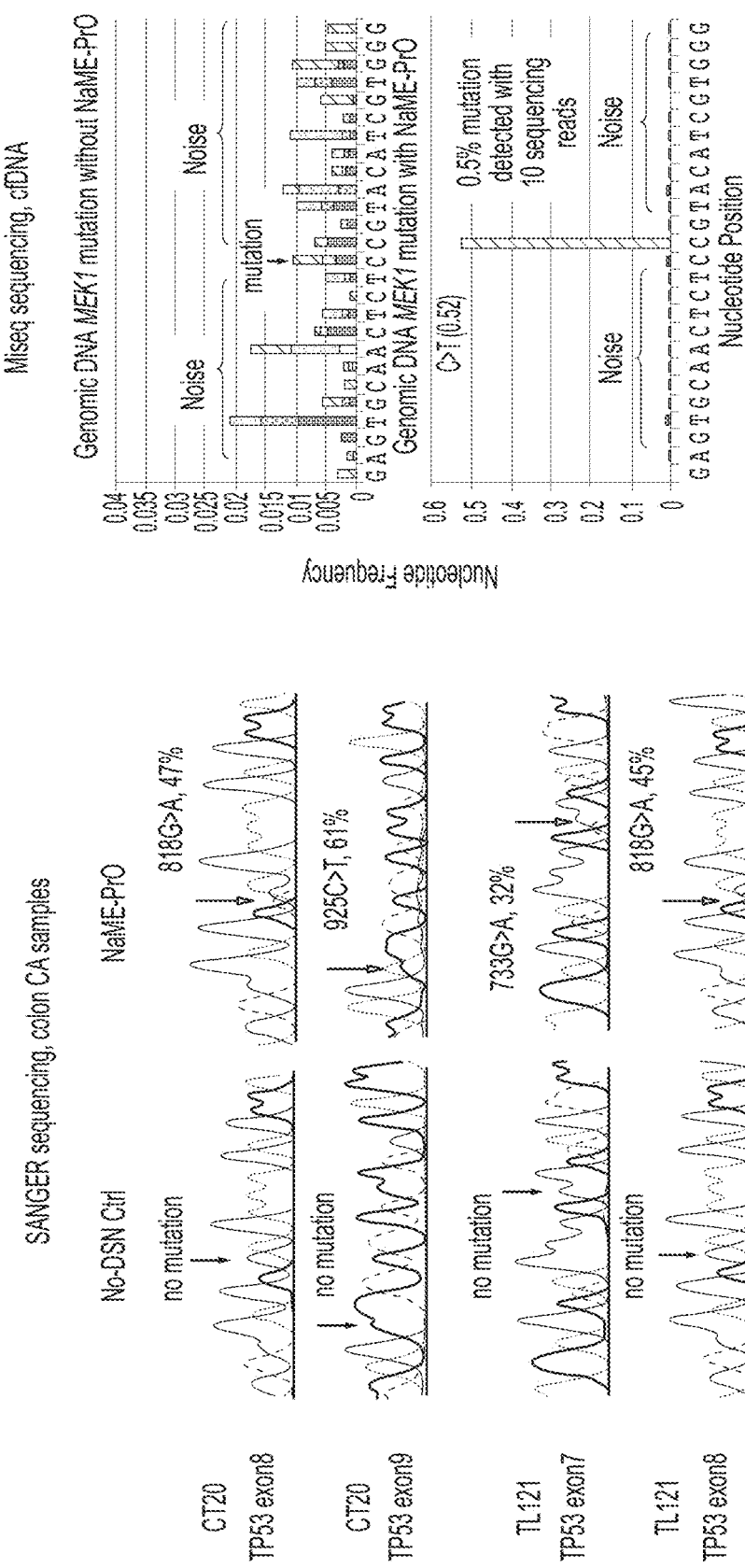
FIG. 8C shows Sanger sequencing without vs. with NaMe-PrO: low level mutations are revealed.
FIG. 8D shows MiSeq sequencing of 0.5% allelic abundance mutations with vs without NaME-PrO: the mutation becomes clearly distinguished from the sequencing noise after NaMe-PrO. This mutation was detectable with just 10 MiSeq sequencing reads following enrichment from 0.5% to 52% allelic abundance via NaME-PrO[8].

NaME-PrO (FIG. 1) employs a double-strand-DNA-specific nuclease (DSN) and overlapping oligonucleotide-probes interrogating WT-DNA targets and guiding nuclease digestion to these sites. Mutation-containing DNA creates probe-DNA mismatches that inhibit digestion, thus subsequent DNA-amplification magnifies DNA-alterations at all selected targets. NaME-PrO is a single step approach that operates at the level of genomic DNA prior to performing DNA amplification hence it is not impacted by polymerase errors. NaMe-PrO can achieve ~50-fold to several-hundred-fold mutation-enrichment, depending on conditions applied[8], in diverse human samples on multiple clinically-relevant targets including tumor samples and circulating-DNA in 10-plex or 50-plex reactions[8]. Enrichment enables routine mutation detection at 0.01% abundance while by adjusting conditions it is possible to sequence mutations down to 0.00003% abundance, or to scan tumor-suppressor genes for rare-mutations[8]. NaME-PrO introduces a simple and highly parallel process to remove un-informative DNA sequences and unmask clinically and biologically useful alterations. The method creates the potential for massively parallel mutation enrichment prior to sequencing and engenders a new paradigm whereby rare mutations do not require deep sequencing for their detection. Representative examples of the application of NaME-PrO in clinical specimens and cfDNA are shown in FIG. 8, while additional data and details are in[8].

Recovery of Tumor Fingerprint in Plasma-Circulating DNA Following NaME-PrO.

Figure 9:
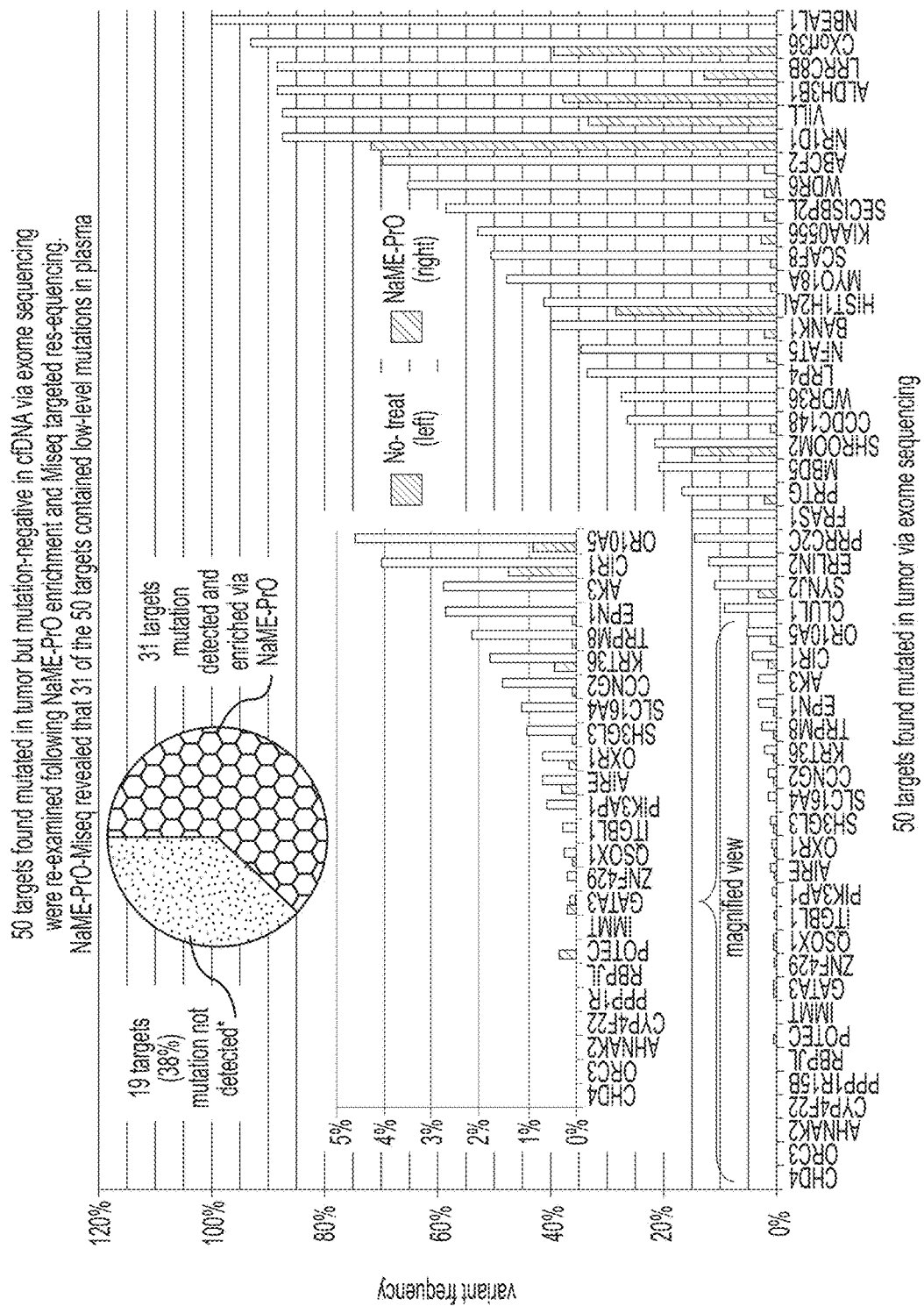
FIG. 9 describes NaME-PrO reveals multiple low-level mutations in cfDNA with a defined tumor signature. Whole-exome sequencing of both tumor tissue and corresponding cfDNA from a breast cancer patient revealed 50 somatic mutations present in the tumor but absent in cfDNA. NaME-PrO was applied to these same 50 targets using 30 ng cfDNA as starting material. Out of 50 targets, 31 (62%) revealed rare mutations following NaME-PrO-MiSeq NGS. Therefore the majority of the 'missing' tumor fingerprint was recovered in plasma following NaME-PrO enrichment. In general, low-level mutations were detected with 1-2 orders of magnitude fewer reads as compared to standard NGS.

In another demonstration of the power of the technique, NaME-PrO was applied followed by MiSeq targeted re-sequencing to cfDNA from a breast CA patient whose tumor and cfDNA were both sequenced over the whole exome (150× read-depth). There were 50 DNA targets found mutated in the tumor but non-mutated in plasma. It was hypothesized that at least some of these mutations are present in cfDNA but are at too low level to be identified by standard exome sequencing. To examine the hypothesis, linkers were ligated to cfDNA followed by 10 cycles ligation-mediated PCR using Q5 high fidelity polymerase (as in step 3, FIG. 2), followed by application of 50-plex NaME-PrO. Next, a 50-plex PCR was applied to provide target enrichment, followed by Illumina adaptor attachment and MiSeq sequencing. The data (FIG. 9) revealed 31 somatic mutations in cfDNA matching the 'missing' tumor mutations. Most of these were at 0.5-2% levels, however a few of these cfDNA mutations were at original mutation levels of 0.03-0.1% and were deemed un-reliable due to the 'noise'. Following NaME-PrO these mutations were clearly scored. These data explain why the mutations were not found via exome sequencing of cfDNA and demonstrate the ability of NaME-PrO-MiSeq to recover the mutation fingerprint in cfDNA.

Study Design

Sources of DNA, Clinical Samples.

(a) DNA from cell lines: DNA with defined mutations are obtained from Horizon diagnostics, UK, and also from human cancer cell lines with fully sequenced genome (COSMIC mutation database, Cell Line Project, Sanger Institute, UK, cancer.sanger.ac.uk/cancergenome/projects/cell_lines/). This is serially diluted (5-0.01%) into wild-type human male genomic DNA. The resulting mutation abundance is verified via digital droplet PCR, ddPCR using the known methods[57]. To validate mutation enrichment in regions for which no mutation-containing cell line is available, error-prone PCR will be employed for the first 10 cycles of LMPCR in FIG. 2.

(b) DNA from clinical cancer samples and plasma-circulating-DNA: Resected lung tumor specimens and serial plasma samples previously collected from 100 cancer patients undergoing radio-chemo-therapy treatment are used. Blood obtained 1 week before therapy, at initiation of therapy, weekly throughout the course of therapy, and every 2-4 months after the end of therapy was processed for plasma and DNA extraction within 1 h of collection. Lymphocyte DNA and Qiagen-extracted circulating-DNA was stored at −80° C.

Selection of Lung Cancer Hotspot Mutation and Full Length Tumor Suppressor Gene Databases.

Hotspot mutations have been previously identified from large-scale sequencing of patients with lung cancer; in fact, screening for these mutations in cell-free DNA of patients with lung cancer using hybrid capture has demonstrated broad patient coverage[1, 2]. To enable benchmarking with recent, sophisticated approaches for hybrid capture and sequencing, focus will be put on panel development on the same hotspots and genes covered by the CAPP-Seq/iDES approach[1, 2]. The CAPP-Seq/iDES database includes 292 hotspots recurrently mutated in lung cancer as well as 521 full exons of 139 genes including well-known tumor suppressor genes, TP53, ALK, etc. The lung cancer patient coverage of the CAPP-Seq panel includes more than 96% of patients with lung adenocarcinoma or squamus cell carcinoma and identifies a median of 4 mutations per patient[1, 2].

Synthesis of Molecular Barcodes Containing Common 'Tags' and Ligation to Randomly Fragmented Genomic DNA To synthesize random molecular barcodes that ensure that each molecule of a given DNA allele is ligated to a different barcode, an excess of random barcodes over anticipated allelic copies must be used. For example, if the starting genomic DNA is 100 ng ($\sim 3 \times 10^4$ allelic copies), $10^8$ different barcodes during ligation with the randomly fragmented DNA so that the chances of the same barcode ligating to two alleles of the same sequence is exceedingly small. (If the same barcode ligates to two completely different sequences there is no concern). For a sequence diversity of $\sim 10^8$, oligonucleotide synthesis with a 14-mer region containing at each position a randomly chosen nucleotide plus a common ~18-mer oligonucleotide 'tag' on the 5-end, comprising part of the Illumina sequencing adaptor is used. FIG. 3A demonstrates the steps involved. Randomers are synthesized by Trilink Technologies, trilinkbiotech.com/products/oligo/randomers.asp. An extension reaction is then used to synthesize the opposite strand, resulting to double-stranded adaptors that will be prepared for end repair and ligation to fragments obtained by genomic DNA fragmentation.

For fragmentation of genomic DNA an enzymatic approach using Shearase™ is applied, as previously reported[8], followed by enzymatic end-repair to obtain blunt-ended 5'P-containing dsDNA. The fragmentation is adjusted to create random genomic DNA fragments in the range 100-200 bp which is appropriate for mutation enrichment via qNaME-PrO. Ligation to double-stranded barcoded adaptors is done also via the Illumina protocol. Following ligation, a 10-cycle PCR pre-amplification using the common 'tag' is applied to yield multiple copies of allelic-families, each family containing its own barcode. Following target enrichment using customized target enrichment on beads (EZ-kit, Roche-Nimblegen), NaME-PrO followed by 10 cycles PCR using the common tags is applied to enrich mutation-containing fragments, along with their barcodes. The NGS-ready library is sequenced. Following qNAME-PRO, DNA is processed for paired-end sequencing using the Illumina MiSeq platform. Although the method is applicable to all platforms, the modest cost of MiSeq instrument makes it accessible to many groups that do not have access to a high-end facility, hence a combination of NaME-Pro with MiSeq was chosen for highest impact. Mutations within WT DNA comprise 5% down to 0.01% abundance, using serial dilutions of genomic DNA with defined mutations. Sensitivity and selectivity of NAME-PRO-NGS is evaluated in triplicate and compared to (a) using conventional PCR-NGS, without molecular barcode corrections; and (b) using NGS corrected via molecular barcode technology. The molecular barcodes are employed as described below.

Strategy for Deriving the Original Mutation Abundance Via Allelic Barcode-Count Diversity, 'abcd'

Figure 2:
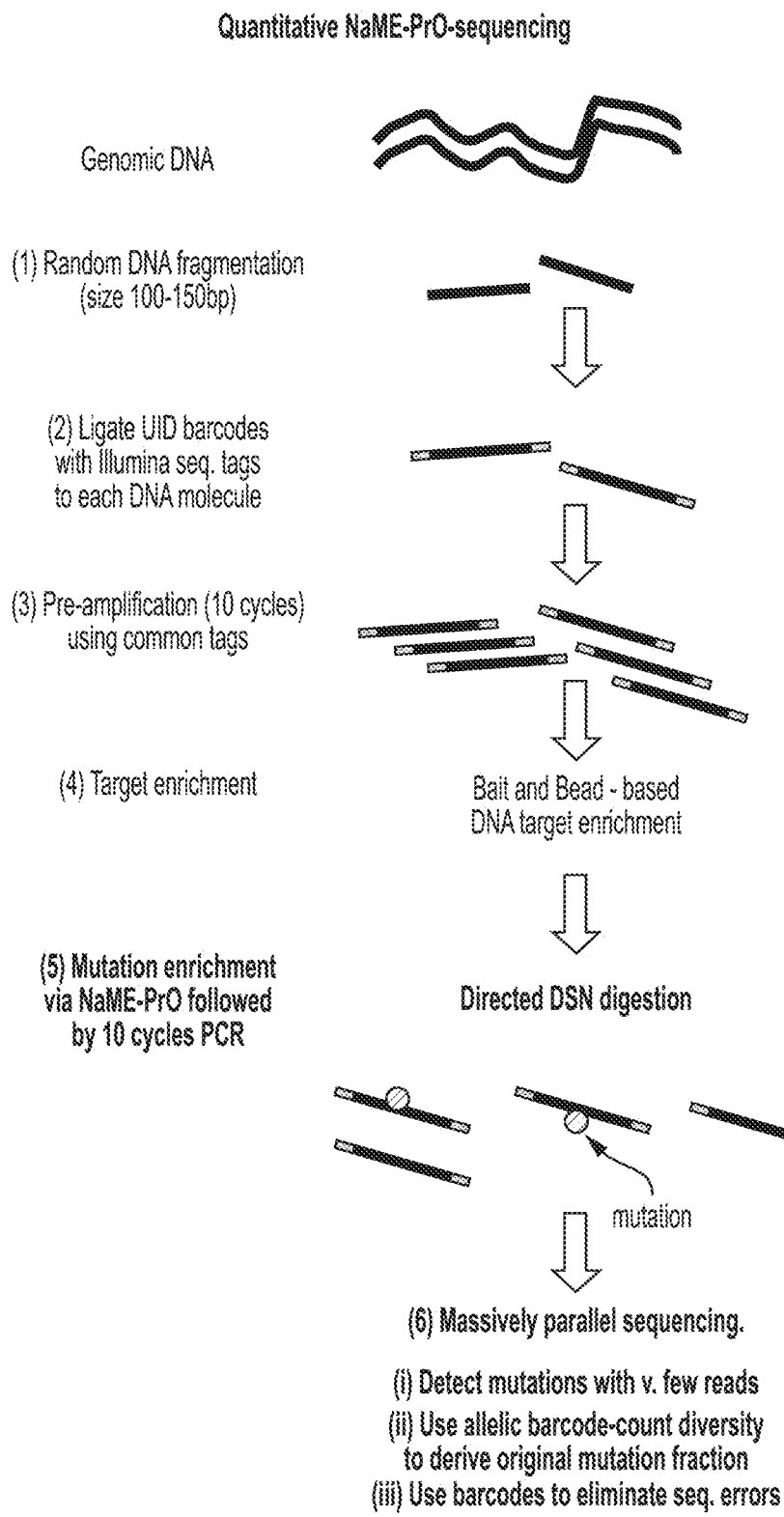
FIG. 2 describes qNAME-PRO-NGS using single-molecule barcoding to enable strictly quantitative assessment of original mutation abundance by implementing allelic barcode-count diversity (the 'abcd' approach). qNAME-PRO-NGS (i) enriches mutations by >100 fold and diminishes the number or reads required to call low-level mutations; (ii) derives original mutation abundance; and (iii) filters-out sequencing and PCR errors using the molecular barcodes. qNAME-PRO technology increases throughput by >100-fold and reduces cost for all existing NGS technologies and can be applied unchanged for future sequencing developments.

The abcd approach, described in FIG. 2, is a novel use of molecular barcodes to derive the true mutation abundance in the original DNA without being affected by potentially variable mutation enrichment during NaME-PrO. abcd is a general strategy to retain strict quantification following any technology for mutation enrichment. Briefly, in the simplified example of FIG. 3A with 1 mutated allele in a total of 6, barcodes are attached via ligation before any other manipulation of the sample. Following 10 cycles amplification of barcoded alleles there are multiple copies of allelic families ('polonies'), each polony containing a distinct barcode (FIG. 3A). The mutation abundance at this stage is equal to the fraction of distinct barcodes with mutations over all distinct barcodes. When qNaME-PrO is applied, the majority (but not all[8]), WT DNA from each allelic family are rendered un-amplifiable, hence they are reduced following a subsequent 10-cycle PCR step (FIG. 3A). In contrast, allelic families with mutations are amplified and their frequency is increased by >100 fold over allelic families containing WT. Despite enrichment of mutations over WT, the quantification of the original mutation abundance remains unaffected, as this is tied to the fraction of distinct barcodes with mutations over all distinct barcodes. Accordingly, during NGS the allelic barcode-count diversity, abcd, is an absolute measure of the original mutation abundance.

Figure 3B:
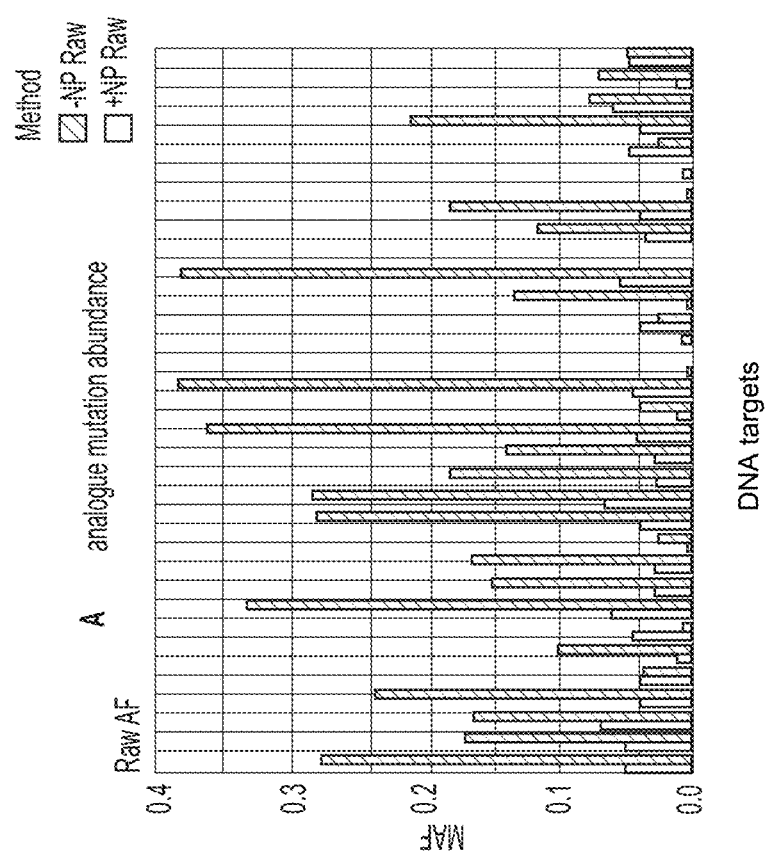
FIG. 3B shows data obtained from an experiment in which the workflow of FIG. 2 was applied to a set of 33 DNA targets with mutations in circulating DNA from a breast cancer patient without using the abcd approach (left panel) and using the abcd approach to determine the original abundance of mutant target nucleic acid (right panel). The light grey bars represent data obtained with mutant target nucleic acid enrichment using NaME-PrO. The dark grey bars represent data obtained without enrichment of mutant target nucleic acid.
Figure 3B:
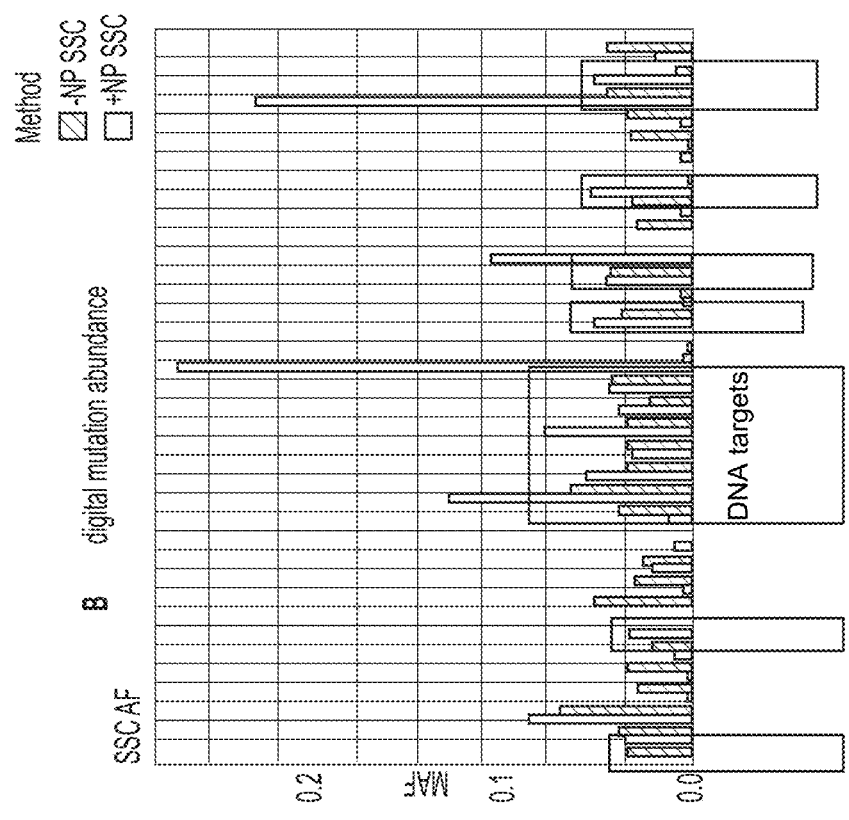

FIG. 3B demonstrates the effectiveness of the abcd approach. The workflow of FIG. 2 was applied to a set of 33 DNA targets with mutations in circulating DNA from a breast cancer patient. Following sequencing and analysis, allelic frequencies (MAF, y axis) for each of the 33 targets (X-axis) were measured with (light grey bars) and without NaME-PrO enrichment (dark grey bars). The left panel of FIG. 3B shows MAF when the mutation quantification does not take into account the unique molecular barcodes on each molecule, i.e. without using the abcd approach. The MAF quantification is distorted due to the NaME-PrO mutation enrichment, i.e. the MAF recorded after NaME-PrO application is very different from the true quantification of each mutated target as shown by the dark grey bars, which indicate the unbiased MAF. In contrast and as shown in the right panel of FIG. 3B, when the abcd approach is implemented by counting unique molecular barcodes, the mutant target allele abundance is less distorted by NaME-PrO enrichment. That is, in the right panel of FIG. 3B, the light grey and dark grey bars are closer together for most of the 33 targets (see comparison within boxes where the light grey and corresponding dark grey bars are almost equal). By counting unique molecular barcodes using the abcd approach, the distortion of data caused by mutation enrichment is corrected or overcome.

Elimination of PCR/Sequencing Errors Using Molecular Barcodes

In addition to using the molecular barcodes for deriving the original mutation abundance, the same barcodes are applied to eliminate PCR or sequencing errors, as reported[4-7]. In this approach[6], if a mutation is present in a given colony at least 90% of mutated fragments will be required to contain the same barcode for each polony. If this is not the case, the mutation is considered to be the result of a sequencing error or upstream PCR-error. Using this principle it is possible to reduce drastically the apparent sequencing errors during NGS4-7. Software to implement the abcd approach to derive mutation abundance, as well as the reduction of errors via molecular barcodes is developed.

Example 3: qNaME-PrO for Mutation Enrichment in Targeted Genomic Fractions Corresponding to Full-Length Exons of Recurrently Mutated Genes in Lung Cancer qNaME-PrO is adapted for 'mutation scanning' to enrich all possible mutations along 521 full exons of 139 genes that have been identified to be recurrently mutated in lung cancer[1, 2]. The methodologies of Example 1 are employed to validate qNaME-PrO application in full length genes.

Enrichment of Multiple Mutations Over Extended Sequence Regions by 'Tiling' NaME-PrO Oligonucleotide Probes It was demonstrated that in order to enrich multiple contiguous mutations along tumor suppressor genes like TP53 it is possible to 'tile' the overlapping 15 bp region of NaME-PrO probes (FIG. 10A and [8]) and perform several NaME-PrO reactions in parallel, followed by mixing the products and performing a single sequencing run. It was demonstrated that a contiguous probe tiling arrangement (FIG. 10B) can enrich multiple mutations along a (longer) 50 bp DNA section. This contiguous probe arrangement results to enrichments of 30-40-fold and provides a balance between mutation enrichment and number of probes needed to cover a given DNA fragment. Of note, lung CA gene fusions (e.g., EML4-ALK fusion[1]) that result to breakpoints within the mapped exons are also enriched by NaME-PrO, since probes corresponding to the WT cfDNA fragment do not bind adequately the fusion breakpoint and DSN will not digest those fragments, resulting to enrichment.

qNaME-PrO Application to Full Exons of Genes Significantly Mutated in Lung Cancer Following barcode ligation, 10-cycle pre-amplification and bead-based target enrichment as per FIG. 2 is performed, and the sample is split in 4 reactions. Each reaction separately employs qNaME-PrO using distinct groups of probes enriching mutations along sequential 50-bp-long sequence regions, as per FIG. 10B, thereby 'scanning' for mutation enrichment over the entire length of all targets. For example, any given 50 bp regions within a ~150 bp cfDNA fragment is enriched for mutations in one of the 4 distinct groups of probes. This is then tagged with a separate Illumina barcode-adaptor. All 4 NaME-PrO reactions are mixed and sequenced in a single MiSeq sequencing run.

The general methodologies employed in Example 2 is also applied in this Example to compare qNaME-PrO-NGS with current NGS approaches. Thus, sensitivity and selectivity of NAME-PRO-NGS sequencing is evaluated in triplicate and compared to (a) using conventional PCR-NGS, without molecular barcode corrections; and (b) using NGS corrected via molecular barcode technology.

Other Considerations (a) Amount of starting cfDNA material needed and anticipated lowest mutation abundance detectable via qNaME-PrO-NGS. Three main barriers limit NGS-based rare variant detection: (i) the intrinsic error frequency of high-throughput sequencing. As reported[36] using molecular barcode corrections allows mutation abundances as low as 0.01% to be discriminated from noise. (ii) The number of reads a sequencing platform can produce. As per FIG. 11 by using mutation enrichment via NaME-PrO the efficiency of sequencing increases by >100 fold with equivalent gains in throughput and cost. Therefore items (i) and (ii) are uniquely addressed by the novel qNaME-PrO technology that is applied in this work. (iii) The amount of starting material needed for carrying out the protocol in FIG. 2 is ~30 ng of cfDNA, corresponding to about 10,000 genomic copies. Considering that part of this cfDNA is highly fragmented and not readily amplifiable, it is estimated conservatively that about 3,000 genomic copies will make it to the mutation enrichment stage followed by sequencing. This enables mutation detection down to 0.03%, in good agreement with breast CA cfDNA exome-sequenced samples described above, FIG. 9. We anticipate using 30-60 ng cfDNA to enable mutation detection to 0.01-0.03%.

(b) Presence of SNPs in the same target region with a mutation. If there are SNPs within a few bp from targeted somatic mutations and within the overlap region of either the upper or lower strand probes, during NaME-PrO, such SNPs may prevent DSN from digesting WT samples effectively, thereby leading to reduced mutation enrichment. To circumvent this hurdle, provided these SNPs are included in public databases, additional probes that match each of SNP versions are included in the assay[8], such that irrespective of what SNP is present the WT sample will always have a fully-matched probe[8]. Furthermore, since normal lymphocyte DNA is available in the samples, presence of 'private' germline mutations will be accounted for and additional NaME-PrO probes can be included on a sample-to-sample basis, as needed.

Example 4: Tumor Fingerprints in Plasma and Application to Plasma Circulating DNA Tumor and circulating-DNA collected during the course of radio-chemo-therapy from a cohort of lung cancer patients are screened via qNaME-PrO-NGS, targeting both hotspot mutations as well as full length tumor suppressor gene and oncogene lung CA mutations. By tracing mutations over numerous DNA targets, the advantage of following multiple mutations rather than a single mutation in circulating-DNA is evaluated, thus circumventing biomarker sensitivity and specificity problems associated with tumor heterogeneity, uneven cfDNA release, or occult metastatic sites.

Application of NAME-PRO-NGS uniquely enables maximum efficiency sequencing for tracing of the mutated portion of the circulating-DNA in sequential samples obtained before, during and after completion of radio-chemo-therapy of lung cancer patients with few sequencing reads. Plasma-circulating DNA at regular time points obtained during radio-chemo-therapy from 100 lung cancer patients is analyzed via qNaME-PrO-NGS and the results assessed for concordance with the mutations identified in tumor tissue from each patient. Quantitative tracing of tumor DNA in the circulation during therapy can help assess therapeutic response[19, 20, 58]. Furthermore, periodic quantitative tracing of tumor DNA after completion of therapy can be used for surveillance, monitoring tumor remission or early detection of relapse[34].

The approach described in FIG. 1 is followed by omitting the fragmentation step since cfDNA is fragmented. The anticipated advantage of tracing the entire tumor mutational fingerprint at mutation abundances down to 0.01%-0.1%, as opposed to tracing a single mutation in plasma at the same lowest abundance, will be examined systematically in the sequential plasma samples. Reproducibility will be assessed via triplicate independent experiments from the same plasma samples. Mutations in key genes is independently verified by genotyping techniques (HRM, ddPCR). Concordance of plasma-identified mutations with the primary tumor will help assess the hypothesis that DNA from different tumor clones enters circulation at different stages[46, 48] during therapy.

Statistical Analysis

The ability of qNAME-PRO to identify a tumor signature in serial plasma samples from 100 lung cancer patients with paired tumor tissue is examined. The advantage of tracing a tumor fingerprint over tracing a single mutation (current practice) is assessed. This is interrogated in several ways. The qNaME-PrO-NGS approach as well as standard NGS to identify a tumor signature in plasma is used. It is assumed that the performance in tumor tissue represents the best outcome for plasma, and that either method may lose sensitivity. For this initial assessment, it is determined whether mutations were identified. The McNemar test is used to assess the ability of qNAME-PRO-NGS to identify mutations that are not identified by standard NGS. The mutations identified in tumor tissue are compared with those identified in plasma. It is anticipated that in doing this with NGS, it may be a binomial outcome—mutations detected in tumor may not be found in plasma due to sensitivity issues. The McNemar test is again used to assess the sensitivity of NGS in the plasma. With qNAME-PRO-NGS, the findings in plasma are compared with those in tumor, to identify when the full mutational fingerprint can be identified in plasma and when only a partial fingerprint can be found. Whether the number of mutations identified by qNAME-PRO changes over time in the serial samples is also examined. Each assessment will also be examined as part of a longitudinal model in which it is possible to detect tumor mutations in plasma by both, one, or neither method over time. This is modeled by using generalized estimating equations, allowing inclusion of patient characteristics in the model.

Power Calculation

It is desired to compare the ability to identify a tumor fingerprint in plasma samples based on a single mutation compared with multiple mutations. This data is analyzed using the McNemar test for paired assessments on the sample. For the purposes of calculation, it is assumed that the tumor fingerprint based on a single mutation will be detected with probability 0.50, and that the fingerprint based on multiple mutations will be detected 80% of the time. It is further assumed that half the patients who are detectable based on multiple mutations are also detectable based on single mutations, and therefore 40 samples will be detectable by multiple mutations only. It is assumed as well that 10 samples will be detectable only by the single mutation, and will be missed by the multiple mutations. In this setting, for the 100 paired samples that will be used the McNemar test would have 99% power testing at the 0.05 significance level to find that the multiple mutation technique is more sensitive. If it is assumed that either better performance for the multiple mutation approach or poorer performance for the single mutation approach will occur, it is found that the constraints of the 2×2 table force even greater divergence between the rate of discordant pairs, thereby increasing the power of the design to more than 99% for a range of assumptions. For example even if neither approach identifies tumor in plasma samples from 45% of the patients (which corresponds to an identification rate of 50% for the full fingerprint and 20% for the single marker), there is still 99% power to identify superiority of the full fingerprint with 100 samples. Even the scenario in which the single marker identifies disease in plasma 70% of the time, compared to 90% for the full fingerprint, has better than 99% power with 100 samples.

REFERENCES FOR EXAMPLES 1, 2 AND 3

[1] Newman A M, Bratman S V, To J, Wynne J F, Eclov N C, Modlin L A, Liu C L, Neal J W, Wakelee H A, Merritt R E, Shrager J B, Loo B W, Jr., Alizadeh A A, Diehn M: An ultrasensitive method for quantitating circulating tumor DNA with broad patient coverage. Nat Med 2014, 20:548-54.

[2] Newman A M, Lovejoy A F, Klass D M, Kurtz D M, Chabon J J, Scherer F, Stehr H, Liu C L, Bratman S V, Say C, Zhou L, Carter J N, West R B, Sledge G W, Jr., Shrager J B, Loo B W, Jr., Neal J W, Wakelee H A, Diehn M, Alizadeh A A: Integrated digital error suppression for improved detection of circulating tumor DNA. Nat Biotechnol 2016, 34:547-55.

[3] Adalsteinsson: Recent literature: listed in personal.broadinstitute.org/viktor/publications.html. 2016.

[4] Kinde I, Wu J, Papadopoulos N, Kinzler K W, Vogelstein B: Detection and quantification of rare mutations with massively parallel sequencing. Proc Natl Acad Sci USA 2011, 108:9530-5.

[5] Schmitt M W, Kennedy S R, Salk J J, Fox E J, Hiatt J B, Loeb L A: Detection of ultra-rare mutations by next-generation sequencing. Proc Natl Acad Sci USA 2012.

[6] Gregory M T, Bertout J A, Ericson N G, Taylor S D, Mukherjee R, Robins H S, Drescher C W, Bielas J H: Targeted single molecule mutation detection with massively parallel sequencing. Nucleic Acids Res 2016, 44:e22.

[7] Jee J, Rasouly A, Shamovsky I, Akivis Y, S R S, Mishra B, Nudler E: Rates and mechanisms of bacterial mutagenesis from maximum-depth sequencing. Nature 2016.

[8] Song C, Liu Y, Fontana R, Makrigiorgos A, Mamon H, Kulke M H, Makrigiorgos G M: Elimination of unaltered DNA in mixed clinical samples via nuclease-assisted minor-allele enrichment. Nucleic Acids Res 2016.

[9] Song C, Liu Y, Fontana R, Makrigiorgos A, Mamon H, Kulke M H, Makrigiorgos G M: Elimination of un-altered DNA in clinical samples via nuclease-assisted minor allele enrichment. Nucleic Acids Res, In Press 2016.

[10] Diehl F, Schmidt K, Choti M A, Romans K, Goodman S, Li M, Thornton K, Agrawal N, Sokoll L, Szabo S A, Kinzler K W, Vogelstein B, Diaz L A, Jr.: Circulating mutant DNA to assess tumor dynamics. Nat Med 2008, 14:985-90.

[11] Thomas R K, Nickerson E, Simons J F, Janne P A, Tengs T, Yuza Y, Garraway L A, Laframboise T, Lee J C, Shah K, O'Neill K, Sasaki H, Lindeman N, Wong K K, Borras A M, Gutmann E J, Dragnev K H, Debiasi R, Chen T H, Glatt K A, Greulich H, Desany B, Lubeski C K, Brockman W, Alvarez P, Hutchison S K, Leamon J H, Ronan M T, Turenchalk G S, Egholm M, Sellers W R, Rothberg J M, Meyerson M: Sensitive mutation detection in heterogeneous cancer specimens by massively parallel picoliter reactor sequencing. Nat Med 2006, 12:852-5.

[12] Shah S P, Morin R D, Khattra J, Prentice L, Pugh T, Burleigh A, Delaney A, Gelmon K, Guliany R, Senz J, Steidl C, Holt R A, Jones S, Sun M, Leung G, Moore R, Severson T, Taylor G A, Teschendorff A E, Tse K, Turashvili G, Varhol R, Warren R L, Watson P, Zhao Y, Caldas C, Huntsman D, Hirst M, Marra M A, Aparicio S: Mutational evolution in a lobular breast tumour profiled at single nucleotide resolution. Nature 2009, 461:809-13.

[13] Reis-Filho J: Next-generation sequencing. Breast Cancer Research 2009, 11:S12.

[14] Milbury C A, Correll M, Quackenbush J, Rubio R, Makrigiorgos G M: COLD-PCR enrichment of rare cancer mutations prior to targeted amplicon resequencing. Clin Chem 2012, 58:580-9.

[15] Gray J: Cancer: Genomics of metastasis. Nature 2010, 464:989-90.

[16] Tang S, Huang T: Characterization of mitochondrial DNA heteroplasmy using a parallel sequencing system. Biotechniques, 48:287-96.

[17] Qin W, Kozlowski P, Taillon B E, Bouffard P, Holmes A J, Janne P, Camposano S, Thiele E, Franz D, Kwiatkowski D J: Ultra deep sequencing detects a low rate of mosaic mutations in tuberous sclerosis complex. Hum Genet, 127:573-82.

[18] Schmitt M W, Kennedy S R, Salk J J, Fox E J, Hiatt J B, Loeb L A: Detection of ultra-rare mutations by next-generation sequencing. Proc Natl Acad Sci USA 2012, 109:14508-13.

[19] Misale S, Yaeger R, Hobor S, Scala E, Janakiraman M, Liska D, Valtorta E, Schiavo R, Buscarino M, Siravegna G, Bencardino K, Cercek A, Chen C T, Veronese S, Zanon C, Sartore-Bianchi A, Gambacorta M, Gallicchio M, Vakiani E, Boscaro V, Medico E, Weiser M, Siena S, Di Nicolantonio F, Solit D, Bardelli A: Emergence of KRAS mutations and acquired resistance to anti-EGFR therapy in colorectal cancer. Nature 2012, 486:532-6.

[20] Diaz L A, Jr., Williams R T, Wu J, Kinde I, Hecht J R, Berlin J, Allen B, Bozic I, Reiter J G, Nowak M A, Kinzler K W, Oliner K S, Vogelstein B: The molecular evolution of acquired resistance to targeted EGFR blockade in colorectal cancers. Nature 2012, 486:537-40.

[21] Kuang Y, Rogers A, Yeap B Y, Wang L, Makrigiorgos M, Vetrand K, Thiede S, Distel R J, Janne P A: Noninvasive detection of EGFR T790M in gefitinib or erlotinib resistant non-small cell lung cancer. Clin Cancer Res 2009, 15:2630-6.

[22] Taniguchi K, Uchida J, Nishino K, Kumagai T, Okuyama T, Okami J, Higashiyama M, Kodama K, Imamura F, Kato K: Quantitative detection of EGFR mutations in circulating tumor DNA derived from lung adenocarcinomas. Clin Cancer Res 2011, 17:7808-15.

[23] Girotti M R, Gremel G, Lee R, Galvani E, Rothwell D, Viros A, Mandal A K, Lim K H, Saturno G, Furney S J, Baenke F, Pedersen M, Rogan J, Swan J, Smith M, Fusi A, Oudit D, Dhomen N, Brady G, Lorigan P, Dive C, Marais R: Application of Sequencing, Liquid Biopsies, and Patient-Derived Xenografts for Personalized Medicine in Melanoma. Cancer Discov 2016, 6:286-99.

[24] Thress K S, Paweletz C P, Felip E, Cho B C, Stetson D, Dougherty B, Lai Z, Markovets A, Vivancos A, Kuang Y, Ercan D, Matthews S E, Cantarini M, Barrett J C, Janne P A, Oxnard G R: Acquired EGFR C797S mutation mediates resistance to AZD9291 in non-small cell lung cancer harboring EGFR T790M. Nat Med 2015, 21:560-2.

[25] Oxnard G R, Paweletz C P, Kuang Y, Mach S L, O'Connell A, Messineo M M, Luke J J, Butaney M, Kirschmeier P, Jackman D M, Janne P A: Noninvasive Detection of Response and Resistance in EGFR-Mutant Lung Cancer Using Quantitative Next-Generation Genotyping of Cell-Free Plasma DNA. Clin Cancer Res 2014.

[26] Schwaederle M, Husain H, Fanta P T, Piccioni D E, Kesari S, Schwab R B, Patel S P, Harismendy O, Ikeda M, Parker B A, Kurzrock R: Use of Liquid Biopsies in Clinical Oncology: Pilot Experience in 168 Patients. Clin Cancer Res 2016.

[27] Thierry A R, Mouliere F, El Messaoudi S, Mollevi C, Lopez-Crapez E, Rolet F, Gillet B, Gongora C, Dechelotte P, Robert B, Del Rio M, Lamy P J, Bibeau F, Nouaille M, Loriot V, Jarrousse A S, Molina F, Mathonnet M, Pezet D, Ychou M: Clinical validation of the detection of KRAS and BRAF mutations from circulating tumor DNA. Nat Med 2014, 20:430-5.

[28] Dawson S J, Tsui D W, Murtaza M, Biggs H, Rueda O M, Chin S F, Dunning M J, Gale D, Forshew T, Mahler-Araujo B, Rajan S, Humphray S, Becq J, Halsall D, Wallis M, Bentley D, Caldas C, Rosenfeld N: Analysis of circulating tumor DNA to monitor metastatic breast cancer. N Engl J Med 2013, 368:1199-209.

[29] Roschewski M, Dunleavy K, Pittaluga S, Moorhead M, Pepin F, Kong K, Shovlin M, Jaffe E S, Staudt L M, Lai C, Steinberg S M, Chen C C, Zheng J, Willis T D, Faham M, Wilson W H: Circulating tumour DNA and C T monitoring in patients with untreated diffuse large B-cell lymphoma: a correlative biomarker study. The lancet oncology 2015, 16:541-9.

[30] Higgins M J, Jelovac D, Barnathan E, Blair B, Slater S, Powers P, Zorzi J, Jeter S C, Oliver G R, Fetting J, Emens L, Riley C, Stearns V, Diehl F, Angenendt P, Huang P, Cope L, Argani P, Murphy K M, Bachman K E, Greshock J, Wolff A C, Park B H: Detection of tumor PIK3C A status in metastatic breast cancer using peripheral blood. Clin Cancer Res 2012, 18:3462-9.

[31] Murphy D M, Bejar R, Stevenson K, Neuberg D, Shi Y, Cubrich C, Richardson K, Eastlake P, Garcia-Manero G, Kantarjian H, Ebert B L, Mike Makrigiorgos G: NRAS mutations with low allele burden have independent prognostic significance for patients with lower risk myelodysplastic syndromes. Leukemia 2013, 27:2077-81.

[32] Reckamp K L, Melnikova V O, Karlovich C, Sequist L V, Camidge D R, Wakelee H, Perol M, Oxnard G R, Kosco K, Croucher P, Samuelsz E, Vibat C R, Guerrero S, Geis J, Berz D, Mann E, Matheny S, Rolfe L, Raponi M, Erlander M G, Gadgeel S: A Highly Sensitive and Quantitative Test Platform for Detection of NSCLC EGFR Mutations in Urine and Plasma. J Thorac Oncol 2016.

[33] Hindson B J, Ness K D, Masquelier D A, Belgrader P, Heredia N J, Makarewicz A J, Bright L T, Lucero M Y, Hiddessen A L, Legler T C, Kitano T K, Hodel M R, Petersen J F, Wyatt P W, Steenblock E R, Shah P H, Bousse U, Troup C B, Mellen J C, Wittmann D K, Erndt N G, Cauley T H, Koehler R T, So A P, Dube S, Rose K A, Montesclaros L, Wang S, Stumbo D P, Hodges S P, Romine S, Milanovich F P, White H E, Regan J F, Karlin-Neumann G A, Hindson C M, Saxonov S, Colston B W: High-throughput droplet digital PCR system for absolute quantitation of DNA copy number. Anal Chem 2011, 83:8604-10.

[34] Diaz L A, Jr., Bardelli A: Liquid biopsies: genotyping circulating tumor DNA. J Clin Oncol 2014, 32:579-86.

[35] Li J, Wang L, Mamon H, Kulke M H, Berbeco R, Makrigiorgos G M: Replacing PCR with COLD-PCR enriches variant DNA sequences and redefines the sensitivity of genetic testing. Nat Med 2008, 14:579-84.

[36] Milbury C A, Li J, Makrigiorgos G M: Ice-COLD-PCR enables rapid amplification and robust enrichment for low-abundance unknown DNA mutations. Nucleic Acids Res 2011, 39:e2.

[37] How-Kit A, Lebbe C, Bousard A, Daunay A, Mazaleyrat N, Daviaud C, Mourah S, Tost J: Ultrasensitive detection and identification of BRAF V600 mutations in fresh frozen, FFPE, and plasma samples of melanoma patients by E-ice-COLD-PCR. Anal Bioanal Chem 2014, 406:5513-20.

[38] Narayan A, Carriero N J, Gettinger S N, Kluytenaar J, Kozak K R, Yock T I, Muscato N E, Ugarelli P, Decker R H, Patel A A: Ultrasensitive measurement of hotspot mutations in tumor DNA in blood using error-suppressed multiplexed deep sequencing. Cancer Res 2012, 72:3492-8.

[39] Forshew T, Murtaza M, Parkinson C, Gale D, Tsui D W, Kaper F, Dawson S J, Piskorz A M, Jimenez-Linan M, Bentley D, Hadfield J, May A P, Caldas C, Brenton J D, Rosenfeld N: Noninvasive identification and monitoring of cancer mutations by targeted deep sequencing of plasma DNA. Sci Transl Med 2012, 4:136ra68.

[40] Lou D I, Hussmann J A, McBee R M, Acevedo A, Andino R, Press W H, Sawyer S L: High-throughput DNA sequencing errors are reduced by orders of magnitude using circle sequencing. Proc Natl Acad Sci USA 2013, 110:19872-7.

[41] Shagin D A, Rebrikov D V, Kozhemyako V B, Altshuler I M, Shcheglov A S, Zhulidov P A, Bogdanova E A, Staroverov D B, Rasskazov V A, Lukyanov S: A novel method for SNP detection using a new duplex-specific nuclease from crab hepatopancreas. Genome Res 2002, 12:1935-42.

[42] Gnirke A, Melnikov A, Maguire J, Rogov P, LeProust E M, Brockman W, Fennell T, Giannoukos G, Fisher S, Russ C, Gabriel S, Jaffe D B, Lander E S, Nusbaum C: Solution hybrid selection with ultra-long oligonucleotides for massively parallel targeted sequencing. Nat Biotechnol 2009, 27:182-9.

[43] Mertes F, Elsharawy A, Sauer S, van Helvoort J M, van der Zaag P J, Franke A, Nilsson M, Lehrach H, Brookes A J: Targeted enrichment of genomic DNA regions for next-generation sequencing. Briefings in functional genomics 2011, 10:374-86.

[44] Wagner P D, Verma M, Srivastava S: Challenges for Biomarkers in Cancer Detection. Annals of the New York Academy of Sciences 2004, 1022:9-16.

[45] Kopreski M S, Benko F A, Borys D J, Khan A, McGarrity T J, Gocke C D: Somatic mutation screening: identification of individuals harboring K-ras mutations with the use of plasma DNA. Journal of the National Cancer Institute 2000, 92:918-23.

[46] Alix-Panabieres C, Pantel K: Clinical Applications of Circulating Tumor Cells and Circulating Tumor DNA as Liquid Biopsy. Cancer Discov 2016, 6:479-91.

[47] Bettegowda C, Sausen M, Leary R J, Kinde I, Wang Y, Agrawal N, Bartlett B R, Wang H, Luber B, Alani R M, Antonarakis E S, Azad N S, Bardelli A, Brem H, Cameron J L, Lee C C, Fecher L A, Gallia G L, Gibbs P, Le D, Giuntoli R L, Goggins M, Hogarty M D, Holdhoff M, Hong S M, Jiao Y, Juhl H H, Kim J J, Siravegna G, Laheru D A, Lauricella C, Lim M, Lipson E J, Marie S K, Netto G J, Oliner K S, Olivi A, Olsson L, Riggins G J, Sartore-Bianchi A, Schmidt K, Shih 1 M, Oba-Shinjo S M, Siena S, Theodorescu D, Tie J, Harkins T T, Veronese S, Wang T L, Weingart J D, Wolfgang C L, Wood L D, Xing D, Hruban R H, Wu J, Allen P J, Schmidt C M, Choti M A, Velculescu V E, Kinzler K W, Vogelstein B, Papadopoulos N, Diaz L A, Jr.: Detection of circulating tumor DNA in early- and late-stage human malignancies. Sci Transl Med 2014, 6:224ra24.

[48] Hibi K, Robinson C R, Booker S, Wu L, Hamilton S R, Sidransky D, Jen J: Molecular detection of genetic alterations in the serum of colorectal cancer patients. Cancer Res 1998, 58:1405-7.

[49] Richardson A L, Iglehart J D: BEAMing up personalized medicine: mutation detection in blood. Clin Cancer Res 2012, 18:3209-11.

[50] Lawrence M S, Stojanov P, Polak P, Kryukov G V, Cibulskis K, Sivachenko A, Carter S L, Stewart C, Mermel C H, Roberts S A, Kiezun A, Hammerman P S, McKenna A, Drier Y, Zou L, Ramos A H, Pugh T J, Stransky N, Helman E, Kim J, Sougnez C, Ambrogio L, Nickerson E, Shefler E, Cortes M L, Auclair D, Saksena G, Voet D, Noble M, DiCara D, Lin P, Lichtenstein L, Heiman D I, Fennell T, Imielinski M, Hernandez B, Hodis E, Baca S, Dulak A M, Lohr J, Landau D A, Wu C J, Melendez-Zajgla J, Hidalgo-Miranda A, Koren A, McCarroll S A, Mora J, Lee R S, Crompton B, Onofrio R, Parkin M, Winckler W, Ardlie K, Gabriel S B, Roberts C W, Biegel J A, Stegmaier K, Bass A J, Garraway L A, Meyerson M, Golub T R, Gordenin D A, Sunyaev S, Lander E S, Getz G: Mutational heterogeneity in cancer and the search for new cancer-associated genes. Nature 2013, 499:214-8.

[51] Hiatt J B, Pritchard C C, Salipante S J, O'Roak B J, Shendure J: Single molecule molecular inversion probes for targeted, high-accuracy detection of low-frequency variation. Genome Res 2013, 23:843-54.

[52] Flaherty P, Natsoulis G, Muralidharan O, Winters M, Buenrostro J, Bell J, Brown S, Holodniy M, Zhang N, Ji H P: Ultrasensitive detection of rare mutations using next-generation targeted resequencing. Nucleic Acids Res 2012, 40:e2.

[53] Koboldt D C, Chen K, Wylie T, Larson D E, McLellan M D, Mardis E R, Weinstock G M, Wilson R K, Ding L: VarScan: variant detection in massively parallel sequencing of individual and pooled samples. Bioinformatics 2009, 25:2283-5.

[54] Bansal V, Libiger O, Torkamani A, Schork N J: Statistical analysis strategies for association studies involving rare variants. Nat Rev Genet 2010, 11:773-85.

[55] Bidard F C, Weigelt B, Reis-Filho J S: Going with the flow: from circulating tumor cells to DNA. Sci Transl Med 2013, 5:207ps14.

[56] Ozsolak F: Third-generation sequencing techniques and applications to drug discovery. Expert Opin Drug Discov 2012, 7:231-43.

[57] Song C, Castellanos-Rizaldos E, Bejar R, Ebert B L, Makrigiorgos G M: DMSO Increases Mutation Scanning Detection Sensitivity of High-Resolution Melting in Clinical Samples. Clin Chem 2015, 61:1354-62.

[58] Siravegna G, Mussolin B, Buscarino M, Corti G, Cassingena A, Crisafulli G, Ponzetti A, Cremolini C, Amatu A, Lauricella C, Lamba S, Hobor S, Avallone A, Valtorta E, Rospo G, Medico E, Motta V, Antoniotti C, Tatangelo F, Bellosillo B, Veronese S, Budillon A, Montagut C, Racca P, Marsoni S, Falcone A, Corcoran R B, Di Nicolantonio F, Loupakis F, Siena S, Sartore-Bianchi A, Bardelli A: Clonal evolution and resistance to EGFR blockade in the blood of colorectal cancer patients. Nat Med 2015.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be appreciated that embodiments described in this document using an open-ended transitional phrase (e.g., "comprising") are also contemplated, in alternative embodiments, as "consisting of" and "consisting essentially of" the feature described by the open-ended transitional phrase. For example, if the disclosure describes "a composition comprising A and B", the disclosure also contemplates the alternative embodiments "a composition consisting of A and B" and "a composition consisting essentially of A and B".

What is claimed is:

1. A method of determining original abundance of mutant alleles of a target nucleic acid in a sample of genomic DNA, the method comprising
    providing a sample of double-stranded genomic DNA fragments anticipated to comprise mutant alleles of the target nucleic acid and wild-type alleles of the target nucleic acid, wherein each terminus of the genomic DNA fragments is attached to a unique double-stranded barcode and a double-stranded common sequence tag, wherein the common sequence tag is located upstream of the unique barcode;
    amplifying a portion of the double-stranded genomic DNA fragments using primers that are complementary to the common sequence tag;
    enriching in the amplified portion the mutant alleles of the target nucleic acids relative to the wild-type alleles of the target nucleic acids;
    obtaining a measure of total number of unique barcodes associated with mutant target nucleic acid sequence in the enriched portion; and
    obtaining a measure of total number of unique barcodes associated with the sample;
    wherein the original abundance of the mutant alleles of the target nucleic acid in the sample of genomic DNA is determined by calculating the ratio of the total number of unique barcodes associated with mutant target nucleic acid sequence to the total number of unique barcodes associated with the sample.

2. The method of claim 1, wherein the total number of unique barcodes associated with the sample is the total number of unique barcodes associated with mutant and wild-type target nucleic acid sequence in the enriched portion.

3. The method of claim 1, further comprising:
    obtaining a measure of total number of unique barcodes associated with wild-type target nucleic acid sequence in an un-enriched control sample,
    wherein the total number of unique barcodes associated with the sample is the sum of the total number of unique barcodes associated with mutant target nucleic acid sequence in the enriched portion and the total number of unique barcodes associated with wild-type target nucleic acid sequence in the un-enriched control sample.

4. The method of claim 1, further comprising enriching both the mutant target nucleic acids and wild-type target nucleic acids relative to total nucleic acids in the sample.

5. The method of claim 4, wherein the enriching the mutant target nucleic acids and wild-type target nucleic acids relative to total nucleic acids in the sample comprises
    amplifying the double-stranded genomic DNA fragments in the sample using a first and second primer, wherein the first primer is complementary to the double-stranded common sequence tag, and the second primer is a nested gene-specific primer comprising a sequence tag that is different from the double-stranded common sequence tag, wherein the nested gene-specific primer is nested relative to the primers that are complementary to the common sequence tag.

6. The method of claim 1, further comprising obtaining sequences of the mutant target nucleic acids and wild-type target nucleic acids in the enriched portion.

7. The method of claim 1, wherein the double-stranded genomic DNA fragments are 40-200 bp in length.

8. The method of claim 1, wherein the unique barcode is 8-14 bp in length.

9. The method of claim 1, wherein the common sequence tag is 16-40 bp in length.

10. The method of claim 1, further comprising attaching the double-stranded genomic DNA fragments to the unique double-stranded barcodes.

11. The method of claim 10, wherein the attaching of double-stranded fragments of genomic DNA to the unique barcodes is performed at a ratio of $10^7$-$10^9$ unique barcodes to 100 ng double-stranded genomic DNA fragments present in the sample.

12. The method of claim 10, wherein the attaching comprises starting from a single-stranded barcode, synthesizing the opposite strand of the single-stranded barcode using an extension reaction to form a double-stranded barcode, and then ligating to an end of the double-stranded genomic DNA fragment.

13. The method of claim 10, wherein the attaching of barcodes comprises PCR using oligonucleotide primers, wherein each oligonucleotide primer comprises a common tag portion, a unique barcode portion, and a target-specific portion.

14. The method of claim 1, wherein the mutant target nucleic acid in the amplified portion is enriched by 2-300 fold relative to the wild-type target nucleic acid in the amplified portion.

15. The method of claim 1, wherein the enriching the mutant alleles of the target nucleic acids in the amplified portion relative to the wild-type alleles of the target nucleic acids in the amplified portion comprises subjecting the amplified portion to one or more of the following: Nuclease-assisted Minor-allele Enrichment using Probe Overlap (NaME-PrO), Coamplification at Lower Denaturation temperature-PCR (COLD-PCR), Improved and Complete Enrichment COLD-PCR (ice-COLD-PCR), Temperature-Tolerant-ice-COLD-PCR (TT-ice-COLD-PCR), toehold PCR blocker-PCR using locked nucleic acids (LNA), peptide nucleic acids (PNA), or blockers with other modified nucleotides, CRISP-R-mediated mutation enrichment by selecting mutated alleles or removing wild-type alleles and Differential Strand Separation at Critical Temperature (DiS-SECT).

16. The method of claim 15, wherein the NaMe-PrO comprises
    (a) preparing an amplification reaction mixture comprising the double-stranded mutant and wild-type target nucleic acids, a thermostable double strand-specific nuclease (DSN), PCR amplification components, and a pair of oligonucleotide probes, one of which is complementary to the wild-type nucleic acid top strand and the other is complementary to the wild-type nucleic acid bottom strand, wherein the probes overlap each other by 10-15 base pairs such that the overlap coincides with a region of the mutant target nucleic acid;

(b) subjecting the reaction mixture to a denaturing temperature to permit denaturation of the wild-type nucleic acid and the mutant target nucleic acid;

(c) reducing the temperature to permit hybridization of the probes to their corresponding sequences on the wild-type and mutant target nucleic acids thereby forming complementary wild-type-probe duplexes, wherein the DSN cleaves the complementary wild-type-probe duplexes relative to the partially complementary target mutant-probe duplexes; and (d) subjecting the reaction mixture to an amplification condition thereby enriching the mutant target nucleic acid relative to the wild-type nucleic acid.

17. The method of claim 1, further comprising determining the original abundance of one or more additional mutant alleles of the target nucleic acids at different loci on the genomic DNA.

18. The method of claim 17, wherein the mutant alleles of the target nucleic acids are enriched relative to wild-type alleles of the target nucleic acids by subjecting the amplified portion to multiplexed NaME-PrO.

19. The method of claim 18, wherein the multiplexed NaME-PrO uses overlapping probe pairs in parallel reactions, wherein each parallel reaction uses a distinct pair of overlapping probes, such that the totality of overlapping probe pairs span a contiguous region of genomic DNA of interest.

20. The method of claim 18, wherein the multiplexed NaME-PrO uses continuous and non-overlapping probe pairs in parallel reactions, wherein each parallel reaction uses a distinct pair of non-overlapping probes, such that the totality of non-overlapping probe pairs span a contiguous region of genomic DNA of interest.

* * * * *